(12) United States Patent
Gill et al.

(10) Patent No.: US 8,975,377 B2
(45) Date of Patent: Mar. 10, 2015

(54) CANCER TREATMENT USING HUMANIZED ANTIBODIES THAT BIND TO EPHB4

(75) Inventors: Parkash Gill, Agoura Hills, CA (US); Valery Krasnoperov, South Pasadena, CA (US); Simon William Keen, Cambridgeshire (GB); Timothy David Jones, Cambridgeshire (GB); Francis Joseph Carr, Aberdeenshire (GB)

(73) Assignee: Vasgene Therapeutics, Inc, Los Angeles, CA (US)

( * ) Notice: Subject to any disclaimer, the term of this patent is extended or adjusted under 35 U.S.C. 154(b) by 693 days.

(21) Appl. No.: 12/228,255

(22) Filed: Aug. 11, 2008

(65) Prior Publication Data

US 2009/0196880 A1 Aug. 6, 2009

Related U.S. Application Data

(60) Provisional application No. 60/964,496, filed on Aug. 13, 2007.

(51) Int. Cl.
*C12P 21/08* (2006.01)
*C07K 16/28* (2006.01)
*C07K 16/30* (2006.01)
*A61K 39/00* (2006.01)

(52) U.S. Cl.
CPC .............. *C07K 16/2866* (2013.01); *C07K 16/30* (2013.01); *A61K 2039/505* (2013.01); *C07K 2317/24* (2013.01); *C07K 2317/56* (2013.01); *C07K 2317/565* (2013.01); *C07K 2317/567* (2013.01)
USPC ..................................................... 530/387.3

(58) Field of Classification Search
USPC .................................... 530/350, 387.1, 387.3
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 4,946,778 A | 8/1990 | Ladner et al. | |
| 5,225,539 A | 7/1993 | Winter et al. | |
| 5,260,203 A | 11/1993 | Ladner et al. | |
| 5,512,591 A | 4/1996 | Halperin et al. | |
| 5,565,332 A | 10/1996 | Hoogenboom et al. | |
| 5,624,821 A | 4/1997 | Winter et al. | |
| 5,624,899 A | 4/1997 | Bennett | |
| 5,635,177 A | 6/1997 | Bennett et al. | |
| 5,648,260 A | 7/1997 | Winter et al. | |
| 5,693,761 A | 12/1997 | Queen et al. | |
| 5,693,762 A | 12/1997 | Queen et al. | |
| 5,770,599 A | 6/1998 | Gibson et al. | |
| 5,795,734 A | 8/1998 | Flanagan et al. | |
| 5,821,337 A | 10/1998 | Carter et al. | |
| 5,824,303 A | 10/1998 | Bartley et al. | |
| 5,859,205 A | 1/1999 | Adair et al. | |
| 5,864,020 A | 1/1999 | Bennett | |
| 6,015,711 A | 1/2000 | Olson et al. | |
| 6,103,889 A | 8/2000 | Whitlow et al. | |
| 6,180,370 B1 | 1/2001 | Queen et al. | |
| 6,303,769 B1 | 10/2001 | Cerretti | |
| 6,331,415 B1 | 12/2001 | Cabilly et al. | |
| 6,355,245 B1 | 3/2002 | Evans et al. | |
| 6,407,213 B1 | 6/2002 | Carter et al. | |
| 6,413,730 B1 | 7/2002 | Holland | |
| 6,440,954 B1 | 8/2002 | Haber et al. | |
| 6,479,459 B1 | 11/2002 | Cerretti | |
| 6,492,140 B2 | 12/2002 | Cerretti | |
| 6,514,497 B1 | 2/2003 | Briskin et al. | |
| 6,548,640 B1 | 4/2003 | Winter et al. | |
| 6,579,683 B2 | 6/2003 | Wang et al. | |
| 6,632,927 B2 | 10/2003 | Adair et al. | |
| 6,639,055 B1 | 10/2003 | Carter et al. | |
| 6,797,492 B2 | 9/2004 | Daugherty et al. | |
| 6,864,227 B1 | 3/2005 | Wang et al. | |
| 6,887,674 B1 | 5/2005 | Wang et al. | |
| 6,916,625 B2 | 7/2005 | Wang et al. | |
| 7,087,724 B2 * | 8/2006 | Carr et al. ................. | 530/387.3 |
| 7,192,586 B2 * | 3/2007 | Bander ...................... | 424/155.1 |
| 7,381,410 B2 | 6/2008 | Krasnoperov et al. | |
| 2002/0136726 A1 | 9/2002 | Anderson et al. | |
| 2002/0146420 A1 | 10/2002 | Bennett | |
| 2004/0110150 A1 | 6/2004 | Koller et al. | |
| 2004/0234520 A1 | 11/2004 | Aguet et al. | |
| 2004/0247592 A1 | 12/2004 | Roifman et al. | |
| 2005/0033028 A1 | 2/2005 | Leung | |
| 2005/0084873 A1 | 4/2005 | Krasnoperov et al. | |
| 2005/0204412 A1 | 9/2005 | Wang et al. | |
| 2005/0238646 A1 | 10/2005 | Ledbetter et al. | |
| 2005/0249736 A1 | 11/2005 | Krasnoperov et al. | |
| 2006/0035328 A1 | 2/2006 | Wang et al. | |

(Continued)

FOREIGN PATENT DOCUMENTS

EP 0 120 694 B1 10/1984
EP 0 194 276 B1 9/1986

(Continued)

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Elgert (Immunology: Understating the Immune System, 1996, p. 123).*
Rudikoff et al (Proceedings National Academy Sciences. USA 1982 vol. 79:1979-1983).*
[Fundamental Immunology p. 242 (William E. Paul, M.D. ed., 3d ed; 1993].*

(Continued)

*Primary Examiner* — Brad Duffy
(74) *Attorney, Agent, or Firm* — Craig A Crandall

(57) ABSTRACT

In certain embodiments, this application provides humanized antibodies that bind to the EphB4 protein as well as uses of the antibodies for therapeutic purposes.

8 Claims, 6 Drawing Sheets

(56) References Cited

U.S. PATENT DOCUMENTS

| | | | |
|---|---|---|---|
| 2006/0121042 A1 | 6/2006 | Dall Acqua et al. |
| 2006/0134118 A1 | 6/2006 | Stephenson |
| 2008/0131436 A1 | 6/2008 | Krasnoperov et al. |

FOREIGN PATENT DOCUMENTS

| | | | |
|---|---|---|---|
| EP | 0 239 400 B1 | | 9/1987 |
| EP | 0 404 097 B1 | | 12/1990 |
| EP | 0 633 315 A2 | | 1/1995 |
| EP | 0 999 278 | | 5/2000 |
| WO | WO-86/01533 | | 3/1986 |
| WO | WO-93/00425 | | 1/1993 |
| WO | WO-93/11161 | | 6/1993 |
| WO | WO-93/15201 | | 8/1993 |
| WO | WO-94/10202 | | 5/1994 |
| WO | WO-94/11020 | | 5/1994 |
| WO | WO-94/28027 | | 12/1994 |
| WO | WO-94/29351 | | 12/1994 |
| WO | WO-95/27061 | | 10/1995 |
| WO | WO-96/01839 | | 1/1996 |
| WO | WO-96/02645 | | 2/1996 |
| WO | WO-96/03043 | | 2/1996 |
| WO | WO-96/09384 | | 3/1996 |
| WO | WO-96/13518 | | 5/1996 |
| WO | WO-96/23000 | | 8/1996 |
| WO | WO-96/26958 | | 9/1996 |
| WO | WO-96/36713 | | 11/1996 |
| WO | WO-97/09427 | | 3/1997 |
| WO | WO-97/23629 | | 7/1997 |
| WO | WO-97/44453 | | 11/1997 |
| WO | WO-98/01548 | | 1/1998 |
| WO | WO-98/43960 | | 10/1998 |
| WO | WO-98/45331 | | 10/1998 |
| WO | WO-98/45708 | | 10/1998 |
| WO | WO-98/47531 | | 10/1998 |
| WO | WO 9852976 A1 * | | 11/1998 |
| WO | WO-99/08696 | | 2/1999 |
| WO | WO-99/17796 | | 4/1999 |
| WO | WO-99/51642 | | 10/1999 |
| WO | WO-99/52541 | | 10/1999 |
| WO | WO-00/24413 | | 5/2000 |
| WO | WO-00/30673 | | 6/2000 |
| WO | WO-00/34317 | | 6/2000 |
| WO | WO-02/11785 | | 2/2002 |
| WO | WO-02/26827 | | 4/2002 |
| WO | WO-02/058538 | | 8/2002 |
| WO | WO-02/061055 | | 8/2002 |
| WO | WO-02/079382 | | 10/2002 |
| WO | WO-02/102854 | | 12/2002 |
| WO | WO-02/102972 | | 12/2002 |
| WO | WO-02/102973 | | 12/2002 |
| WO | WO-03/004057 | | 1/2003 |
| WO | WO-03/094859 | | 11/2003 |
| WO | WO-2004/008425 | | 1/2004 |
| WO | WO-2004/014292 | | 2/2004 |
| WO | WO-2004/024773 | | 3/2004 |
| WO | WO-2004/080425 | | 9/2004 |
| WO | WO-2004/091375 | | 10/2004 |
| WO | WO-2005/048917 | | 6/2005 |
| WO | WO-2005/051307 | | 6/2005 |
| WO | WO-2005/090406 | A2 | 9/2005 |
| WO | WO-2006/008246 | A1 | 1/2006 |
| WO | WO-2006/082406 | A2 | 8/2006 |
| WO | WO-2007/130697 | A2 | 11/2007 |
| WO | WO-2008/042941 | A2 | 4/2008 |
| WO | WO-2008/112290 | | 9/2008 |

OTHER PUBLICATIONS

U.S. Appl. No. 12/156,553, filed Jun. 2, 2008, Krasnoperov et al.
Adams, R.H., et al., "Eph Receptors and Ephrin Ligands: Essential Mediators of Vascular Development," *Trends. Cardiovasc. Med.*, 10:183-188 (2000).
Adams, R.H., et al., "Roles of ephrinB ligands and EphB receptors in cardiovascular development: demarcation of arterial/venous domains, vascular morphogenesis, and sprouting angiogenesis," *Genes Dev.* 13:295-306 (1999).
Andres, A. C. et al., "Expression of two novel eph-related receptor protein tyrosine kinases in mammary gland development and carcinogenesis," *Oncogene*, 9:1461-1467 (1994).
Asahara, T. et al., "Isolation of Putative Progenitor Endothelial Cells for Angiogenesis," *Science*, 275:964-967 (1997).
Batlle, E., et al., "EphB receptor activity suppresses colorectal cancer progression," *Nature*, 435(23):1126-1130 (2005).
Bennett, B. D. et al., "Molecular cloning of a ligand for the EPH-related receptor protein-tyrosine kinase Htk," *Proc. Natl. Acad. Sci. USA*, 92:1866-1870 (1995).
Bennett, B.D., et al., "Cloning and Characterization of HTK, a Novel Transmembrane Tyrosine Kinase of the EPH Subfamily," *The Journal of Biological Chemistry*, 269(19): 14211-14218 (1994).
Berclaz, G., et al., "Activation of the receptor protein tyrosine kinase EphB4 in endometrial hyperplasia and endometrial carcinoma," Ann Oncol., 14:220-226 (2003).
Berclaz, G., et al., "Expression of the receptor protein tyrosine kinase myk-1/htk in normal and malignant mammary epithelium," Biochem Biophys Res Commun., 24;226:869-875 (1996).
Berclaz, G., et al., "Loss of EphB4 receptor tyrosine kinase protein expression during carcinogenesis of the human breast," Oncology Reports, 9(5):985-989, (2002).
Bergemann, A. D. et al., "ELF-2, a New Member of the Eph Ligand Family Is Segmentally Expressed in Mouse Embryos in the Region of the Hindbrain and Newly Forming Somites," *Molecular and Cellular Biology*, 15(9):4921-4929 (1995).
Bos et al., "PD153035, a Tyrosine Kinase Inhibitor, Prevents Epidermal Growth Factor Receptor Activation and Inhibitors Growth of Cancer Cells in a Receptor Number-dependent Manner," *Clinical Cancer Research*, 3:2099-2106 (1997).
Boyd, W.A., et al., "Isolation and Characterization of a Novel Receptor-type Protein Tyrosine Kinase (hek) from a Human Pre-B Cell Line," *The Journal of Biological Chemistry*, 267(5):3262-3267 (1992).
Brambilla, R., et al., "Membrane-bound LERK2 ligand can signal through three different Eph-related receptor tyrosine kinases," EMBO J., 14:3116-3126 (1995).
Brehmer et al., "Cellular Targets of Gefitinib," *Cancer Research*, 65(2):379-382 (2005).
Bruckner et al., "Tyrosine Phosphorylaton of Transmembrane Ligands for Eph Receptors," *Science*, 275:1640-1643 (1997).
Bruhl, T., et al., "Homeobox A9 Transcriptionally Regulates the EphB4 Receptor to Modulate Endothelial Cell Migration and Tube Formation," Circ. Res., 743-751 (2004) [Epub ahead of print] DOI 10.1161/01res0000120861.27064.09.
Caplen, N.J., "RNAI as a Gene Therapy Approach," Expert Opin. on Biol. Therapy, 3(4):575-586, (2003).
Carbone, M., et al., "The pathogenesis of mesothelioma," Semin. Oncol., 29(1):2-17 (2002).
Chang, M.W., et al., "AdenovirMediated Over-Expression of the Cyclin/Cyclin-Dependent Kinase Inhibitor, p21 Inhibits Vascular Smooth Muscle Cell Proliferation and Neointima Formation in the Rat Carotid Artery Model of Balloon Angioplasty," *J. Clin. Invest.*, 96:2260-2268 (1995).
Cheng, N., et al., "The ephrins and Eph receptors in angiogenesis," Cytokine & Growth Factor Reviews, 13:75-85 (2002).
Coffman, K.T., et al., "Differential EphA2 Epitope Display on Normal *versus* Malignant Cells," *Cancer Research*, 63:7907-7912 (2003).
Cowan, C.A., et al., "Ephrins in reverse, park and drive," Trends in Cell Biology, 12(7):339-346 (2002).
Cromer et al., "Identification of genes associated with tumorigenesis and metastatic potential of hypopharyngeal cancer by microarray analysis," Oncogene, Basingstoke, Hants, GB, 23(14):2484-2498, (2004).
Damschroder et al., "Framework shuffling of antibodies to reduce immunogenicity and manipulate functional and biophysical properties", Molecular Immunology, vol. 44(11), pp. 3049-3060 (2007).
Davis, S., et al., "Ligands for EPH-related receptor tyrosine kinases that require membrane attachment or clustering for activity," Science, 266(5186):816-819 (1994).

(56) References Cited

OTHER PUBLICATIONS

Dermer, G., "Another Anniversary for the War on Cancer," Bio/Technology, 12:320 (1994).

Dodelet, V.C. et al., "Eph Receptors and Ephrin Ligands: Embryogenesis to Tumorigenesis," Oncogene, 19(49): 5614-19 (2000).

Durbin, L., et al., "Eph signaling is required for segmentation and differentiation of the somites," Genes & Development, 12:3096-3109 (1998).

Easty et al., "Abnormal Protein Tyrosine Kinase Gene Expression During Melanoma Progression and Metastasis," Int. J. Cancer, 60:129-136 (1995).

Easty et al., "Cytokine B61 as a growth factor for metastatic melanomas and increasing expression of its receptor ECK during melanoma progression," Proceedings of the American Association for Cancer Research, 35(356) (1994) abstract only.

Easty, et al., "Expression of Eck and Lerk-1 During Melanoma Progression," P137 St. George's Hospital Medical School, London, JK and Western Infirmary, Glasgow, UK, Collection of the National Library of Medicine by a third party.

Fabes et al., "Accumulation of the Inhibitory Receptor EphA4 May Prevent Regeneration of Corticospinal Tract Axons Following Lesion," Eur. J. Neurosci. 23(7):1721-1730 (2006) (Abstract).

Feldman, L.J., et al., "Perspectives of Arterial Gene Therapy for the Prevention of Restenosis," Cardiovasc. Res., 32:194-207 (1996).

Folkman et al., "Angiogenic Factors," Science, 235:442-447 (1987).

Folkman, "Angiogenesis in cancer, vascular, rheumatoid and other disease," Nature Medicine, 1: 27-31, (1995).

Folkman, J. et al., "Blood Vessel Formation: What Is Its Molecular Basis?" Cell, 87:1153-1155 (1996).

Folkman, J., "Angiogenic Therapy of the Human Heart," Circulation, 97(7): 628-29 (1998).

Folkman, J., "Antiangiogenic Gene Therapy," Proc. Natl. Acad. Sci. USA., 95:9064-66 (1998).

Folkman, J., "Fighting Cancer by Attacking Its Blood Supply," Sci. Am., 275(3): 150-54 (1996).

Freshney, R. Ian, Culture of Animal Cells: A Manual of Basic Technique, pp. 3-4 (1983).

Fuller, T., et al., "Forward EphB4 signaling in endothelial cells controls cellular repulsion and segregation from ephrinB2 positive cells," J. Cell Sci., 6 (2003).

Gale, N.W. et al., "Growth Factors Acting via Endothelial Cell-Specific Receptor Tyrosine Kinases: VEGFs, Angiopoietins, and Ephrins in Vascular Development," Genes Dev., 13:1055-66 (1999).

Gale, N.W., et al., "Ephrin-B2 Selectively Marks Arterial Vessels and Neovascularization Sites in the Adult, with Expression in Both Endothelial and Smooth-Muscle Cells," Dev. Biol., 230: 151-160 (2001).

GenBank Acceisson No. P52803.

Gerety, S.S., et al., "Symmetrical mutant phenotypes of the receptor EphB4 and its specific transmembrane ligand ephrin-B2 in cardiovascular development," Mol. Cell, 4:403-414 (1999).

Glassberg et al., "Cultured endothelial cells derived from the human iliac arteries," In Vitro, 18:859-866 (1982).

Goetz et al., "Long-term serial cultivation of arterial and capillary endothelium from adult bovine brain," In Vitro Cellular and Developmental Biology, 21:172-180 (1985).

Gura, T., "Systems for Identifying New Drugs Are Often Faulty," Science 278:1041-1042.

Guzman, R.J., et al., "In Vivo Suppression of Injury-Induced Vascular Smooth Muscle Cell Accumulation Using AdenovirMediated Transfer of the Herpes Simplex Virus Thymidine Kinase Gene," Proc. Natl. Acad. Sci. USA, 91:10732-10736 (1994).

Hafner et al., "Differential Gene Expression of Eph Receptors and Ephrins in Benign Human Tissues and Cancers," Clinical Chemistry, 50(3):490-499 (2004).

Hafner, et al., "Loss of Eph B6 expression in metastatic melanoma," International Journal of Oncology, 23:1553-1559 (2003).

Hamada, K., Distinct roles of ephrin-B2 forward and EphB4 reverse signaling in endothelial cells, Arterioscler. Thromb. Vasc. Biol., 23:190-197 (2003).

Hausner, C., "Organogenesis Vascular Graft Becomes Physiologically-Responsive Living Tissue After Implantation [online]," Nature Biotechnol., (1999).

Henkemeyer, M., et al., "Nuk Controls Pathfinding of Commissural Axons in the Mammalian Central Nervous System," Cell, 86:35-46 (1996).

Himanen, J.P. et al., "Eph signaling: a structural view," Trends in Neurosciences, 26(1):46-51 (2003).

Himanen, J.P., et al., "Eph receptors and ephrins," Intl. J. Biochem. & Cell Bio., 35:130-134 (2003).

Hirai, H., "A novel putative tyrosine kinase receptor encoded by the eph gene," Science, 238:1717-1720 (1987).

Hollinger et al., "Diabodies": Small bivalent and bispecific antibody fragments, Proc. Natl. Acad. Sci. USA, vol. 90, pp. 6444-6448 (1993).

Inada et al., "Selective Expression of the Receptor Tyrosine Kinase, HTK, on Human Erythroid Progenitor Cells", Blood, 89(8), pp. 2757-2765 (1997).

Indolfi, C., et al., "Inhibition of Cellular ras Prevents Smooth Muscle Cell Proliferation After Vascular Injury In Vivo," Nature Med., 1(6):541-545 (1995).

Kenyon, B.M., et al., "A Model of Angiogenesis in the Mouse Cornea," Invest Ophthalmol. Vis. Sci., 37:1625-1632 (1996).

Keogh, M-C, et al., "Design of a Muscle Cell-Specific Expression Vector Utilising Human Vascular Smooth Muscle?—Actin Regulatory elements," Gene Therapy, 6:616-628 (1999).

Kitamura et al., "Chemical Engineering of the Monoclonal Antibody A7 by Polyethylene Glycol for Targeting Cancer Chemotherapy", Cancer Research, vol. 51, pp. 4310-4315 (1991).

Kiyokawa, E., et al., "Overexpression of ERK, an EPH family receptor protein tyrosine kinase, in various human tumors," Cancer Res., 54:3645-3650 (1994).

Kullander, K., et al., "Mechanisms and functions of eph and ephrin signalling," Nature Reviews, Molecular Cell Biology, 3:475-486 (2002).

Lackmann, et al., "Distinct Subdomains of the EphA3 Receptor Mediate Ligand Binding and Receptor Dimerization," The Journal of Biological Chemistry, 273 (32):20228-20237 (1998).

Li, J., et al., "Expression of the SM22α Promoter in Transgenic Mice Provides Evidence for Distinct Transcriptional Regulatory Programs in Vascular and Visceral Smooth Muscle Cells," J. Cell Biol., 132:849-59 (1996).

Lin, P., et al., "Antiangiogenic Gene Therapy Targeting the Endothelium-Specific Receptor Tyrosine Kinase Tie2," Proc. Natl. Acad. Sci., USA, 95:8829-8834 (1998).

Magal, et al., "B61, a Ligand for the Eck Receptor Protein-Tyrosine Kinase, Exhibits Neurotrophic Activity in Cultures of Rat Spinal Cord Neurons," Journal of Neuroscience Research, 43:735-744 (1996).

Maru, et al., "Evolution, Expression, and Chromosomal Location of a Novel Receptor Tyrosine Kinase Gene, eph," Molecular and Cellular Biology, 8(9):3770-3776 (1998).

Maru, et al., "Overexpression confers an oncogenic potential upon the eph gene," Oncogene, 5:445-447 (1990).

Mellitzer, G., et al., "Control of cell behavior by signalling through Eph receptors and ephrins," Neurobiology, 10:400-408 (2000).

Mellitzer, G., et al., "Eph Receptors and Ephrins Restrict Cell Intermingling and Communication," Nature, 400:77-82 (1999).

Miki et al., "Association of Ash/Grb-2 with Dynamin through the Src Homology 3 Domain", The Journal of Biological Chemistry, vol. 269(8); pp. 5489-5492 (1994).

Munarini, N., et al., "Altered mammary epithelial development, pattern formation and involution in transgenic mice expressing the EphB4 receptor tyrosine kinase," J. Cell Sci., 115(Pt 1):25-37 (2002).

Nakanuma, Y. et al., "Succinylated Wheat Germ Agglutinin Lectin Binding in Intrahepatic Vessels: A New Histochemical Tool," Arch. Pathol. Lab. Med., 117:809-811 (1993).

Niklason, L.E., et al., "Functional Arteries Grown in Vitro," Science, 284:489-493 (1999).

(56) References Cited

OTHER PUBLICATIONS

Niklason, L.E., et al., "Morphologic and Mechanical Characteristics of Engineered Bovine Arteries," *J. Vasc. Surg.*, 33:628-638 (2001).

Nikolova, et al., "Cell-type specific and estrogen dependent expression of the receptor tyrosine kinase EphB4 and its ligand ephrin-B2 during mammary gland morphogenesis," *Journal of Cell Science*, 111:2741-2751 (1998).

Nomura, A.M., et al., "Prostate cancer: a current perspective," Epidemiol Rev., 13:200-227 (1991).

Ogle et al., "The Role of Vascular Smooth Muscle Cell Integrins in the Compaction and Mechanical Strengthening of a Tissue-Engineered Blood Vessel," *Tissue Engineering*, 5(4):387-402 (1999).

Orioli, D., et al., "Sek4 and Nuk Receptors Cooperate in Guidance of Commissural Axons and in Palate Formation," *Embo J.*, 15(22):6035-6049.

Pandey et al., "Role of B61, the ligand for the eck receptor tyrosine kinase, in TNF-a-induced angiogenisis" *Science*, 268:567-569 (1996).

Parangi et al., "Antiangiogenic therapy of transgenic mice impairs de novo tumor growth," *Proc. Natl. Acad. Sci. USA*, 93:2002-2007 (1996).

Pasquale, E.B., "The Eph family of receptors," Curr. Opin. Cell Biol., 9:608-615 (1997).

Peng et al., "Regulation of Ca2+-activated K+ channels in pulmonary vascular smooth muscle cells: role of nitric oxide," *J. Applied Physiol.*, 81:1264-1272 (1996).

Presta et al., "Humanization of an Anti-Vascular Endothelial Growth Factor Monoclonal Antibody for the Therapy of Solid Tumors and Other Disorders," *Cancer Research*, 57:4593-4599 (1997).

Ramchandran et al., Mettaloprotease-mediated cleavage secretion of pulmonary ACE by vascular endothelial and kidney epithelial cells,: *Am. J. Physiology*, 271:H744-751 (1996).

Risau, W., "Mechanisms of angiogenesis," *Nature*, 386:671-674 (1997).

Sakano, S., et al., "Characterization of a ligand for receptor protein-tyrosine kinase HTK expressed in immature hematopoietic cells," Oncogene., 13:813-822 (1996).

Santa Cruz Biotechnology Inc datasheet for EphB4 (H-200): sc-5536.

Santa Cruz Biotechnology, Inc., "EphB4 (N-19): sc-7285", retrieved from the Internet: URL:http://www.genetimes.com.cn/support/pdf-ds/7200-7299/sc-7285.pdf (1999).

Schmucker, D., et al., "Signaling Downstream of Eph Receptors and Ephrin Ligands," Cell, 105:701-704 (2001).

Shepard, et al., "Monoclonal Antibody Therapy of Human Cancer: Taking the HER2 Protooncogene to the Clinic," *Journal of Clinical Immunology*, 11(3):117-127 (1991).

Shin, D., et al., "Expression of ephrinB2 identifies a stable genetic difference between arterial and venous vascular smooth muscle as well as endothelial cells, and marks subsets of microvessels at sites of adult neovascularization," Dev. Biol. 230:139-150 (2001).

Simonet, S., et al., "Venous and Arterial Endothelial Cells Respond Differently to Thrombin and its Endogenous Receptor Agonist," *European Journal of Pharmacology*, 216:135-137 (1992).

Simons, M., et al., "Antisense c-myb Oligonucleotides Inhibit Intimal Arterial Smooth Muscle Cell Accumulation In Vivo," *Nature*, 359(6390):67-70 (1992).

Sinha, et al., "Expression of EphB4 in head and neck squamous cell carcinoma" Ear, Nose and Throat Journal, 82(11), pp. 866, 869-870 & 887 (2003).

Sola et al. (Journal of Virology, May 1998, 3762-3772).

Stein, E. et al., "Eph receptors discriminate specific ligand oligomers to determine alternative signaling complexes, attachment, and assembly responses," *Genes & Development*, 12:667-678 (1998).

Stein, E. et al., "Nck Recruitment to Eph Receptor, EphB1/ELK, Couples Ligand Activation to c-Jun Kinase," *The Journal of Biological Chemistry*, 273(3):1303-1308 (1998).

Steinle, J.J., et al., "Eph B4 receptor signaling mediates endothelial cell migration and proliferation via the phosphatidylinositol 3-kinase pathway," J. Biol. Chem., 277(46):43830-5 (Nov. 15, 2002) (Epub Sep. 13, 2002).

Stephenson, S.A., et al., "Receptor protein tyrosine kinase EphB4 is up-regulated in colon cancer," BMC Mol. Biol., 2:15 (2001).

Sturz, et al., "EphB4 signaling is capable of mediating ephrinB2-induced inhibition of cell migration," *Biochemical and Biophysical Research Communications*, 313:80-88 (2004).

Sunassee, et al., "Tumour angiogenesis: Hitting cancer where it hurts," *Current Biology*, 7(5):R282-R285 (1997).

Takai, N., et al., "Expression of receptor tyrosine kinase EphB4 and its ligand ephrin-B2 is associated with malignant potential in endometrial cancer," Oncol Rep., 8:567-573 (2001).

Tallquist, M.D., et al., "Growth Factor Signaling Pathways in Vascular Development," *Oncogene*, 18(55):7917-7932 (1999).

Tang, X.X., et al., "Coexpression of transcripts encoding EphB receptor protein tyrosine kinases and their ephrin-B ligands in human small cell lung carcinoma," Clin. Cancer Res., 5:455-460 (1999).

The Eph Nomenclature Committee, "Unified Nomenclature for Eph Family Receptors and Their Ligands, the Ephrins," *Cell*, 90:403-404 (1997).

Thurston et al., "Permeability-related changes revealed at endothelial cell borders in inflamed venules by lectin binding," *American Journal of Physiology*, 271:H2547-H2562 (1996).

Tsui, L.V., et al., "p27-p16 Fusion Gene Inhibits Angioplasty-Induced Neointimal Hyperplasia and Coronary Artery Occlusion," *Circ. Res.*, 89:323-328 (2001).

Twardowski et al., "Clinical trials of antiangiogenic agents," *Current Opinion in Oncology*, 9:584-589 (1997).

van de Wiel et al., "Factors that define the susceptibility of endothelial cells to tumor necrosis factor and lipid A," *Immunopharmacology*, 23:49-56 (1992).

Vasgene Therapeutics, Inc., "Statement of Grounds of Opposition," In the Matter of European Patent No. 1135153 (EP-B-1135153), (2006).

Vector Laboratories, "Wheat Germ Agglutinin (WGA)," [online].

von der Leyen, H.E., et al., "Gene Therapy Inhibiting Neointimal Vascular Lesion: In Vivo Transfer of Endothelial Cell Nitric Oxide Synthase Gene," *Proc. Natl. Acad. Sci.*, 92:1137-1141 (1995).

Wang, H. U. et al., "Eph Family Transmembrane Ligands Can Mediate Repulsive Guidance of Trunk Neural Crest Migration and Motor Axon Outgrowth," *Neuron*, 18:383-396 (1997).

Wang, H.U., et al., "Molecular distinction and angiogenic interaction between embryonic arteries and veins revealed by ephrin-B2 and its receptor Eph-B4," Cell 93:741-753 (1998).

Waugh, J.M., et al., "Thrombomodulin Overexpression to Limit Neointima Formation," *Circulation*, 102:332-337 (2000).

Winlaw, "Angiogenesis in the Pathobiology and Treatment of Vascular and Malignant Diseases," *Ann. Thorac. Surg.*, 64:1204-1211 (1997).

Xia et al., "Up-Regulation of EphB4 in Mesothelioma and Its Biological Significance", Clinical Cancer Research, vol. 11(12), pp. 4305-4315 (2005).

Xu, et al., "Function of the Eph-related kinase rtk1 in patterning of the zebrafish forebrain," *Nature*, 381:19-322 (1996).

Yamamoto et al., "Differences in Cellular Responses to Mitogens in Arterial Smooth Muscle Cells Derived From Patients With Moyamoya Disease," *Stroke*, 29:1188-1193 (1998).

Yancopoulos, G. D. et al., "Vasculogenesis, Angiogenesis, and Growth Factors: Ephrins Enter the Fray at the Border," Cell, 93:661-664 (1998).

Yang et al., "Gene Targets of Antisense Therapies in Breast Cancer," Expert Opin. on Therapeutic Targets, 6(3):375-385, (2002).

Yuan, et al., "Syndecan-1 up-regulated by ephrinB2/EphB4 plays dual roles in inflammatory angiogenesis," *Blood*, 104(4):1025-1033 (2004).

Zetter, "Angiogenesis and Tumor Metastasis," *Annu. Rev. Med*, 49:407-424, (1998).

(56) References Cited

OTHER PUBLICATIONS

Zhang, X-Q, et al., "Stromal Cells Expressing ephrin-B2 Promote the Growth and Sprouting of Ephrin-B2+ Endothelial Cells," *Blood*, 98:1028-37 (2001).

Zhou, "The Eph Family Receptor and Ligands," *Pharmacol. Ther.*,77(3) 151-181 (1998).

Casadevall et al., Immunoglobulin isotype influences affinity and specificity, Proc. Natl. Acad. Sci. USA 109(31):12272-12273 (2012).

* cited by examiner

Figure 1

```
  1 melrvllcwa slaaaleetl lntkletadl kwvtfpqvdg qweelsglde eqhsvrtyev
 61 cdvqrapgqa hwlrtgwvpr rgavhvyatl rftmleclsl pragrscket ftvfyyesda
121 dtataltpaw menpyikvdt vaaehltrkr pgaeatgkvn vktlrlgpls kagfylafqd
181 qgacmallsl hlfykkcaql tvnltrfpet vprelvvpva gscvvdavpa pgpspslycr
241 edgqwaeqpv tgcscapgfe aaegntkcra caqgtfkpls gegscqpcpa nshsntigsa
301 vcqcrvgyfr artdprgapc ttppsaprsv vsrlngsslh lewsaplesg gredltyalr
361 crecrpggsc apcggdltfd pgprdlvepw vvvrglrpdf tytfevtaln gvsslatgpv
421 pfepvnvttd revppavsdi rvtrsspssl slawavprap sgavldyevk yhekgaegps
481 svrflktsen raelrglkrg asylvqvrar seagygpfgq ehhsqtqlde segwreqlal
541 iagtavvgvv lvlvvivvav lclrkqsngr eaeysdkhgq ylighgtkvy idpftyedpn
601 eavrefakei dvsyvkieev igagefgevc rgrlkapgkk escvaiktlk ggyterqrre
661 flseasimgq fehpniirle gvvtnsmpvm iltefmenga ldsflrlndg qftviqlvgm
721 lrgiasgmry laemsyvhrd laarnilvns nlvckvsdfg lsrfleenss dptytsslgg
781 kipirwtape aiafrkftsa sdawsygivm wevmsfgerp ywdmsnqdvi naieqdyrlp
841 pppdcptslh qlmldcwqkd rnarprfpqv vsaldkmirn paslkivare nggashplld
901 qrqphysafg svgewlraik mgryeesfaa agfgsfelvs qisaedllri gvtlaghqkk
961 ilasvqhmks qakpgtpggt ggpapqy
```

Figure 2A

```
SEQ ID NO:49   EVQLQQSGPELVKPGASVKISCKASGYTFTDYYMNWVKQSHGKGLEWIGDNNPNNGGTTYNQKFK
SEQ ID NO: 1   EVQLVQSGAELKKPGASVKISCKASGYTFTDYYMNWVKQAHGKGLEWIGDNNPNNGGTTYNQKFK
SEQ ID NO: 2   EVQLVQSGAELKKPGASVKISCKASGYTFTDYYMNWVKQAHGKGLEWIGDNNPNNGGTTYNQKFK
SEQ ID NO: 3   EVQLVQSGAEVKKPGASVKISCKASGYTFTDYYMNWVKQAPGKGLEWIGDNNPNNGGTTYNQKFK
SEQ ID NO: 4   EVQLVQSGAEVKKPGASVKVSCKASGYTFTDYYMNWVKQAPGKGLEWIGDNNPNNGGTTYNQKFK
SEQ ID NO: 5   EVQLVQSGAEVKKPGASVKVSCKASGYTFTDYYMNWVRQAPGKGLEWIGDNNPNNGGTTYNQKFK

SEQ ID NO:49   GKATLTVDKSSSTAYMELRSLTSEDSAVYYCARGKYYGTSYGWYFDVWGTGTTVTVSS
SEQ ID NO: 1   GRATLTVDKSTSTAYMELRSLRSEDSAVYYCARGKYYGTSYGWYFDVWGQGTTVTVSS
SEQ ID NO: 2   GRATLTVDKSTSTAYMELSSLRSEDSAVYYCARGKYYGTSYGWYFDVWGQGTTVTVSS
SEQ ID NO: 3   GRATLTVDKSTSTAYMELSSLRSEDTAVYYCARGKYYGTSYGWYFDVWGQGTTVTVSS
SEQ ID NO: 4   GRVTLTVDKSTSTAYMELSSLRSEDTAVYYCARGKYYGTSYGWYFDVWGQGTTVTVSS
SEQ ID NO: 5   GRVTITVDKSTSTAYMELSSLRSEDTAVYYCARGKYYGTSYGWYFDVWGQGTTVTVSS
```

Figure 2B

```
SEQ ID NO:50   DIQMTQSPASLSASVGETVTITCRISDNIDSYLAWFQQKQGKSPQLLVYDATVLADGVPSRFSGS
SEQ ID NO:6    DIQMTQSPSSLSASVGDRVTITCRISDNIDSYLAWFQQKQGKAPKLLVYDATVLADGVPSRFSGS
SEQ ID NO:7    DIQMTQSPSSLSASVGDRVTITCRISDNIDSYLAWFQQKPGKAPKLLVYDATVLADGVPSRFSGS
SEQ ID NO:8    DIQMTQSPSSLSASVGDRVTITCRISDNIDSYLAWFQQKPGKAPKLLVYDATVLADGVPSRFSGS
SEQ ID NO:9    DIQMTQSPSSLSASVGDRVTITCRISDNIDSYLAWYQQKPGKAPKLLVYDATVLADGVPSRFSGS

SEQ ID NO:50   GSGTQYSLKINSLQSEDAARYYCQVYYSIPWTFGGGTKLEIK
SEQ ID NO:6    GSGTQYTLTINSLQSEDAARYYCQVYYSIPWTFGQGTKLEIK
SEQ ID NO:7    GSGTDYTLTINSLQAEDAARYYCQVYYSIPWTFGQGTKLEIK
SEQ ID NO:8    GSGTDYTLTINSLQAEDAATYYCQVYYSIPWTFGQGTKLEIK
SEQ ID NO:9    GSGTDYTLTINSLQAEDAATYYCQVYYSIPWTFGQGTKLEIK
```

Figure 2C

```
SEQ ID NO:51   QVQLKQSGAELVKPGASVKISCKASGYTFTDYYINWVKQRPGQGLEWIGKIGPRIGTNYYNENFK
SEQ ID NO:10   QVQLVQSGAELKKPGASVKISCKASGYTFTDYYINWVKQAPGQGLEWIGKIGPRIGTNYYNENFK
SEQ ID NO:11   QVQLVQSGAEVKKPGASVKISCKASGYTFTDYYINWVKQAPGQGLEWIGKIGPRIGTNYYNENFK
SEQ ID NO:12   QVQLVQSGAEVKKPGASVKISCKASGYTFTDYYINWVKQAPGQGLEWIGKIGPRIGTNYYNENFK
SEQ ID NO:13   QVQLVQSGAEVKKPGASVKVSCKASGYTFTDYYINWVRQAPGQGLEWIGKIGPRIGTNYYNENFK
SEQ ID NO:14   QVQLVQSGAEVKKPGASVKVSCKASGYTFTDYYINWVRQAPGQGLEWIGKIGPRIGTNYYNENFK

SEQ ID NO:51   GKATLTADISSNTAYMQLHTLTSEDSAVYFCARSEDYSGYVSYALDYWGQGTSVTVSS
SEQ ID NO:10   GRATLTADISTNTAYMELSSLRSEDSAVYFCARSEDYSGYVSYALDYWGQGTSVTVSS
SEQ ID NO:11   GRATLTADISTNTAYMELSSLRSEDTAVYFCARSEDYSGYVSYALDYWGQGTLVTVSS
SEQ ID NO:12   GRVTLTADISTNTAYMELSSLRSEDTAVYYCARSEDYSGYVSYALDYWGQGTLVTVSS
SEQ ID NO:13   GRVTLTADISTNTAYMELSSLRSEDTAVYYCARSEDYSGYVSYALDYWGQGTLVTVSS
SEQ ID NO:14   GRVTLTADISTSTAYMELSSLRSEDTAVYYCARSEDYSGYVSYALDYWGQGTLVTVSS
```

Figure 2D

```
SEQ ID NO:52   NIVMTQSPKSMSMSVGERVTLSCKASENVDTYVSWYQQKPDQSPELLIYGASNRYTGVPDRFTGS
SEQ ID NO:15   NIVMTQSPASLSLSPGERVTLSCKASENVDTYVSWYQQKPDQSPKLLIYGASNRYTGVPDRFTGS
SEQ ID NO:16   NIVMTQSPATLSLSPGERVTLSCKASENVDTYVSWYQQKPDQSPKLLIYGASNRYTGVPDRFTGS
SEQ ID NO:17   NIVMTQSPATLSLSPGERVTLSCKASENVDTYVSWYQQKPDQSPKLLIYGASNRYTGVPDRFTGS
SEQ ID NO:18   NIVMTQSPATLSLSPGERVTLSCKASENVDTYVSWYQQKPDQSPKLLIYGASNRYTGVPDRFSGS

SEQ ID NO:52   GSATDFTLTISSVQAEDLADYHCGQTYRYPFTFGGGTKLEIK
SEQ ID NO:15   GSATDFTLTISSLQAEDVADYHCGQTYRYPFTFGQGTKVEIK
SEQ ID NO:16   GSATDFTLTISSLQAEDVADYHCGQTYRYPFTFGQGTKVEIK
SEQ ID NO:17   GSATDFTLTISSLQAEDVAVYYCGQTYRYPFTFGQGTKVEIK
SEQ ID NO:18   GSATDFTLTISSLQAEDVAVYYCGQTYRYPFTFGQGTKVEIK
```

| | 50% Binding (ng/ml) |
|---|---|
| Chimeric 47 | 2 |
| 3/8 | 1.8 |
| 4/7 | 2 |
| 4/8 | 2.8 |
| 3/7 | 3.3 |

SEQUENCE LISTING

```
<160> NUMBER OF SEQ ID NOS: 53

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Gln Ser Gly Ala Glu Leu Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ala His Gly Lys Gly Leu Glu Trp Ile
        35                  40                  45

Gly Asp Asn Asn Pro Asn Asn Gly Gly Thr Thr Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Glu Asp Ser Ala Val Tyr Tyr Cys
                85                  90                  95

Ala Arg Gly Lys Tyr Tyr Gly Thr Ser Tyr Gly Trp Tyr Phe Asp Val
            100                 105                 110

Trp Gly Gln Gly Thr Thr Val Thr Val Ser Ser
        115                 120

<210> SEQ ID NO 2
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Gln Ser Gly Ala Glu Leu Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ala His Gly Lys Gly Leu Glu Trp Ile
        35                  40                  45

Gly Asp Asn Asn Pro Asn Asn Gly Gly Thr Thr Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Ser Ala Val Tyr Tyr Cys
                85                  90                  95
```

-continued

Ala Arg Gly Lys Tyr Tyr Gly Thr Ser Tyr Gly Trp Tyr Phe Asp Val
            100                 105                 110

Trp Gly Gln Gly Thr Thr Val Thr Val Ser Ser
        115                 120

<210> SEQ ID NO 3
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ala Pro Gly Lys Gly Leu Glu Trp Ile
        35                  40                  45

Gly Asp Asn Asn Pro Asn Asn Gly Gly Thr Thr Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Tyr Gly Thr Ser Tyr Gly Trp Tyr Phe Asp Val
            100                 105                 110

Trp Gly Gln Gly Thr Thr Val Thr Val Ser Ser
        115                 120

<210> SEQ ID NO 4
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Lys Gln Ala Pro Gly Lys Gly Leu Glu Trp Ile
        35                  40                  45

Gly Asp Asn Asn Pro Asn Asn Gly Gly Thr Thr Tyr Asn Gln Lys Phe
    50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Tyr Gly Thr Ser Tyr Gly Trp Tyr Phe Asp Val
            100                 105                 110

Trp Gly Gln Gly Thr Thr Val Thr Val Ser Ser
        115                 120

<210> SEQ ID NO 5
<211> LENGTH: 123

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Lys Gly Leu Glu Trp Ile
            35                  40                  45

Gly Asp Asn Asn Pro Asn Asn Gly Gly Thr Thr Tyr Asn Gln Lys Phe
        50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Lys Tyr Tyr Gly Thr Ser Tyr Gly Tyr Trp Tyr Phe Asp Val
                100                 105                 110

Trp Gly Gln Gly Thr Thr Val Thr Val Ser Ser
            115                 120

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ile Ser Asp Asn Ile Asp Ser Tyr
                20                  25                  30

Leu Ala Trp Phe Gln Gln Lys Gln Gly Lys Ala Pro Lys Leu Leu Val
            35                  40                  45

Tyr Asp Ala Thr Val Leu Ala Asp Gly Val Pro Ser Arg Phe Ser Gly
        50                  55                  60

Ser Gly Ser Gly Thr Asp Tyr Thr Leu Thr Ile Asn Ser Leu Gln Ser
65                  70                  75                  80

Glu Asp Ala Ala Arg Tyr Tyr Cys Gln Val Tyr Tyr Ser Ile Pro Trp
                85                  90                  95

Thr Phe Gly Gln Gly Thr Lys Leu Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ile Ser Asp Asn Ile Asp Ser Tyr
```

```
                     20                  25                  30

Leu Ala Trp Phe Gln Gln Lys Pro Gly Lys Ala Pro Lys Leu Leu Val
            35                  40                  45

Tyr Asp Ala Thr Val Leu Ala Asp Gly Val Pro Ser Arg Phe Ser Gly
 50                  55                  60

Ser Gly Ser Gly Thr Asp Tyr Thr Leu Thr Ile Asn Ser Leu Gln Ala
 65                  70                  75                  80

Glu Asp Ala Ala Arg Tyr Tyr Cys Gln Val Tyr Tyr Ser Ile Pro Trp
                 85                  90                  95

Thr Phe Gly Gln Gly Thr Lys Leu Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Arg Ile Ser Asp Asn Ile Asp Ser Tyr
                 20                  25                  30

Leu Ala Trp Phe Gln Gln Lys Pro Gly Lys Ala Pro Lys Leu Leu Val
            35                  40                  45

Tyr Asp Ala Thr Val Leu Ala Asp Gly Val Pro Ser Arg Phe Ser Gly
 50                  55                  60

Ser Gly Ser Gly Thr Asp Tyr Thr Leu Thr Ile Asn Ser Leu Gln Ala
 65                  70                  75                  80

Glu Asp Ala Ala Thr Tyr Tyr Cys Gln Val Tyr Tyr Ser Ile Pro Trp
                 85                  90                  95

Thr Phe Gly Gln Gly Thr Lys Leu Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
 1               5                  10                  15

Asp Arg Val Thr Ile Thr Cys Arg Ile Ser Asp Asn Ile Asp Ser Tyr
                 20                  25                  30

Leu Ala Trp Tyr Gln Gln Lys Pro Gly Lys Ala Pro Lys Leu Leu Val
            35                  40                  45

Tyr Asp Ala Thr Val Leu Ala Asp Gly Val Pro Ser Arg Phe Ser Gly
 50                  55                  60

Ser Gly Ser Gly Thr Asp Tyr Thr Leu Thr Ile Asn Ser Leu Gln Ala
 65                  70                  75                  80

Glu Asp Ala Ala Thr Tyr Tyr Cys Gln Val Tyr Tyr Ser Ile Pro Trp
                 85                  90                  95

Thr Phe Gly Gln Gly Thr Lys Leu Glu Ile Lys
```

<210> SEQ ID NO 10
<211> LENGTH: 123
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

Gln Val Gln Leu Val Gln Ser Gly Ala Glu Leu Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Ala Pro Gly Gln Gly Leu Glu Trp Ile
        35                  40                  45

Gly Lys Ile Gly Pro Arg Ile Gly Thr Asn Tyr Tyr Asn Glu Asn Phe
    50                  55                  60

Lys Gly Arg Ala Thr Leu Thr Ala Asp Ile Ser Thr Asn Thr Ala Tyr
65                  70                  75                  80

Met Glu Leu Ser Ser Leu Arg Ser Glu Asp Ser Ala Val Tyr Phe Cys
                85                  90                  95

Ala Arg Ser Glu Asp Tyr Ser Gly Tyr Val Ser Tyr Ala Leu Asp Tyr
            100                 105                 110

Trp Gly Gln Gly Thr Ser Val Thr Val Ser Ser
        115                 120

<210> SEQ ID NO 11
<211> LENGTH: 123
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 11

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Ala Pro Gly Gln Gly Leu Glu Trp Ile
        35                  40                  45

Gly Lys Ile Gly Pro Arg Ile Gly Thr Asn Tyr Tyr Asn Glu Asn Phe
    50                  55                  60

Lys Gly Arg Ala Thr Leu Thr Ala Asp Ile Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Arg Ser Glu Asp Tyr Ser Gly Tyr Val Ser Tyr Ala Leu Asp Tyr
            100                 105                 110

Trp Gly Gln Gly Thr Leu Val Thr Val Ser Ser
        115                 120

<210> SEQ ID NO 12
<211> LENGTH: 123
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 12

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Ala Pro Gly Gln Gly Leu Glu Trp Ile
        35                  40                  45

Gly Lys Ile Gly Pro Arg Ile Gly Thr Asn Tyr Tyr Asn Glu Asn Phe
    50                  55                  60

Lys Gly Arg Val Thr Leu Thr Ala Asp Ile Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Asp Tyr Ser Gly Tyr Val Ser Tyr Ala Leu Asp Tyr
            100                 105                 110

Trp Gly Gln Gly Thr Leu Val Thr Val Ser Ser
        115                 120

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Ile
        35                  40                  45

Gly Lys Ile Gly Pro Arg Ile Gly Thr Asn Tyr Tyr Asn Glu Asn Phe
    50                  55                  60

Lys Gly Arg Val Thr Leu Thr Ala Asp Ile Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Glu Asp Tyr Ser Gly Tyr Val Ser Tyr Ala Leu Asp Tyr
            100                 105                 110

Trp Gly Gln Gly Thr Leu Val Thr Val Ser Ser
        115                 120

<210> SEQ ID NO 14
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Ile
                35                  40                  45

Gly Lys Ile Gly Pro Arg Ile Gly Thr Asn Tyr Tyr Asn Glu Asn Phe
 50                  55                  60

Lys Gly Arg Val Thr Leu Thr Ala Asp Ile Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Glu Asp Tyr Ser Gly Tyr Val Ser Tyr Ala Leu Asp Tyr
                100                 105                 110

Trp Gly Gln Gly Thr Leu Val Thr Val Ser Ser
                115                 120

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asn Ile Val Met Thr Gln Ser Pro Ala Ser Leu Ser Leu Ser Pro Gly
 1               5                   10                  15

Glu Arg Val Thr Leu Ser Cys Lys Ala Ser Glu Asn Val Asp Thr Tyr
                20                  25                  30

Val Ser Trp Tyr Gln Gln Lys Pro Asp Gln Ser Pro Lys Leu Leu Ile
                35                  40                  45

Tyr Gly Ala Ser Asn Arg Tyr Thr Gly Val Pro Asp Arg Phe Thr Gly
 50                  55                  60

Ser Gly Ser Ala Thr Asp Phe Thr Leu Thr Ile Ser Ser Leu Gln Ala
 65                  70                  75                  80

Glu Asp Val Ala Asp Tyr His Cys Gly Gln Thr Tyr Arg Tyr Pro Phe
                85                  90                  95

Thr Phe Gly Gln Gly Thr Lys Val Glu Ile Lys
                100                 105

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asn Ile Val Met Thr Gln Ser Pro Ala Thr Leu Ser Leu Ser Pro Gly
 1               5                   10                  15

Glu Arg Val Thr Leu Ser Cys Lys Ala Ser Glu Asn Val Asp Thr Tyr
                20                  25                  30

Val Ser Trp Tyr Gln Gln Lys Pro Asp Gln Ser Pro Lys Leu Leu Ile
                35                  40                  45

Tyr Gly Ala Ser Asn Arg Tyr Thr Gly Val Pro Asp Arg Phe Thr Gly
 50                  55                  60

Ser Gly Ser Ala Thr Asp Phe Thr Leu Thr Ile Ser Ser Leu Gln Ala
 65                  70                  75                  80

Glu Asp Val Ala Asp Tyr His Cys Gly Gln Thr Tyr Arg Tyr Pro Phe
                85                  90                  95

```
Thr Phe Gly Gln Gly Thr Lys Val Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asn Ile Val Met Thr Gln Ser Pro Ala Thr Leu Ser Leu Ser Pro Gly
1               5                   10                  15

Glu Arg Val Thr Leu Ser Cys Lys Ala Ser Glu Asn Val Asp Thr Tyr
            20                  25                  30

Val Ser Trp Tyr Gln Gln Lys Pro Asp Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Leu Gln Ala
65                  70                  75                  80

Glu Asp Val Ala Val Tyr Tyr Cys Gly Gln Thr Tyr Arg Tyr Pro Phe
                85                  90                  95

Thr Phe Gly Gln Gly Thr Lys Val Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asn Ile Val Met Thr Gln Ser Pro Ala Thr Leu Ser Leu Ser Pro Gly
1               5                   10                  15

Glu Arg Val Thr Leu Ser Cys Lys Ala Ser Glu Asn Val Asp Thr Tyr
            20                  25                  30

Val Ser Trp Tyr Gln Gln Lys Pro Asp Gln Ser Pro Lys Leu Leu Ile
        35                  40                  45

Tyr Gly Ala Ser Asn Arg Tyr Thr Gly Val Pro Asp Arg Phe Ser Gly
    50                  55                  60

Ser Gly Ser Ala Thr Asp Phe Thr Leu Thr Ile Ser Ser Leu Gln Ala
65                  70                  75                  80

Glu Asp Val Ala Val Tyr Tyr Cys Gly Gln Thr Tyr Arg Tyr Pro Phe
                85                  90                  95

Thr Phe Gly Gln Gly Thr Lys Val Glu Ile Lys
            100                 105

<210> SEQ ID NO 19
<211> LENGTH: 5
<212> TYPE: PRT
<213> ORGANISM: Mus sp.

<400> SEQUENCE: 19

Asp Tyr Tyr Met Asn
1               5
```

<210> SEQ ID NO 20
<211> LENGTH: 15
<212> TYPE: PRT
<213> ORGANISM: Mus sp.

<400> SEQUENCE: 20

Asp Asn Asn Pro Asn Asn Gly Gly Thr Thr Tyr Asn Gln Lys Phe
1               5                   10                  15

<210> SEQ ID NO 21
<211> LENGTH: 14
<212> TYPE: PRT
<213> ORGANISM: Mus sp.

<400> SEQUENCE: 21

Gly Lys Tyr Tyr Gly Thr Ser Tyr Gly Trp Tyr Phe Asp Val
1               5                   10

<210> SEQ ID NO 22
<211> LENGTH: 11
<212> TYPE: PRT
<213> ORGANISM: Mus sp.

<400> SEQUENCE: 22

Arg Ile Ser Asp Asn Ile Asp Ser Tyr Leu Ala
1               5                   10

<210> SEQ ID NO 23
<211> LENGTH: 7
<212> TYPE: PRT
<213> ORGANISM: Mus sp.

<400> SEQUENCE: 23

Asp Ala Thr Val Leu Ala Asp
1               5

<210> SEQ ID NO 24
<211> LENGTH: 9
<212> TYPE: PRT
<213> ORGANISM: Mus sp.

<400> SEQUENCE: 24

Gln Val Tyr Tyr Ser Ile Pro Trp Thr
1               5

<210> SEQ ID NO 25
<211> LENGTH: 5
<212> TYPE: PRT
<213> ORGANISM: Mus sp.

<400> SEQUENCE: 25

Asp Tyr Tyr Ile Asn
1               5

<210> SEQ ID NO 26
<211> LENGTH: 16
<212> TYPE: PRT
<213> ORGANISM: Mus sp.

<400> SEQUENCE: 26

Lys Ile Gly Pro Arg Ile Gly Thr Asn Tyr Tyr Asn Glu Asn Phe Lys
1               5                   10                  15

<210> SEQ ID NO 27

```
<211> LENGTH: 14
<212> TYPE: PRT
<213> ORGANISM: Mus sp.

<400> SEQUENCE: 27

Ser Glu Asp Tyr Ser Gly Tyr Val Ser Tyr Ala Leu Asp Tyr
1               5                   10

<210> SEQ ID NO 28
<211> LENGTH: 11
<212> TYPE: PRT
<213> ORGANISM: Mus sp.

<400> SEQUENCE: 28

Lys Ala Ser Glu Asn Val Asp Thr Tyr Val Ser
1               5                   10

<210> SEQ ID NO 29
<211> LENGTH: 7
<212> TYPE: PRT
<213> ORGANISM: Mus sp.

<400> SEQUENCE: 29

Gly Ala Ser Asn Arg Tyr Thr
1               5

<210> SEQ ID NO 30
<211> LENGTH: 9
<212> TYPE: PRT
<213> ORGANISM: Mus sp.

<400> SEQUENCE: 30

Gly Gln Thr Tyr Arg Tyr Pro Phe Thr
1               5

<210> SEQ ID NO 31
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaggtccagc tggtgcagtc tggagctgag ctgaagaagc ctggggcttc agtgaagata      60
tcctgtaagg cttctggata cacgttcact gactactaca tgaactgggt gaaacaggca     120
catggaaagg gacttgagtg gattggagat aataatccta ataatggtgg tactaactac     180
aaccagaagt tcaagggcag ggccacattg actgtagaca gtccaccag cacagcctac      240 atggagctcc gcagcctgcg atctgaggac tctgcagtct attactgtgc aagaggaaaa     300
tactacggta ctagctacgg ctggtacttc gatgtctggg gccaagggac cacggtcacc     360
gtctcctca                                                             369

<210> SEQ ID NO 32
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gaggtccagc tggtgcagtc tggagctgag ctgaagaagc ctggggcttc agtgaagata      60
```

```
tcctgtaagg cttctggata cacgttcact gactactaca tgaactgggt gaaacaggca    120
catggaaagg gacttgagtg gattggagat aataatccta ataatggtgg tactaactac    180
aaccagaagt tcaagggcag ggccacattg actgtagaca agtccaccag cacagcctac    240
atggagctca gcagcctgcg atctgaggac tctgcagtct attactgtgc aagaggaaaa    300
tactacggta ctagctacgg ctggtacttc gatgtctggg gccaagggac cacggtcacc    360
gtctcctca                                                            369
```

<210> SEQ ID NO 33
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
gaggtccagc tggtgcagtc tggagctgag gtgaagaagc ctggggcttc agtgaagata     60
tcctgtaagg cttctggata cacgttcact gactactaca tgaactgggt gaaacaggca    120
cctggaaagg gacttgagtg gattggagat aataatccta ataatggtgg tactaactac    180
aaccagaagt tcaagggcag ggccacattg actgtagaca agtccaccag cacagcctac    240
atggagctca gcagcctgcg atctgaggac actgcagtct attactgtgc aagaggaaaa    300
tactacggta ctagctacgg ctggtacttc gatgtctggg gccaagggac cacggtcacc    360
gtctcctca                                                            369
```

<210> SEQ ID NO 34
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
gaggtccagc tggtgcagtc tggagctgag gtgaagaagc ctggggcttc agtgaaggta     60
tcctgtaagg cttctggata cacgttcact gactactaca tgaactgggt gaaacaggca    120
cctggaaagg gacttgagtg gattggagat aataatccta ataatggtgg tactaactac    180
aaccagaagt tcaagggcag ggtcacattg actgtagaca agtccaccag cacagcctac    240
atggagctca gcagcctgcg atctgaggac actgcagtct attactgtgc aagaggaaaa    300
tactacggta ctagctacgg ctggtacttc gatgtctggg gccaagggac cacggtcacc    360
gtctcctca                                                            369
```

<210> SEQ ID NO 35
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
gaggtccagc tggtgcagtc tggagctgag gtgaagaagc ctggggcttc agtgaaggta     60
tcctgtaagg cttctggata cacgttcact gactactaca tgaactgggt gagacaggca    120
cctggaaagg gacttgagtg gattggagat aataatccta ataatggtgg tactaactac    180
```

```
aaccagaagt tcaagggcag ggtcacaatt actgtagaca agtccaccag cacagcctac    240
atggagctca gcagcctgcg atctgaggac actgcagtct attactgtgc aagaggaaaa    300
tactacggta ctagctacgg ctggtacttc gatgtctggg gccaagggac cacggtcacc    360
gtctcctca                                                            369
```

```
<210> SEQ ID NO 36
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gacatccaga tgactcagtc tccatcttcc ctgtctgcat ctgtgggaga ccgtgtcacc     60
atcacatgtc gaataagtga caatattgac agttatttag catggtttca gcagaaacag    120
ggaaaagctc ctaagctcct ggtctatgat gcaacagtct tagcagatgg tgtgccatca    180
aggttcagtg gcagtggatc aggcacacag tatactctca cgatcaacag cctgcagtct    240
gaagatgctg cgagatatta ctgtcaagtt tattatagta ttccgtggac gttcggtcaa    300
ggcaccaagc tggaaatcaa a                                              321
```

```
<210> SEQ ID NO 37
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gacatccaga tgactcagtc tccatcttcc ctgtctgcat ctgtgggaga ccgtgtcacc     60
atcacatgtc gaataagtga caatattgac agttatttag catggtttca gcagaaaccg    120
ggaaaagctc ctaagctcct ggtctatgat gcaacagtct tagcagatgg tgtgccatca    180
aggttcagtg gcagtggatc aggcacagac tatactctca cgatcaacag cctgcaggct    240
gaagatgctg cgagatatta ctgtcaagtt tattatagta ttccgtggac gttcggtcaa    300
ggcaccaagc tggaaatcaa a                                              321
```

```
<210> SEQ ID NO 38
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gacatccaga tgactcagtc tccatcttcc ctgtctgcat ctgtgggaga ccgtgtcacc     60
atcacatgtc gaataagtga caatattgac agttatttag catggtttca gcagaaaccg    120
ggaaaagctc ctaagctcct ggtctatgat gcaacagtct tagcagatgg tgtgccatca    180
aggttcagtg gcagtggatc aggcacagac tatactctca cgatcaacag cctgcaggct    240
gaagatgctg cgacatatta ctgtcaagtt tattatagta ttccgtggac gttcggtcaa    300
ggcaccaagc tggaaatcaa a                                              321
```

```
<210> SEQ ID NO 39
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gacatccaga tgactcagtc tccatcttcc ctgtctgcat ctgtgggaga ccgtgtcacc    60
atcacatgtc gaataagtga caatattgac agttatttag catggtatca gcagaaaccg   120
ggaaaagctc ctaagctcct ggtctatgat gcaacagtct tagcagatgg tgtgccatca   180
aggttcagtg gcagtggatc aggcacagac tatactctca cgatcaacag cctgcaggct   240
gaagatgctg cgacatatta ctgtcaagtt tattatagta ttccgtggac gttcggtcaa   300
ggcaccaagc tggaaatcaa a                                              321

<210> SEQ ID NO 40
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
caggtccagc tggtgcagtc tggagctgag ctgaagaagc ctggggcttc agtgaagatt    60
tcctgcaagg cttctggcta caccttcact gactactaca ttaactgggt gaagcaggcg   120
cctggacagg gccttgagtg gattggcaag attggtcctc gaattggtac taattactac   180
aatgaaaact caagggcag ggccacactg actgcagaca tttccaccaa cacagcctac    240
atggagctct cctccctgag atctgaggac tctgctgtct atttctgtgc aagatctgag   300
gactactctg gttatgtttc ctatgcttta gactactggg gtcaaggaac ctccgtcacc   360
gtctcctca                                                            369

<210> SEQ ID NO 41
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caggtccagc tggtgcagtc tggagctgag gtgaagaagc ctggggcttc agtgaagatt    60
tcctgcaagg cttctggcta caccttcact gactactaca ttaactgggt gaagcaggcg   120
cctggacagg gccttgagtg gattggcaag attggtcctc gaattggtac taattactac   180
aatgaaaact caagggcag ggccacactg actgcagaca tttccaccaa cacagcctac    240
atggagctct cctccctgag atctgaggac actgctgtct atttctgtgc aagatctgag   300
gactactctg gttatgtttc ctatgcttta gactactggg gtcaaggaac cctcgtcacc   360
gtctcctca                                                            369

<210> SEQ ID NO 42
<211> LENGTH: 369
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 42
caggtccagc tggtgcagtc tggagctgag gtgaagaagc ctggggcttc agtgaagatt      60
tcctgcaagg cttctggcta caccttcact gactactaca ttaactgggt gaagcaggcg     120
cctggacagg gccttgagtg gattggcaag attggtcctc gaattggtac taattactac     180
aatgaaaact tcaagggcag ggtcacactg actgcagaca tttccaccaa cacagcctac     240
atggagctct cctccctgag atctgaggac actgctgtct attactgtgc aagatctgag     300
gactactctg gttatgtttc ctatgcttta gactactggg gtcaaggaac cctcgtcacc     360
gtctcctca                                                              369

<210> SEQ ID NO 43
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
caggtccagc tggtgcagtc tggagctgag gtgaagaagc ctggggcttc agtgaaggtt      60
tcctgcaagg cttctggcta caccttcact gactactata ttaactgggt gaggcaggcg     120
cctggacagg gccttgagtg gattggcaag attggtcctc gaattggtac taattactac     180
aatgaaaact tcaagggcag ggtcacactg actgcagaca tttccaccaa cacagcctac     240
atggagctct cctccctgag atctgaggac actgctgtct attactgtgc aagatctgag     300
gactactctg gttatgtttc ctatgcttta gactactggg gtcaaggaac cctcgtcacc     360
gtctcctca                                                              369

<210> SEQ ID NO 44
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caggtccagc tggtgcagtc tggagctgag gtgaagaagc ctggggcttc agtgaaggtt      60
tcctgcaagg cttctggcta caccttcact gactactaca ttaactgggt gaggcaggcg     120
cctggacagg gccttgagtg gattggcaag attggtcctc gaattggtac taattactac     180
aatgaaaact tcaagggcag ggtcacactg actgcagaca tttccaccag cacagcctac     240
atggagctct cctccctgag atctgaggac actgctgtct attactgtgc aagatctgag     300
gactactctg gttatgtttc ctatgcttta gactactggg gtcaaggaac cctcgtcacc     360
gtctcctca                                                              369

<210> SEQ ID NO 45
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
```

```
aacattgtaa tgacccaatc tcccgcatcc ctgtccctgt caccaggaga gagggtcacc    60
ttgagctgca aggccagtga gaatgtggat acttatgtat cctggtatca acagaaacca   120
gaccagtctc ctaaattgct aatttacggg gcatccaacc ggtacactgg agtccctgat   180
cgcttcacag gcagtggatc tgcaacagat ttcactctga ccatcagcag tcttcaggct   240
gaagacgttg cagattatca ctgtggacag acttacaggt atccgttcac gttcggacag   300
gggaccaagg tggaaataaa a                                             321

<210> SEQ ID NO 46
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
aacattgtaa tgacccaatc tcccgcaacc ctgtccctgt caccaggaga gagggtcacc    60
ttgagctgca aggccagtga gaatgtggat acttatgtat cctggtatca acagaaacca   120
gaccagtctc ctaaattgct aatttacggg gcatccaacc ggtacactgg agtccctgat   180
cgcttcacag gcagtggatc tgcaacagat ttcactctga ccatcagcag tcttcaggct   240
gaagacgttg cagattatca ctgtggacag acttacaggt atccgttcac gttcggacag   300
gggaccaagg tggaaataaa a                                             321

<210> SEQ ID NO 47
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
aacattgtaa tgacccaatc tcccgcaacc ctgtccctgt caccaggaga gagggtcacc    60
ttgagctgca aggccagtga gaatgtggat acttatgtat cctggtatca acagaaacca   120
gaccagtctc ctaaattgct aatttacggg gcatccaacc ggtacactgg agtccctgat   180
cgcttcacag gcagtggatc tgcaacagat ttcactctga ccatcagcag tcttcaggct   240
gaagacgttg cagtttatta ctgtggacag acttacaggt atccgttcac gttcggacag   300
gggaccaagg tggaaataaa a                                             321

<210> SEQ ID NO 48
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
aacattgtaa tgacccaatc tcccgcaacc ctgtccctgt caccaggaga gagggtcacc    60
ttgagctgca aggccagtga gaatgtggat acttatgtat cctggtatca acagaaacca   120
gaccagtctc ctaaattgct aatttacggg gcatccaacc ggtacactgg agtccctgat   180
cgcttctcag gcagtggatc tgcaacagat ttcactctga ccatcagcag tcttcaggct   240
gaagacgttg cagtttatta ctgtggacag acttacaggt atccgttcac gttcggacag   300
```
gggaccaagg tggaaataaa a                                                     321

<210> SEQ ID NO 49
<211> LENGTH: 123
<212> TYPE: PRT
<213> ORGANISM: Mus sp.

<400> SEQUENCE: 49

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Gly Leu Glu Trp Ile
        35                  40                  45

Gly Asp Asn Asn Pro Asn Asn Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Lys Tyr Tyr Gly Thr Ser Tyr Gly Trp Tyr Phe Asp Val
            100                 105                 110

Trp Gly Thr Gly Thr Thr Val Thr Val Ser Ser
        115                 120

<210> SEQ ID NO 50
<211> LENGTH: 107
<212> TYPE: PRT
<213> ORGANISM: Mus sp.

<400> SEQUENCE: 50

Asp Ile Gln Met Thr Gln Ser Pro Ala Ser Leu Ser Ala Ser Val Gly
1               5                   10                  15

Glu Thr Val Thr Ile Thr Cys Arg Ile Ser Asp Asn Ile Asp Ser Tyr
            20                  25                  30

Leu Ala Trp Phe Gln Gln Lys Gln Gly Lys Ser Pro Gln Leu Leu Val
        35                  40                  45

Tyr Asp Ala Thr Val Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Ala Ala Arg Tyr Tyr Cys Gln Val Tyr Tyr Ser Ile Pro Trp
                85                  90                  95

Thr Phe Gly Gly Gly Thr Lys Leu Glu Ile Lys
            100                 105

<210> SEQ ID NO 51
<211> LENGTH: 123
<212> TYPE: PRT
<213> ORGANISM: Mus sp.

<400> SEQUENCE: 51

Gln Val Gln Leu Lys Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Lys Ile Gly Pro Arg Ile Gly Thr Asn Tyr Tyr Asn Glu Asn Phe
            50                  55                  60

Lys Gly Lys Ala Thr Leu Thr Ala Asp Ile Ser Ser Asn Thr Ala Tyr
 65                  70                  75                  80

Met Gln Leu His Thr Leu Thr Ser Glu Asp Ser Ala Val Tyr Phe Cys
                85                  90                  95

Ala Arg Ser Glu Asp Tyr Ser Gly Tyr Val Ser Tyr Ala Leu Asp Tyr
                100                 105                 110

Trp Gly Gln Gly Thr Ser Val Thr Val Ser Ser
            115                 120

<210> SEQ ID NO 52
<211> LENGTH: 107
<212> TYPE: PRT
<213> ORGANISM: Mus sp.

<400> SEQUENCE: 52

Asn Ile Val Met Thr Gln Ser Pro Lys Ser Met Ser Met Ser Val Gly
  1               5                  10                  15

Glu Arg Val Thr Leu Ser Cys Lys Ala Ser Glu Asn Val Asp Thr Tyr
                20                  25                  30

Val Ser Trp Tyr Gln Gln Lys Pro Asp Gln Ser Pro Glu Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Ser Tyr Arg Tyr Pro Phe
                85                  90                  95

Thr Phe Gly Gly Gly Thr Lys Leu Glu Ile Lys
                100                 105

<210> SEQ ID NO 53
<211> LENGTH: 987
<212> TYPE: PRT
<213> ORGANISM: Homo sapiens

<400> SEQUENCE: 53

Met Glu Leu Arg Val Leu Leu Cys Trp Ala Ser Leu Ala Ala Ala Leu
  1               5                  10                  15

Glu Glu Thr Leu Leu Asn Thr Lys Leu Glu Thr Ala Asp Leu Lys Trp
                20                  25                  30

Val Thr Phe Pro Gln Val Asp Gly Gln Trp Glu Glu Leu Ser Gly Leu
            35                  40                  45

Asp Glu Glu Gln His Ser Val Arg Thr Tyr Glu Val Cys Asp Val Gln
        50                  55                  60

Arg Ala Pro Gly Gln Ala His Trp Leu Arg Thr Gly Trp Val Pro Arg
 65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
                100                 105                 110

Val Phe Tyr Tyr Glu Ser Asp Ala Asp Thr Ala Thr Ala Leu Thr Pro
            115                 120                 125

Ala Trp Met Glu Asn Pro Tyr Ile Lys Val Asp Thr Val Ala Ala Glu
        130                 135                 140

```
His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
            165                 170                 175

Ala Phe Gln Asp Gln Gly Ala Cys Met Ala Leu Leu Ser Leu His Leu
        180                 185                 190

Phe Tyr Lys Lys Cys Ala Gln Leu Thr Val Asn Leu Thr Arg Phe Pro
    195                 200                 205

Glu Thr Val Pro Arg Glu Leu Val Pro Val Ala Gly Ser Cys Val
210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
            245                 250                 255

Pro Gly Phe Glu Ala Ala Glu Gly Asn Thr Lys Cys Arg Ala Cys Ala
        260                 265                 270

Gln Gly Thr Phe Lys Pro Leu Ser Gly Glu Gly Ser Cys Gln Pro Cys
    275                 280                 285

Pro Ala Asn Ser His Ser Asn Thr Ile Gly Ser Ala Val Cys Gln Cys
290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
            325                 330                 335

Ser Ser Leu His Leu Glu Trp Ser Ala Pro Leu Glu Ser Gly Gly Arg
        340                 345                 350

Glu Asp Leu Thr Tyr Ala Leu Arg Cys Arg Glu Cys Arg Pro Gly Gly
    355                 360                 365

Ser Cys Ala Pro Cys Gly Gly Asp Leu Thr Phe Asp Pro Gly Pro Arg
370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
            405                 410                 415

Thr Gly Pro Val Pro Phe Glu Pro Val Asn Val Thr Thr Asp Arg Glu
        420                 425                 430

Val Pro Pro Ala Val Ser Asp Ile Arg Val Thr Arg Ser Ser Pro Ser
    435                 440                 445

Ser Leu Ser Leu Ala Trp Ala Val Pro Arg Ala Pro Ser Gly Ala Val
450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
            485                 490                 495

Leu Lys Arg Gly Ala Ser Tyr Leu Val Gln Val Arg Ala Arg Ser Glu
        500                 505                 510

Ala Gly Tyr Gly Pro Phe Gly Gln Glu His His Ser Gln Thr Gln Leu
    515                 520                 525

Asp Glu Ser Glu Gly Trp Arg Glu Gln Leu Ala Leu Ile Ala Gly Thr
530                 535                 540

Ala Val Val Gly Val Val Leu Val Leu Val Val Ile Val Val Ala Val
545                 550                 555                 560
```

-continued

```
Leu Cys Leu Arg Lys Gln Ser Asn Gly Arg Glu Ala Glu Tyr Ser Asp
            565                 570                 575

Lys His Gly Gln Tyr Leu Ile Gly His Gly Thr Lys Val Tyr Ile Asp
            580                 585                 590

Pro Phe Thr Tyr Glu Asp Pro Asn Glu Ala Val Arg Glu Phe Ala Lys
            595                 600                 605

Glu Ile Asp Val Ser Tyr Val Lys Ile Glu Val Ile Gly Ala Gly
            610                 615                 620

Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
            645                 650                 655

Gln Arg Arg Glu Phe Leu Ser Glu Ala Ser Ile Met Gly Gln Phe Glu
            660                 665                 670

His Pro Asn Ile Ile Arg Leu Glu Gly Val Val Thr Asn Ser Met Pro
            675                 680                 685

Val Met Ile Leu Thr Glu Phe Met Glu Asn Gly Ala Leu Asp Ser Phe
            690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
            725                 730                 735

Val His Arg Asp Leu Ala Ala Arg Asn Ile Leu Val Asn Ser Asn Leu
            740                 745                 750

Val Cys Lys Val Ser Asp Phe Gly Leu Ser Arg Phe Leu Glu Glu Asn
            755                 760                 765

Ser Ser Asp Pro Thr Tyr Thr Ser Ser Leu Gly Gly Lys Ile Pro Ile
            770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
            805                 810                 815

Gly Glu Arg Pro Tyr Trp Asp Met Ser Asn Gln Asp Val Ile Asn Ala
            820                 825                 830

Ile Glu Gln Asp Tyr Arg Leu Pro Pro Pro Asp Cys Pro Thr Ser
            835                 840                 845

Leu His Gln Leu Met Leu Asp Cys Trp Gln Lys Asp Arg Asn Ala Arg
            850                 855                 860

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
            885                 890                 895

Pro Leu Leu Asp Gln Arg Gln Pro His Tyr Ser Ala Phe Gly Ser Val
            900                 905                 910

Gly Glu Trp Leu Arg Ala Ile Lys Met Gly Arg Tyr Glu Glu Ser Phe
            915                 920                 925

Ala Ala Ala Gly Phe Gly Ser Phe Glu Leu Val Ser Gln Ile Ser Ala
            930                 935                 940

Glu Asp Leu Leu Arg Ile Gly Val Thr Leu Ala Gly His Gln Lys Lys
945                 950                 955                 960
```

-continued

```
Ile Leu Ala Ser Val Gln His Met Lys Ser Gln Ala Lys Pro Gly Thr
                965                 970                 975
Pro Gly Gly Thr Gly Gly Pro Ala Pro Gln Tyr
            980             985
```

US 8,975,377 B2

CANCER TREATMENT USING HUMANIZED ANTIBODIES THAT BIND TO EPHB4

RELATED APPLICATIONS

This application claims the benefit of priority of U.S. Provisional Application No. 60/964,496 filed Aug. 13, 2007, the entire teachings of which are incorporated herein by reference in their entirety.

BACKGROUND OF THE INVENTION

Angiogenesis, the development of new blood vessels from the endothelium of a preexisting vasculature, is a critical process in the growth, progression, and metastasis of solid tumors within the host. During physiologically normal angiogenesis, the autocrine, paracrine, and amphicrine interactions of the vascular endothelium with its surrounding stromal components are tightly regulated both spatially and temporally. Additionally, the levels and activities of proangiogenic and angiostatic cytokines and growth factors are maintained in balance. In contrast, the pathological angiogenesis necessary for active tumor growth is sustained and persistent, representing a dysregulation of the normal angiogenic system. Solid and hematopoietic tumor types are particularly associated with a high level of abnormal angiogenesis.

It is generally thought that the development of tumor consists of sequential, and interrelated steps that lead to the generation of an autonomous clone with aggressive growth potential. These steps include sustained growth and unlimited self-renewal. Cell populations in a tumor are generally characterized by growth signal self-sufficiency, decreased sensitivity to growth suppressive signals, and resistance to apoptosis. Genetic or cytogenetic events that initiate aberrant growth sustain cells in a prolonged "ready" state by preventing apoptosis.

SUMMARY OF THE INVENTION

This application provides, inter alia, antibodies, e.g., modified antibodies, or antigen-binding fragments thereof that bind to the extracellular domain of EphB4. The modified anti-EphB4 antibodies, or antigen-binding fragments thereof are less immunogenic compared to their unmodified parent antibodies in a given species, e.g., a human. The antibodies and antigen binding fragments are useful in therapeutic treatments for affecting EphB4 function in order to inhibit angiogenesis and tumor growth.

In one embodiment, the application provides a deimmunized antibody or antigen binding fragment thereof that binds the extracellular domain of EphB4, including a heavy chain variable region and a light chain variable region, wherein each variable region has between 2 to 20 amino acid substitutions in the framework region in comparison to a nonhuman or parent antibody that binds the extracellular domain of EphB4.

In one embodiment, the deimmunized antibody or antigen binding fragment thereof has one or more complementarity determining regions (CDRs) from a nonhuman or parent antibody that binds the extracellular domain of EphB4. In one embodiment, between 1-5 substitutions are present in the complementarity determining regions (CDRs).

In one embodiment, one or more substitutions reduces the number of T-cell epitopes in the deimmunized antibody or antigen binding fragment thereof as compared to the nonhuman or parent antibody. In one embodiment, one or more substitutions reduces the number of B-cell epitopes in the deimmunized antibody or antigen binding fragment thereof as compared to the nonhuman or parent antibody. In one embodiment, one or more substitutions introduces one or more regulatory T-cell epitopes in the deimmunized antibody or antigen binding fragment thereof as compared to the nonhuman or parent antibody.

In one embodiment, the heavy chain variable region of the deimmunized antibody or antigen binding fragment thereof has 20 or fewer amino acid substitutions in comparison to a nonhuman or parent antibody that binds the extracellular domain of EphB4. In another embodiment, the heavy chain variable region of the deimmunized antibody or antigen binding fragment thereof has 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, or 7 or fewer amino acid substitutions in comparison to a nonhuman or parent antibody that binds the extracellular domain of EphB4. In one embodiment, the heavy chain variable region has at least 2, at least 3, at least 4, at least 5, at least 6, at least 7, at least 8, at least 9, at least 10, at least 11, at least 12, or at least 13 amino acid substitutions in comparison to a nonhuman or parent antibody.

In one embodiment, the light chain variable region of the deimmunized antibody or antigen binding fragment thereof has 20 or fewer amino acid substitutions in comparison to a nonhuman or parent antibody that binds the extracellular domain of EphB4. In another embodiment, the light chain variable region of the deimmunized antibody or antigen binding fragment thereof has 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, or 7 or fewer amino acid substitutions in comparison to a nonhuman or parent antibody that binds the extracellular domain of EphB4. In one embodiment, the light chain variable region has at least 2, at least 3, at least 4, at least 5, at least 6, at least 7, at least 8, at least 9, at least 10, at least 11, at least 12, or at least 13 amino acid substitutions in comparison to a nonhuman or parent antibody.

In one embodiment, the deimmunized antibody or antigen binding fragment thereof binds to the extracellular domain of EphB4 with a similar or greater binding affinity than mouse monoclonal antibody #131, ATCC deposit number PTA-6214.

In one embodiment, the substitutions in the deimmunized antibody or antigen binding fragment thereof result in an increase in the sequence identity between the framework region of the antibody or antigen binding fragment and a human germline gene sequence that is homologous to said framework region.

In one embodiment, the deimmunized antibody or antigen binding fragment thereof inhibits the formation of tubes by cultured endothelial cells. In another embodiment, the deimmunized antibody or antigen binding fragment thereof inhibits the vascularization of a tissue in vivo. In another embodiment, the deimmunized antibody or antigen binding fragment thereof decreases the growth of a human tumor xenograft in a mouse. In a further embodiment, the deimmunized antibody or antigen binding fragment thereof inhibits the vascularization of tissue implanted in the cornea of an animal or the vascularization of a Matrigel tissue plug implanted in an animal. In one embodiment, the deimmunized antibody or antigen binding fragment thereof promotes apoptosis.

In some embodiments, the effector function of the deimmunized antibody or antigen binding fragment thereof is altered. In another embodiment, the effector function of the deimmunized antibody or antigen binding fragment thereof is increased. In another embodiment, the effector function of the deimmunized antibody or antigen binding fragment thereof is decreased. In some embodiments, the deimmunized antibody or antigen binding fragment comprises a heavy chain constant region. In some embodiments, the N-glycosylation in the Fc region is removed. In some embodiments, the Fc region comprises a mutation within the N-glycosylation recognition sequence, whereby the Fc region of the antibody or polypeptide is not N-glycosylated. In some embodiments, the Fc region is PEGylated. In some embodiments, the heavy chain constant region is a human heavy chain IgG2a constant region containing the following residues: serine at positions 330 and 331. In some embodiments, the heavy chain constant region is a human heavy chain IgG4 comprising the following mutations: proline at position 233, valine at position 234, and alanince at position 235. These amino acid positions are based on Kabat numbering In one embodiment, the deimmunized antibody or antigen binding fragment thereof inhibits EphB4 dimerization or multimerization. In one embodiment, the deimmunized antibody or antigen binding fragment thereof inhibits the EphrinB2 stimulated autophosphorylation of EphB4. In one embodiment, the deimmunized antibody or antigen binding fragment thereof stimulates EphB4 kinase activity.

In one embodiment, the deimmunized antibody or antigen binding fragment thereof binds to the first fibronectin-like domain of EphB4. In one embodiment, the deimmunized antibody or antigen binding fragment thereof binds to the second fibronectin-like domain of EphB4.

In one embodiment, the deimmunized antibody or antigen binding fragment thereof is conjugated to a cytotoxic agent. In one embodiment, the cytotoxic agent is selected from the group consisting of a radioactive agent, a molecule of plant, fungal or bacterial origin, such as for example saporin, a biological protein, vinblastine, 4-desacetylvinblastine, vincristine, leurosidine, and vindesine. In certain embodiments, the antibody or antigen binding fragment thereof is conjugated to a cytotoxic agent through a stable linker which releases the cytotoxic agent inside cancer cells.

In one embodiment, the variable region of the antibody or antigen binding fragment has between 2 to 20 amino acid substitutions in comparison to a nonhuman or parent antibody that binds the extracellular domain, wherein said nonhuman or parent antibody also provides one or more CDRs in the deimmunized antibody or antigen binding fragment thereof. In a further embodiment, the deimmunized antibody or antigen binding fragment thereof includes a heavy chain variable region and a light chain variable region, wherein each variable region has between 2 to 20 amino acid substitutions in comparison to a nonhuman or parent antibody that binds the extracellular domain of EphB4, and the deimmunized antibody or antigen binding fragment thereof has one or more complementarity determining regions (CDRs) from said nonhuman or parent antibody. In a further embodiment, the deimmunized antibody or antigen binding fragment thereof is less immunogenic in a human subject than said nonhuman or parent antibody.

In one embodiment, the nonhuman or parent antibody is mouse monoclonal #47 or mouse monoclonal #131; ATCC Deposit Designation Nos. PTA-11338 and PTA-6214, respectively. In a further embodiment, one or more of the substitutions in the heavy chain variable region occurs at an amino acid position selected from the group consisting of positions 5, 12, 40, 66, 75, and 83 according to the Kabat numbering system. In a further embodiment, one or more substitutions in the heavy chain variable region is selected from the group consisting of valine at position 5, lysine at position 12, alanine at position 40, arginine at position 66, threonine at position 75, and arginine at position 83, said positions according to the Kabat numbering system. In a further embodiment, one or more substitutions in the light chain variable region occurs at an amino acid position selected from the group consisting of positions 45, 74, and 100, according to the Kabat numbering system. In another embodiment, one or more substitutions in the light chain variable region is selected from the group consisting of lysine at position 45, threonine at position 74, and glutamine at position 100, according to the Kabat numbering system.

In one embodiment, the heavy chain variable region includes a) an FR1 selected from the group consisting of amino acids 1-30 of SEQ ID NO:1, SEQ ID NO:3, SEQ ID NO:4, SEQ ID NO:10, SEQ ID NO:11, and SEQ ID NO:13, b) an FR2 selected from the group consisting of amino acids 36-49 of SEQ ID NO:1, SEQ ID NO:3, SEQ ID NO:5, SEQ ID NO:10, and SEQ ID NO:13; c) an FR3 selected from the group consisting of amino acids 67-98 of SEQ ID NO:1, SEQ ID NO:2, SEQ ID NO:3, SEQ ID NO:4, SEQ ID NO:5, SEQ ID NO:10, SEQ ID NO:11, SEQ ID NO:12, and SEQ ID NO:14; and d) an FR4 selected from the group consisting of amino acids 113-123 of SEQ ID NO:1 and SEQ ID NO:10.

In one embodiment, the light chain variable region includes a) an FR1 selected from the group consisting of amino acids 1-23 of SEQ ID NO:6, SEQ ID NO:15, and SEQ ID NO:16, b) an FR2 selected from the group consisting of amino acids 35-49 of SEQ ID NO:6, SEQ ID NO:7, SEQ ID NO:9, SEQ ID NO:15, and SEQ ID NO:18; c) an FR3 selected from the group consisting of amino acids 57-88 of SEQ ID NO:6, SEQ ID NO:7, SEQ ID NO:8, SEQ ID NO:15, and SEQ ID NO:17; and d) an FR4 selected from the group consisting of amino acids 98-107 of SEQ ID NO:6 and SEQ ID NO:15.

In one embodiment, the heavy chain variable region of the deimmunized antibody or antigen binding fragment thereof includes a CDR1 including SEQ ID NO:19, a CDR2 including SEQ ID NO:20, and a CDR3 including SEQ ID NO:21; and wherein the light chain includes a CDR1 including SEQ ID NO:22, a CDR2 including SEQ ID NO:23, and a CDR3 including SEQ ID NO:24. In a further embodiment, the deimmunized antibody or antigen binding fragment thereof is less immunogenic in a human subject than mouse monoclonal antibody #47. In a further embodiment, the deimmunized antibody or antigen binding fragment thereof binds the extracellular domain of EphB4 with a binding affinity which is at least 80%, at least 90%, or at least 100% of the binding affinity of mouse monoclonal antibody #47 binding to the extracellular domain of EphB4.

In a further embodiment, the deimmunized antibody or antigen binding fragment thereof inhibits binding of EphB4 to the extracellular portion of EphrinB2. In a further embodiment, the deimmunized antibody or antigen binding fragment thereof inhibits EphB4 dimerization or multimerization. In a further embodiment, the deimmunized antibody or antigen binding fragment thereof inhibits the EphrinB2 stimulated autophosphorylation of EphB4. In a further embodiment, the deimmunized antibody or antigen binding fragment thereof stimulates EphB4 kinase activity. In a further embodiment, the deimmunized antibody or antigen binding fragment thereof binds to the first fibronectin-like domain of EphB4. In a further embodiment, the binds to the second fibronectin-like domain of EphB4.

In a further embodiment, the deimmunized antibody or antigen binding fragment thereof is conjugated to a cytotoxic agent. In a further embodiment, the cytotoxic agent is selected from the group consisting of a radioactive agent, a molecule of plant, fungal or bacterial origin such as saporin, a biological protein, vinblastine, 4-desacetylvinblastine, vincristine, leurosidine, and vindesine. In certain embodiments, the antibody or antigen binding fragment thereof is conjugated to a cytotoxic agent through a stable linker which releases the cytotoxic agent inside cancer cells.

In a further embodiment, the deimmunized antibody or antigen binding fragment thereof inhibits the formation of tubes by cultured endothelial cells. In a further embodiment, the deimmunized antibody or antigen binding fragment thereof inhibits the vascularization of a tissue in vivo. In a further embodiment, the deimmunized antibody or antigen binding fragment thereof decreases the growth of a human tumor xenograft in a mouse. In a further embodiment, the deimmunized antibody or antigen binding fragment thereof inhibits the vascularization of tissue implanted in the cornea of an animal or the vascularization of a Matrigel tissue plug implanted in an animal. In a further embodiment, the deimmunized antibody or antigen binding fragment thereof promotes apoptosis.

In some embodiments, the effector function of the deimmunized antibody or antigen binding fragment thereof is altered. In another embodiment, the effector function of the deimmunized antibody or antigen binding fragment thereof is increased. In another embodiment, the effector function of the deimmunized antibody or antigen binding fragment thereof is decreased. In some embodiments, the deimmunized antibody or antigen binding fragment comprises a heavy chain constant region. In some embodiments, the N-glycosylation in the Fc region is removed.

In a further embodiment, the heavy chain variable region of antibody or antigen binding fragment thereof includes a) an FR1 selected from the group consisting of amino acids 1-30 of SEQ ID NO:1, SEQ ID NO:3, and SEQ ID NO:4, b) an FR2 selected from the group consisting of amino acids 36-49 of SEQ ID NO:1, SEQ ID NO:3, and SEQ ID NO:5; c) an FR3 selected from the group consisting of amino acids 67-98 of SEQ ID NO:1, SEQ ID NO:2, SEQ ID NO:3, SEQ ID NO:4, and SEQ ID NO:5; and d) an FR4 consisting of amino acids 113-123 of SEQ ID NO:1; and the light chain variable region includes a) an FR1 consisting of amino acids 1-23 of SEQ ID NO:6, b) an FR2 selected from the group consisting of amino acids 35-49 of SEQ ID NO:6, SEQ ID NO:7, and SEQ ID NO:9; c) an FR3 selected from the group consisting of amino acids 57-88 of SEQ ID NO:6, SEQ ID NO:7, and SEQ ID NO:8; and d) an FR4 consisting of amino acids 98-107 of SEQ ID NO:6.

In a further embodiment, the heavy chain variable region of the antibody or antigen binding fragment includes an amino acid sequence selected from the group consisting of: a) SEQ ID NO:1; b) SEQ ID NO:2; c) SEQ ID NO: 3, d) SEQ ID NO: 4, and e) SEQ ID NO:5.

In a further embodiment, the light chain variable region of the antibody or antigen binding fragment includes an amino acid sequence selected from the group consisting of: a) SEQ ID NO: 6; b) SEQ ID NO:7; c) SEQ ID NO: 8, and d) SEQ ID NO: 9.

In a further embodiment, the heavy chain variable region of the antibody or antigen binding fragment includes an amino acid sequence selected from the group consisting of: a) SEQ ID NO:1; b) SEQ ID NO:2; c) SEQ ID NO: 3, d) SEQ ID NO: 4, and e) SEQ ID NO:5; and the light chain variable region of the antibody or antigen binding fragment includes an amino acid sequence selected from the group consisting of: a) SEQ ID NO: 6; b) SEQ ID NO:7; c) SEQ ID NO: 8, and d) SEQ ID NO: 9.

In a further embodiment, the heavy chain variable region of the antibody or antigen binding fragment includes the amino acid sequence of SEQ ID NO: 3, and the light chain variable region includes an amino acid sequence selected from the group consisting of: a) SEQ ID NO: 7 and b) SEQ ID NO:8.

In a further embodiment, the heavy chain variable region includes the amino acid sequence of SEQ ID NO: 4, and the light chain variable region includes an amino acid sequence selected from the group consisting of: a) SEQ ID NO: 7 and b) SEQ ID NO:8.

In a further embodiment, the heavy chain variable region includes the amino acid sequence of SEQ ID NO: 3, and the light chain variable region includes the amino acid sequence of SEQ ID NO:8.

In one embodiment, the heavy chain variable region of the antibody or antigen binding fragment includes a CDR1 including SEQ ID NO:25, a CDR2 including SEQ ID NO:26, and a CDR3 including SEQ ID NO:27; and the light chain variable region includes a CDR1 including SEQ ID NO:28, a CDR2 including SEQ ID NO:29, and a CDR3 including SEQ ID NO:30. In a further embodiment, the deimmunized antibody or antigen binding fragment thereof is less immunogenic in a human subject than mouse monoclonal antibody #131.

In a further embodiment, the deimmunized antibody or antigen binding fragment thereof binds the extracellular domain of EphB4 with a binding affinity which is at least 80%, at least 90%, or at least 100% of the binding affinity of mouse monoclonal antibody #131 binding to the extracellular domain of EphB4.

In a further embodiment, the deimmunized antibody or antigen binding fragment thereof inhibits binding of EphB4 to the extracellular portion of EphrinB2. In a further embodiment, the deimmunized antibody or antigen binding fragment thereof inhibits EphB4 dimerization or multimerization. In a further embodiment, the deimmunized antibody or antigen binding fragment thereof inhibits the EphrinB2 stimulated autophosphorylation of EphB4. In a further embodiment, the deimmunized antibody or antigen binding fragment thereof stimulates EphB4 kinase activity. In a further embodiment, the deimmunized antibody or antigen binding fragment thereof binds to the first fibronectin-like domain of EphB4. In a further embodiment, the deimmunized antibody or antigen binding fragment thereof binds to the second fibronectin-like domain of EphB4.

In a further embodiment, the deimmunized antibody or antigen binding fragment thereof is conjugated to a cytotoxic agent. In a further embodiment, the cytotoxic agent is selected from the group consisting of a compound that emits radiation, a molecule of plant, fungal or bacterial origin, such as saporin, a biological protein, vinblastine, 4-desacetylvinblastine, vincristine, leurosidine, and vindesine. In certain embodiments, the antibody or antigen binding fragment thereof is conjugated to a cytotoxic agent through a stable linker which releases the cytotoxic agent inside cancer cells.

In a further embodiment, the antibody or antigen binding fragment inhibits the formation of tubes by cultured endothelial cells. In a further embodiment, the deimmunized antibody or antigen binding fragment thereof inhibits the vascularization of a tissue in vivo. In a further embodiment, the deimmunized antibody or antigen binding fragment thereof decreases the growth of a human tumor xenograft in a mouse. In a further embodiment, the deimmunized antibody or antigen binding fragment thereof inhibits the vascularization of tissue implanted in the cornea of an animal or the vascularization of a Matrigel tissue plug implanted in an animal. In a further embodiment, the deimmunized antibody or antigen binding fragment thereof promotes apoptosis.

In some embodiments, the effector function of the deimmunized antibody or antigen binding fragment thereof is altered. In another embodiment, the effector function of the deimmunized antibody or antigen binding fragment thereof is increased. In another embodiment, the effector function of the deimmunized antibody or antigen binding fragment thereof is decreased. In some embodiments, the deimmunized antibody or antigen binding fragment comprises a heavy chain constant region. In some embodiments, the N-glycosylation in the Fc region is removed.

In a further embodiment, the heavy chain variable region of the deimmunized antibody or antigen binding fragment thereof includes a) an FR1 selected from the group consisting of amino acids 1-30 of SEQ ID NO:10, SEQ ID NO:11, and SEQ ID NO:13, b) an FR2 selected from the group consisting of amino acids 36-49 of SEQ ID NO:10, and SEQ ID NO:13; c) an FR3 selected from the group consisting of amino acids 67-98 of SEQ ID NO:10, SEQ ID NO:11, SEQ ID NO:12, and SEQ ID NO:14; and d) an FR4 consisting of amino acids 113-123 of SEQ ID NO:10; and wherein the light chain variable region includes a) an FR1 selected from the group consisting of amino acids 1-23 of SEQ ID NO:15, and SEQ ID NO:16, b) an FR2 selected from the group consisting of amino acids 35-49 of SEQ ID NO:15, and SEQ ID NO:18; c) an FR3 selected from the group consisting of amino acids 57-88 of SEQ ID NO:15, and SEQ ID NO:17; and d) an FR4 consisting of amino acids 98-107 of SEQ ID NO:15.

In a further embodiment, the heavy chain variable region includes an amino acid sequence selected from the group consisting of: a) SEQ ID NO:10; b) SEQ ID NO:11; c) SEQ ID NO:12, d) SEQ ID NO:13, and e) SEQ ID NO:14.

In a further embodiment, the light chain variable region includes an amino acid sequence selected from the group consisting of: a) SEQ ID NO:15; b) SEQ ID NO:16, c) SEQ ID NO:17, and d) SEQ ID NO:18.

In a further embodiment, the heavy chain variable region includes the amino acid sequence of SEQ ID NO:13, and the light chain variable region includes an amino acid sequence selected from the group consisting of: a) SEQ ID NO:17 and b) SEQ ID NO:18.

In a further embodiment, the heavy chain variable region includes the amino acid sequence of SEQ ID NO:14, and the light chain variable region includes an amino acid sequence selected from the group consisting of: a) SEQ ID NO:17 and b) SEQ ID NO:18. In a further embodiment, the heavy chain variable region includes the amino acid sequence of SEQ ID NO:14, and the light chain variable region includes the amino acid sequence of SEQ ID NO:18.

In one embodiment, the deimmunized antibody or antigen binding fragment that binds to the extracellular domain of EphB4 with the same or greater affinity than the parent or nonhuman antibody comprises a heavy chain variable region and a light chain variable region. The deimmunized antibody or antigen binding fragment has one or more of the following characteristics: a) each variable region is derived entirely from one or more human antibodies; b) each variable region has a reduced number of T-cell epitopes compared to the parent or nonhuman antibody; and c) each variable region has a reduced number of B-cell epitopes compared to the parent or nonhuman antibody. In one embodiment, each variable region is a composite of segments from one or more human antibodies. In one embodiment, the human antibody segments are from 2 to 35 amino acids in length. In one embodiment, the human antibody segments do not comprise an entire CDR or individual framework region. In a further embodiment, one or more of the following residues are present in the heavy chain variable region: valine at position 5, lysine at position 12, alanine at position 40, arginine at position 66, threonine at position 75, and arginine at position 83, said positions according to the Kabat numbering system. In a further embodiment, one or more of the following residues are present in the light chain variable region: lysine at position 45, threonine at position 74, and glutamine at position 100, said positions according to the Kabat numbering system.

In a further embodiment, the heavy chain variable region comprises a CDR1 comprising SEQ ID NO:25, a CDR2 comprising SEQ ID NO:26, and a CDR3 comprising SEQ ID NO:27; and the light chain variable region comprises a CDR1 comprising SEQ ID NO:28, a CDR2 comprising SEQ ID NO:29, and a CDR3 comprising SEQ ID NO:30. In a further embodiment, the heavy chain variable region comprises a) an FR1 selected from the group consisting of amino acids 1-30 of SEQ ID NO:10, SEQ ID NO:11, and SEQ ID NO:13, b) an FR2 selected from the group consisting of amino acids 36-49 of SEQ ID NO:10, and SEQ ID NO:13; c) an FR3 selected from the group consisting of amino acids 67-98 of SEQ ID NO:10, SEQ ID NO:11, SEQ ID NO:12, and SEQ ID NO:14; and d) an FR4 consisting of amino acids 113-123 of SEQ ID NO:10; and the light chain variable region comprises a) an FR1 selected from the group consisting of amino acids 1-23 of SEQ ID NO:15, and SEQ ID NO:16, b) an FR2 selected from the group consisting of amino acids 35-49 of SEQ ID NO:15, and SEQ ID NO:18; c) an FR3 selected from the group consisting of amino acids 57-88 of SEQ ID NO:15, and SEQ ID NO:17; and d) an FR4 consisting of amino acids 98-107 of SEQ ID NO:15.

In another embodiment, the heavy chain variable region comprises a CDR1 comprising SEQ ID NO:19, a CDR2 comprising SEQ ID NO:20, and a CDR3 comprising SEQ ID NO:21; and wherein the light chain comprises a CDR1 comprising SEQ ID NO:22, a CDR2 comprising SEQ ID NO:23, and a CDR3 comprising SEQ ID NO:24. In a further embodiment, the heavy chain variable region comprises a) an FR1 selected from the group consisting of amino acids 1-30 of SEQ ID NO:1, SEQ ID NO:3, and SEQ ID NO:4, b) an FR2 selected from the group consisting of amino acids 36-49 of SEQ ID NO:1, SEQ ID NO:3, and SEQ ID NO:5; c) an FR3 selected from the group consisting of amino acids 67-98 of SEQ ID NO:1, SEQ ID NO:2, SEQ ID NO:3, SEQ ID NO:4, and SEQ ID NO:5; and d) an FR4 consisting of amino acids 113-123 of SEQ ID NO:1; and the light chain variable region comprises a) an FR1 consisting of amino acids 1-23 of SEQ ID NO:6, b) an FR2 selected from the group consisting of amino acids 35-49 of SEQ ID NO:6, SEQ ID NO:7, and SEQ ID NO:9; c) an FR3 selected from the group consisting of amino acids 57-88 of SEQ ID NO:6, SEQ ID NO:7, and SEQ ID NO:8; and d) an FR4 consisting of amino acids 98-107 of SEQ ID NO:6.

In one embodiment, the deimmunized antibody or antigen binding fragment thereof that binds to the extracellular domain of EphB4 is less immunogenic than the #131 antibody obtained from a hybridoma having an ATCC deposit number PTA-614 and binds with the same or greater affinity than the antibody obtained from a hybridoma. In a further embodiment, heavy chain variable region of the deimmunized antibody or antigen binding fragment comprises a CDR1 comprising SEQ ID NO:25, a CDR2 comprising SEQ ID NO:26, and a CDR3 comprising SEQ ID NO:27; and the light chain variable region comprises a CDR1 comprising SEQ ID NO:28, a CDR2 comprising SEQ ID NO:29, and a CDR3 comprising SEQ ID NO:30. In a further embodiment, the heavy chain variable region comprises a) an FR1 selected from the group consisting of amino acids 1-30 of SEQ ID NO:10, SEQ ID NO:11, and SEQ ID NO:13, b) an FR2 selected from the group consisting of amino acids 36-49 of SEQ ID NO:10, and SEQ ID NO:13; c) an FR3 selected from the group consisting of amino acids 67-98 of SEQ ID NO:10, SEQ ID NO:11, SEQ ID NO:12, and SEQ ID NO:14; and d) an FR4 consisting of amino acids 113-123 of SEQ ID NO:10; and the light chain variable region comprises a) an FR1 selected from the group consisting of amino acids 1-23 of SEQ ID NO:15, and SEQ ID NO:16, b) an FR2 selected from the group consisting of amino acids 35-49 of SEQ ID NO:15, and SEQ ID NO:18; c) an FR3 selected from the group consisting of amino acids 57-88 of SEQ ID NO:15, and SEQ ID NO:17; and d) an FR4 consisting of amino acids 98-107 of SEQ ID NO:15.

In one embodiment, the deimmunized antibody or antigen binding fragment thereof that binds to the extracellular domain of EphB4 is less immunogenic than the #47 antibody obtained from a hybridoma having an ATCC deposit number PTA 11338 and binds with the same or greater affinity than the antibody obtained from a hybridoma. In a further embodiment, the heavy chain variable region of the deimmunized antibody or antigen binding fragment comprises a CDR1 comprising SEQ ID NO:19, a CDR2 comprising SEQ ID NO:20, and a CDR3 comprising SEQ ID NO:21; and the light chain comprises a CDR1 comprising SEQ ID NO:22, a CDR2 comprising SEQ ID NO:23, and a CDR3 comprising SEQ ID NO:24. In a further embodiment, the heavy chain variable region comprises a) an FR1 selected from the group consisting of amino acids 1-30 of SEQ ID NO:1, SEQ ID NO:3, and SEQ ID NO:4, b) an FR2 selected from the group consisting of amino acids 36-49 of SEQ ID NO:1, SEQ ID NO:3, and SEQ ID NO:5; c) an FR3 selected from the group consisting of amino acids 67-98 of SEQ ID NO:1, SEQ ID NO:2, SEQ ID NO:3, SEQ ID NO:4, and SEQ ID NO:5; and d) an FR4 consisting of amino acids 113-123 of SEQ ID NO:1; and the light chain variable region comprises a) an FR1 consisting of amino acids 1-23 of SEQ ID NO:6, h) an FR2 selected from the group consisting of amino acids 35-49 of SEQ ID NO:6, SEQ ID NO:7, and SEQ ID NO:9; c) an FR3 selected from the group consisting of amino acids 57-88 of SEQ NO:6, SEQ ID NO:7, and SEQ ID NO:8; and d) an FR4 consisting of amino acids 98-107 of SEQ ID NO:6.

In one embodiment, the deimmunized antibody or antigen binding fragment that binds to the extracellular domain of EphB4 has a heavy chain variable region that comprises one or more on the following: valine at position 5, lysine at position 12, alanine at position 40, arginine at position 66, threonine at position 75, and arginine at position 83, said positions according to the Kabat numbering system. In a further embodiment, the deimmunized antibody or antigen binding fragment has a light chain variable region that comprises one or more on the following: lysine at position 45, threonine at position 74, and glutamine at position 100, said positions according to the Kabat numbering system.

In one embodiment, a method of reducing the growth rate of a tumor in a subject is provided. In a further embodiment the method includes administering to the subject a therapeutically effective amount of a deimmunized antibody or antigen binding fragment thereof disclosed herein. In one embodiment, the subject is a human subject. In one embodiment, the tumor includes cells expressing a higher level of EphB4 than noncancerous cells of a comparable tissue.

In one embodiment, the application provides a method of promoting apoptosis and thereby treating a subject suffering from cancer. In a further embodiment, the method includes administering to the subject a therapeutically effective amount of the deimmunized antibody or antigen binding fragment thereof disclosed herein. In one embodiment, the subject is a human subject. In one embodiment, the cancer includes cancer cells expressing EphB4 at a higher level than noncancerous cells of a comparable tissue. The cancer may be a metastatic cancer. In a further embodiment, the cancer is selected from the group consisting of colon carcinoma, breast tumor, mesothelioma, prostate tumor, squamous cell carcinoma, Kaposi sarcoma, ovarian cancer, and leukemia. In one embodiment, the cancer is an angiogenesis-dependent cancer or an angiogenesis independent cancer. In one embodiment, the antibody or antigen-binding fragment may be co-administered with one or more additional anti-cancer chemotherapeutic agents that inhibit cancer cells in an additive or synergistic manner with the antibody or antigen binding fragment.

In certain embodiments, the disclosure provides methods for treating a subject suffering from a cancer, including: (a) identifying in the subject a tumor having a plurality of cancer cells that express EphB4 and/or EphrinB2; and (b) administering to the subject an antibody or antigen-binding fragment which binds to an extracellular domain of an EphB4 protein.

In one embodiment, a method of inhibiting angiogenesis in a subject is provided. In a further embodiment, the method includes administering to a subject in need thereof an effective amount of the antibody disclosed herein. In one embodiment, the subject is a human subject. In a further embodiment, the subject is diagnosed with macular degeneration.

In one embodiment, a method may comprise contacting a cell with an amount of a deimmunized antibody or antigen-binding fragment sufficient to inhibit angiogenesis.

In certain aspects, the disclosure provides methods for treating a subject suffering from an angiogenesis-associated disease, including administering to the subject a deimmunized antibody or antigen-binding fragment which binds to an extracellular domain of an EphB4 protein. The antibody or antigen-binding fragment may be formulated with a pharmaceutically acceptable carrier. An angiogenesis related disease or unwanted angiogenesis related process may be selected from the group consisting of angiogenesis-dependent cancer, benign tumors, inflammatory disorders, chronic articular rheumatism and psoriasis, ocular angiogenic diseases, Osler-Webber Syndrome, myocardial angiogenesis, plaque neovascularization, telangiectasia, hemophiliac joints, angiofibroma, wound granulation, wound healing, telangiectasia psoriasis scleroderma, pyogenic granuloma, cororany collaterals, ischemic limb angiogenesis, rubeosis, arthritis, diabetic neovascularization, fractures, vasculogenesis, and hematopoiesis. An antibody or antigen-binding fragment may be co-administered with at least one additional anti-angiogenesis agent that inhibits angiogenesis in an additive or synergistic manner with the antibody or antigen-binding fragment.

In a further embodiment of the methods of treatment, the deimmunized antibody or antigen binding fragment thereof is administered systemically. In a further embodiment, the deimmunized antibody or antigen binding fragment thereof is administered locally.

In one embodiment, a pharmaceutical composition including a deimmunized antibody or antigen binding fragment thereof disclosed herein is provided. In a further embodiment, the composition may also include any pharmaceutically acceptable carriers or excipients.

In one embodiment the use of the deimmunized antibodies or antigen binding fragments thereof disclosed herein in the manufacture of a medicament for treating cancer is provided. In a further embodiment, the cancer is selected from the group consisting of colon carcinoma, breast tumor, mesothelioma, prostate tumor, squamous cell carcinoma, Kaposi sarcoma, ovarian cancer, and leukemia. In a further embodiment, a use of the deimmunized antibodies or antigen binding fragments thereof disclosed herein in the manufacture of a medicament for inhibiting angiogenesis is provided.

In one embodiment the deimmunized antibody or antibody binding fragment may inhibit an activity of the EphB4. An antibody may be designed to inhibit the interaction between Ephrin B2 and EphB4. An antagonist antibody will generally affect Eph and/or Ephrin signaling. For example, an antibody may inhibit clustering or phosphorylation of EphB4. In one embodiment, the deimmunized antibody or antibody binding fragment may also increase activity of the EphB4. An agonist antibody, for example, may upregulate EphB4 signaling.

In certain aspects the disclosure provides methods of inhibiting signaling through Ephrin B2/EphB4 pathway in a cell. A method may comprise contacting the cell with an effective amount of antibody or antibody binding fragment which binds to an extracellular domain of an EphB4 protein and inhibits an activity of the EphB4.

In certain embodiments, the deimmunized antibody or antibody binding fragment may be a polyclonal antibody, a monoclonal antibody or antibody fragment, a recombinant antibody, a diabody, a chimerized or chimeric antibody or antibody fragment, a humanized antibody or antibody fragment, a fully human antibody or antibody fragment, a CDR-grafted antibody or antibody fragment, a single chain antibody, an Fv, an Fd, an Fab, an Fab', or an F(ab')$_2$, and synthetic or semi-synthetic antibodies.

In certain embodiments, the deimmunized antibody or antibody fragment binds to an extracellular domain of an EphB4 protein with a dissociation constant ($K_D$) of at least about $1\times10^{-3}$ M, at least about $1\times10^{-4}$ M, at least about $1\times10^{-5}$ M, at least about $1\times10^{-6}$ M, at least about $1\times10^{-7}$ M, at least about $1\times10^{-8}$ M, at least about $1\times10^{-9}$ M, at least about $1\times10^{-10}$ M, at least about $1\times10^{-11}$ M, or at least about $1\times10^{-12}$ M, to an extracellular domain of an EphB4 protein.

In certain aspects, the deimmunized antibody or antibody fragment disclosed herein may be covalently linked (or otherwise stably associated with) an additional functional moiety, such as a label or a moiety that confers desirable pharmacokinetic properties. Exemplary labels include those that are suitable for detection by a method selected from the group consisting of: fluorescence detection methods, positron emission tomography detection methods and nuclear magnetic resonance detection methods. Labels may, for example, be selected from the group consisting of: a fluorescent label, a radioactive label, and a label having a distinctive nuclear magnetic resonance signature. Moieties such as a polyethylene glycol (PEG) moiety may be affixed to an antibody or antigen binding portion thereof to increase serum half-life. In certain embodiments, the deimmunized antibody or antibody fragment includes an altered constant region, wherein said antibody or antigen-binding fragment exhibits decreased effector function relative to an anti-Eph4B antibody with a native constant region. In certain embodiments, decreased effector function includes one or more properties of the following group: decreased antibody-dependent T-cell-mediated cytotoxicity (ADCC), and decreased complement dependent cytotoxicity (CDC) compared to an anti-Eph4B antibody with a native constant region.

In certain embodiments, the deimmunized antibody or antigen binding fragment thereof includes an altered constant region, wherein said antibody or antigen-binding fragment exhibits increased effector function relative to an anti-Eph4B antibody with a native constant region. In certain embodiments, increased effector function includes one or more properties of the following group: increased antibody-dependent T-cell-mediated cytotoxicity (ADCC), and increased complement dependent cytotoxicity (CDC), compared to an anti-Eph4B antibody with a native constant region.

In certain embodiments, the deimmunized antibody or antigen-binding fragment thereof has an anti-cancer activity. In certain embodiments, the anti-cancer activity may be inhibiting tumor growth, inhibiting cancer cell proliferation, inhibiting cancer cell migration, inhibiting metastasis of cancer cells, inhibiting angiogenesis, or causing tumor cell death.

In one embodiment, the application provides a diagnostic composition including an antibody of the application for detecting prostate cancer.

In one embodiment, the disclosure provides a deimmunized antibody or antigen binding fragment thereof that binds to an epitope situated in the extracellular portion of EphB4. The deimmunized antibody or antigen binding fragment thereof may bind to an epitope situated within amino acids 16-198 of the EphB4 sequence of FIG. 1. For example, the epitope may be situated within the globular domain (amino acids 29-197 of FIG. 1) of EphB4, which binds to EphrinB2. The deimmunized antibody or antigen binding fragment thereof may inhibit the binding of EphB4 to the extracellular portion of EphrinB2. The deimmunized antibody or antigen binding fragment thereof may bind to an epitope situated within amino acids 327-427 or 428-537 of the EphB4 sequence of FIG. 1. For example, the deimmunized antibody or antigen binding fragment thereof may bind to the first fibronectin-like domain (amino acids 324-429 of FIG. 1) or the second fibronectin-like domain (amino acids 434-526 of FIG. 1) of EphB4.

In other embodiments the antibody or antigen binding fragment is clinically acceptable for administration to a human.

In other embodiments, polynucleotides including a nucleotide sequence encoding the deimmunized antibody or antigen binding fragment thereof disclosed herein are provided. In other embodiments, polynucleotides that hybridize under stringent conditions to polynucleotides encoding the deimmunized antibody or antigen binding fragment thereof disclosed herein are provided.

In other embodiments, vectors including one or more nucleotide sequences encoding the deimmunized antibody or antigen binding fragment thereof disclosed herein are provided.

In other embodiments, isolated cells including a vector that expresses the deimmunized antibody or antigen binding fragment thereof disclosed herein are provided.

The application contemplates combinations of any of the foregoing aspects and embodiments.

BRIEF DESCRIPTION OF THE DRAWINGS

FIG. 1 shows the amino acid sequence of the EphB4 precursor protein. (Genbank accession number NP_004435 and SEQ ID NO:53)

FIGS. 2A-2D show amino acid alignments comparing the variable regions from the parental mouse monoclonal antibodies and the deimmunized variants. FIG. 2A depicts the heavy chain variable region of mouse monoclonal antibody #47 (SEQ ID NO:49) aligned with 5 deimmunized variants; FIG. 2B depicts the light chain variable region of #47 (SEQ ID NO:50) aligned with 4 deimmunized variants; FIG. 2C depicts the heavy chain variable region of mouse monoclonal antibody #131 (SEQ ID NO:51) aligned with 5 deimmunized variants; FIG. 2D depicts the light chain variable region of #131 (SEQ ID NO:52) aligned 4 deimmunized variants. Shaded residues indicate amino acids that differ from the parent mouse monoclonal antibody.

DETAILED DESCRIPTION OF THE INVENTION

I. Definitions

Figures 3A, 3B:
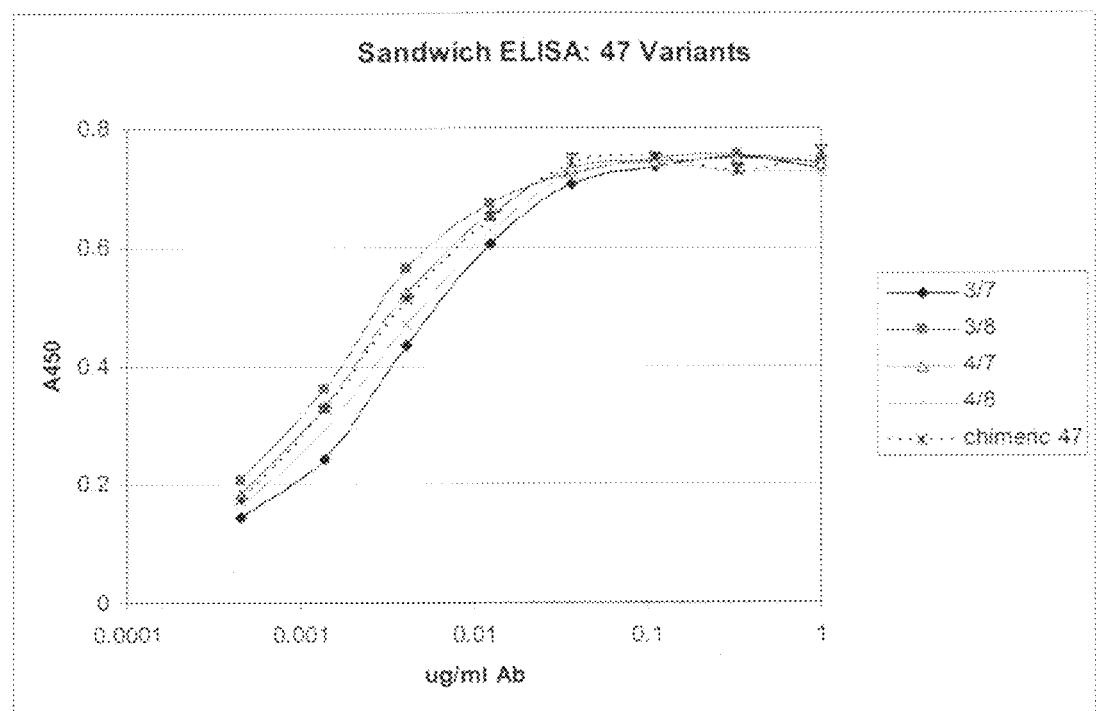
FIG. 3A depicts the results of extracellular EphB4 sandwich ELISA comparing the binding of a chimeric #47 antibody with 4 deimmunized #47 variant antibodies. The numbers indicate the sequence of the variable region. For example, "3/7" indicates an antibody with a heavy chain variable region of SEQ ID NO: 3 and a light chain variable region of SEQ ID NO:7.
FIG. 3B shows the concentration of each antibody where 50% binding in the ELISA is reached.

A "subject" refers to a vertebrate, such as for example, a mammal, or a human. Though the antibodies and antigen binding fragments of the present application are primarily concerned with the treatment of human subjects, they may also be employed for the treatment of other mammalian subjects such as dogs and cats for veterinary purposes.

As used herein, the terms "antibody" and "antibodies" (immunoglobulins) encompass, but are not limited to, monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')$_2$ fragments, antibody fragments that exhibit the desired biological activity, disulfide-linked Fvs (sdFv), intrabodies, and epitope-binding fragments or antigen binding fragments of any of the above. Antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "an antigen-binding fragment" refers to any portion of an antibody that retains binding to the antigen. An exemplary antigen-binding fragment of an antibody is the heavy chain and/or light chain CDR, or the heavy and/or light chain variable region.

The term "immunogenicity" refers to the ability of an antibody or antigen binding fragment to elicit an immune response (humoral or cellular) when administered to a recipient and includes, for example, the HAMA response. A HAMA response is initiated when T-cells from a subject make an immune response to the administered antibody. The T-cells then recruit B-cells to generate specific "anti-antibody" antibodies.

The term "T-cell epitopes" refers to specific peptide sequences which either bind with reasonable efficiency to MHC class II molecules or which are able to stimulate T-cells via presentation on MHC class II.

The term "B-cell epitopes" refers to peptide sequences recognized by B-cells. In general these sequences are solvent accessible.

The term deimmunization is a process that reduces the immunogenicity of a compound to a given species. A deimmunized antibody is an antibody that has lower immunogenicity in a given species than the corresponding parent or nonhuman antibody.

As used herein, the terms Ephrin and Eph are used to refer, respectively, to ligands and receptors. They can be from any of a variety of animals (e.g., mammals/non-mammals, vertebrates/non-vertebrates, including humans). The nomenclature in this area has changed rapidly and the terminology used herein is that proposed as a result of work by the Eph Nomenclature Committee, which can be accessed, along with previously-used names on the world wide web.

II. Overview

The Eph family receptors are a family of receptor protein-tyrosine kinases which are related to Eph, a receptor named for its expression in an erythropoietin-producing human hepatocellular carcinoma cell line. They are divided into two subgroups on the basis of the relatedness of their extracellular domain sequences and their ability to bind preferentially to Ephrin-A proteins or Ephrin-B proteins. Receptors which interact preferentially with Ephrin-A proteins are EphA receptors and those which interact preferentially with Ephrin-B proteins are EphB receptors.

Eph receptors have an extracellular domain composed of the ligand-binding globular domain, a cysteine rich region followed by a pair of fibronectin type III repeats. The cytoplasmic domain consists of a juxtamembrane region containing two conserved tyrosine residues; a protein tyrosine kinase domain; a sterile α-motif (SAM) and a PDZ-domain binding motif. EphB4 is specific for the membrane-bound ligand Ephrin B2 (Sakano, S. et al 1996; Brambilla R. et al 1995). Ephrin B2 belongs to the class of Eph ligands that have a transmembrane domain and cytoplasmic region with five conserved tyrosine residues and PDZ domain. Eph receptors are activated by binding of clustered, membrane attached ephrins (Davis S et al, 1994), indicating that contact between cells expressing the receptors and cells expressing the ligands is required for Eph activation.

Upon ligand binding, an Eph receptor dimerizes and autophosphorylate the juxtamembrane tyrosine residues to acquire full activation (Kalo M S et al, 1999, Binns K S, 2000). In addition to forward signaling through the Eph receptor, reverse signaling can occur through the ephrin Bs. Eph engagement of ephrins results in rapid phosphorylation of the conserved intracellular tyrosines (Bruckner K, 1997) and somewhat slower recruitment of PDZ binding proteins (Palmer A 2002).

The EphB4 precursor protein is depicted in FIG. 1. Amino acids 16-198 of the EphB4 sequence of FIG. 1 correspond to the Globular Domain (GD) of EphB4 that binds to EphrinB2. Amino acids 239-321 correspond to the cysteine rich domain and amino acids 324-429 and 434-526 correspond to the first fibronectin-like domain (FND1) and the second fibronectin-like domain (FND2) of EphB4 respectively.

Several studies have shown that high expression of Eph/ephrins may be associated with increased potentials for tumor growth, tumorigenicity, and metastasis (Easty D J, 1999; Kiyokawa E, 1994; Tang X X, 1999; Vogt T, 1998; Liu W, 2002; Stephenson S A, 2001; Steube K G 1999; Berclaz G, 1996). Application Ser. No. 10/949,720 demonstrates that EphB4 antibodies cause apoptosis, decrease angiogenesis, and inhibit tumor growth in a xenograft head and neck carcinoma tumor type.

The disclosure provides deimmunized antibodies and antigen binding fragments that may be used to treat cancer as well as angiogenesis related disorders and unwanted angiogenesis related processes.

Deimmunized antibodies and antigen binding fragments may be used to inhibit EphB4 function in vitro and in vivo. The disclosure provides antibodies that act as receptor antagonists, such as by inhibiting EphB4 and EphB2 interaction. The disclosure also provides antibodies and antigen binding portions thereof that act as agonists and activate EphB4 kinase activity (typically assessed by evaluating EphB4 phosphorylation state). Surprisingly, such antibodies also inhibit EphB4 functions in cell based and in vivo assays. Accordingly, such antibodies and antigen binding fragments may be used to inhibit EphB4 function in vitro and in vivo, and for treating cancer or disorders associated with unwanted angiogenesis. While not wishing to be limited to any particular mechanism, it is expected that antibodies which stimulate EphB4 kinase activity, also affect EphB4 removal from the membrane, thus decreasing overall EphB4 levels.

III. Antibodies

Antibodies are proteins produced by lymphocytes known as B-cells in vertebrates in response to stimulation by antigens. The basic structural unit of an antibody (or rather immunoglobulin (Ig)) molecule consists of four polypeptide chains which come together in the shape of a capital letter "Y". Two of the four chains are identical light (L) chains and two are identical heavy (H) chains. There are five different kinds (isotypes) of heavy chains which divide antibodies into five classes, namely, IgA, IgD, IgE, IgG and IgM. In addition, there are two different isotypes of light chains designated .kappa. and .lambda. Each class of heavy chains can combine with either of the light chains. The heavy and light chains each contain a variable region (VH and VL, respectively) that is involved in antigen binding and a constant (C) region. The antigen binding site is composed of six hypervariable regions (or rather complementarity determining regions (CDRs)). Three CDRs from the heavy chain and three CDRs from the light chain are respectively positioned between four relatively conserved anti-parallel .beta.-sheets which are called framework regions (FR1, FR2, FR3 and FR4), on each chain. By convention, numbering systems have been utilized to designate the location of the component parts of VH and VL chains. The Kabat definition is based on sequence variability and the Chothia definition is based on the location of structural loop regions. The Kabat definition for numbering is used herein.

In certain aspects, the present application provides deimmunized antibodies and antigen binding fragments against EphB4. Is some embodiments the deimmunized antibody or antigen binding fragment binds to an extracellular domain of EphB4. It is understood that antibodies may be Fab, Fv, scFv, Fab' and F(ab')$_2$, monoclonal and polyclonal antibodies, engineered antibodies (including chimeric, single chain, CDR-grafted, humanized, fully human antibodies, and artificially selected antibodies), and synthetic or semi-synthetic antibodies produced using phage display or alternative techniques.

In one embodiment of the application, the antibody fragments are truncated chains (truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dab fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining VL- and VH-coding regions with a DNA that encodes a peptide linker connecting the VL and VH protein fragments This application also provides fragments of anti-EphB4 antibodies, which may comprise a portion of an intact antibody, such as for example, the antigen-binding or variable region of the intact antibody. Examples of antibody fragments include Fab, Fab', F(ab')$_2$, and Fv fragments; diabodies; linear antibodies (Zapata et al., *Protein Eng.* 1995; 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an F(ab')$_2$ fragment that has two antigen-combining sites and is still capable of cross-linking antigen. "Fv" usually refers to the minimum antibody fragment that contains a complete antigen-recognition and -binding site. This region consists of a dimer of one heavy- and one light-chain variable region in tight, non-covalent association. It is in this configuration that the three CDRs of each variable region interact to define an antigen-binding site on the surface of the $V_H$-$V_L$ dimer. Collectively, the CDRs confer antigen-binding specificity to the antibody. However, even a single variable region (or half of an Fv comprising three CDRs specific for an antigen) has the ability to recognize and bind antigen, although likely at a lower affinity than the entire binding site.

Thus, in certain embodiments, the antibodies disclosed in the application may comprise 1, 2, 3, 4, 5, 6, or more CDRs that recognize the extracellular domain of EphB4.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

SMIPs are a class of single-chain peptides engineered to include a target binding region and effector domain (CH2 and CH3 domains). See, e.g., U.S. Patent Application Publication No. 20050238646. The target binding region may be derived from the variable region or CDRs of an antibody, e.g., an anti-EphB4 antibody of the application. Alternatively, the target binding region is derived from a protein that binds EphB4.

The term "diabodies" refers to small antibody fragments with two antigen-binding sites, which fragments comprise a heavy-chain variable region ($V_H$) connected to a light-chain variable region ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

It is well known that the binding to a molecule (or a pathogen) of antibodies with an Fc region assists in the processing and clearance of the molecule (or pathogen). The Fc portions of antibodies are recognized by specialized receptors expressed by immune effector cells. The Fc portions of IgG1 and IgG3 antibodies are recognized by Fc receptors present on the surface of phagocytic cells such as macrophages and neutrophils, which can thereby bind and engulf the molecules or pathogens coated with antibodies of these isotypes (Janeway et al., *Immunobiology* 5th edition, page 147, Garland Publishing (New York, 2001)).

The anti-EphB4 antibodies of the present application include antibodies having all types of constant regions, including IgM, IgG, IgD, IgA and IgE, and any isotype, including IgG1, IgG2a, IgG2b, IgG3 and IgG4. The light chains of the antibodies can either be kappa light chains or lambda light chains.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al., Science, 242: 423-426 (1988)), regarding single chain antibodies.

In certain aspects, the present application provides antibodies and antigen binding fragments having binding specificity for an EphB4 or a portion of EphB4. In some aspects the antibodies and antigen binding fragments bind to one or more specific domains of EphB4. For example, an antibody or antigen binding fragment binds to one or more extracellular domains of EphB4 (such as the globular domain, the cystein-rich domain, and the first fibronectin type 3 domain, and the second fibronectin type 3 domain). In some aspects, the immunoglobulins can bind to EphB4 with a dissociation constant ($K_D$) of at least about $1\times10^{-6}$, $1\times10^{-7}$, $1\times10^{-8}$, $1\times10^{-9}$ M or less. In certain embodiments antibodies and antigen binding fragments disclosed herein are specific for EphB4, with minimal binding to other members of the Eph or Ephrin families. In certain embodiments, the present application provides EphB4 antagonist antibodies. As described herein, the term "antagonist antibody" refers to an antibody that can inhibit one or more functions of an EphB4, such as a binding activity (e.g., ligand binding) and a signaling activity (e.g., clustering or phosphorylation of EphB4, stimulation of a cellular response, such as stimulation of cell migration or cell proliferation). For example, an antagonist antibody can inhibit (reduce or prevent) the interaction of an EphB4 receptor with a natural ligand (e.g., Ephrin B2 or fragments thereof). In some embodiments, antagonist antibodies directed against EphB4 can inhibit functions mediated by EphB4, including endothelial cell migration, cell proliferation, angiogenesis, and/or tumor growth. In certain embodiments, the antagonist antibody binds to an extracellular domain of EphB4.

In other embodiments, antibodies or antigen binding fragments are EphB4 agonists. In some embodiments antibodies or antigen binding fragments activate or enhance EphB4 kinase activity, even independent of EphrinB2. In some instances, such antibodies may be used to stimulate EphB4. However, applicants note that in most cell-based and in vivo assays, such antibodies surprisingly behaved like antagonist antibodies. Such antibodies appear to bind to the fibronectin type III domains, particularly the region of amino acids 327-427 of FIG. 1. In some embodiments, antibodies or antigen binding fragments that bind to the fibronectin type III domains of EphB4 can inhibit functions mediated by EphB4, including endothelial cell migration, cell proliferation, angiogenesis, and/or tumor growth.

In certain embodiments, single chain antibodies, and chimeric, humanized or primatized (CDR-grafted) antibodies, as well as chimeric or CDR-grafted single chain antibodies, comprising portions derived from different species, are also encompassed by the disclosure as antigen binding portions of an antibody.

In addition, antigen binding fragments of antibodies, including fragments of chimeric, humanized, primatized or single chain antibodies, can also be produced. Antigen binding fragments of the subject antibodies retain at least one binding function and/or modulation function of the full-length antibody from which they are derived. Certain antigen binding fragments retain the ability to inhibit one or more functions characteristic of an EphB4, such as a binding activity, a signaling activity, and/or stimulation of a cellular response. For example, in one embodiment, an antigen binding fragment of an EphB4 antibody can inhibit the interaction of EphB4 with one or more of its ligands (e.g., Ephrin B2) and/or can inhibit one or more receptor-mediated functions, such as cell migration, cell proliferation, angiogenesis, and/or tumor growth.

In one aspect, the deimmunized antibody or antigen binding fragment is a mouse antibody. In one aspect, the heavy and light chain variable regions each contain 2 to 20 amino acid substitutions. In one aspect, the substitutions comprise replacing at least one mouse amino acid with at least one corresponding human amino acid. In one aspect, the human amino acid is chosen based on identifying a human germline gene that is homologous to the mouse variable region. In one aspect, a homologous human germline gene is independently identified for each of the four framework regions of the mouse variable region.

The term "humanized antibody and antigen binding fragment" as used herein refers to an antibody or antigen binding fragment comprising portions of antibody of different origin, wherein at least one portion is of human origin. Accordingly, one embodiment relates to a deimmunized antibody having binding specificity for an EphB4 (e.g., human EphB4), said antibody comprising an antigen binding region of nonhuman origin (e.g., rodent) and at least a portion of an antibody of human origin (e.g., a human framework region, a human constant region or portion thereof). For example, the deimmunized antibody can comprise portions derived from an antibody of nonhuman origin with the requisite specificity, such as a mouse, and from antibody sequences of human origin (e.g., a chimeric antibody), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain).

In certain embodiments, the framework regions are derived from the closest human germline framework regions. In certain embodiments, the antibody or antigen binding fragment comprises the FR1, FR2, FR3, and FR4 regions from the closest human germline gene. In certain embodiments each framework region is independently selected from the human germline gene closest to the particular framework region. In certain embodiments, residues that affect antigen binding affinity in the framework regions are substituted with the corresponding residues from the nonhuman or parent antibody.

In one aspect a deimmunized antibody or antigen binding fragment contains one or more antibody chains comprising a CDR of nonhuman origin (e.g., one or more CDRs derived from an antibody of nonhuman origin) and a framework region derived from a light and/or heavy chain of human origin, e.g., germline antibody genes (e.g., CDR-grafted antibodies with or without framework changes). In one embodiment, the deimmunized antibody can compete with murine monoclonal antibody for binding to an EphB4 polypeptide. Chimeric or CDR-grafted single chain antibodies are also encompassed by the term humanized antibody.

In one aspect a deimmunized antibody or antigen binding fragment contains one or more antibody chains comprising a CDR of nonhuman origin (e.g., one or more CDRs derived from an antibody of nonhuman origin) and a framework region of nonhuman origin. In one embodiment the nonhuman framework region is substituted with at least one amino acid from a corresponding human framework region. In one embodiment, the substitution of a human amino acid residue for a nonhuman residue reduces the immunogenicity of the antibody in a human subject.

In one embodiment, a deimmunized antibody or antigen binding fragment thereof is provided that binds the extracellular domain of EphB4, including a heavy chain variable region and a light chain variable region, wherein each variable region has between 2 to 20 amino acid substitutions in comparison to a nonhuman or parent antibody that binds the extracellular domain of EphB4. The variable region encompasses three CDR regions interspersed with four framework regions. In one aspect the substitutions are in the framework region.

In one embodiment, a nonhuman or parent antibody is compared to a database of human germine antibody genes, such as from V BASE, and highly homologous individual framework regions are identified. Structural models may be generated of the nonhuman or parent antibody variable region using such programs as SwissPdb, WAM (Web Antibody Modelling), and AbM. Residues, such as those, for example, that do not play a role in interacting with CDRs or antigen or contribute to antigen binding affinity, may be substituted by the corresponding residue from the human germline gene.

In one embodiment, the individual framework regions, instead of the whole framework, in the variable region amino acid sequence of the nonhuman or parent antibody are compared to corresponding sequences in a collection of human antibodies. The human framework with the highest degree of homology is selected to replace the original framework of the nonhuman or parent antibody. This technique, known as "framework patching", is described in detail in US Patent Application No. US 2005/0033028, which is hereby incorporated by reference.

In one embodiment, referred to as "framework shuffling", a combinatorial library with CDR variable regions from the nonhuman or parent antibody are fused in frame into a pool of individual human germline frameworks (Dall'Acqua et al., Methods, 36:43 (2005)). The libraries are then screened to identify clones that encode humanized antibodies which bind the extracellular domain of EphB4 with similar or greater binding affinity compared to the nonhuman or parent antibody.

In one embodiment, the nonhuman or parent antibody is analyzed in order to identify potential T-cell epitopes. T-cell epitopes can be identified using peptide threading software that predicts MCH class II binding motifs. Computational binding prediction algorithms include iTope™, Tepitope, SYFPEITHI, and MHCpred. In one embodiment, homologous individual human framework regions are analyzed for potential T-cell epitopes in parallel. Epitopes that are identified in both the nonhuman or parent variable region and the human germline genes may be disregarded. Epitopes identified in only the nonhuman or parent variable region are then flagged for potential replacement.

In one embodiment, the nonhuman or parent antibody is analyzed in order to identify potential B-cell epitopes. Potential B-cell epitopes can be recognized by identifying residues in the non-human or parent antibody framework region that are at least partially solvent accessible and differ from corresponding homologous human antibody framework residues. In one embodiment, potential B-cell epitopes are eliminated by replacing the solvent accessible nonhuman or parent antibody framework residues with corresponding human residues.

In one embodiment substitutions introduced into the deimmunized antibody comprise amino acid substitutions, deletions or insertions. In one embodiment, each substitution results in the replacement of one amino acid with the corresponding amino acid from a homologous human germline gene or from a human variable region consensus sequence. In one embodiment, a nonhuman or parent antibody or antigen binding fragment is deimmunized by substituting from 2 to 20 amino acids with corresponding amino acids from a homologous human germline gene or from a human variable region consensus sequence. In one embodiment, the substitutions may remove one or more T-cell or B-cell epitopes. In another embodiment, the substitutions may introduce a regulatory T-cell epitope. In one embodiment, the deimmunized nonhuman or parent antibody or antigen binding fragment demonstrates a reduced immunogenicity response over the nonhuman or parent antibody or antigen binding fragment when administered to a human subject.

In one embodiment, the heavy and light chain variable regions of the deimmunized antibody or antigen binding fragment are derived entirely from one or more human antibodies, as described in WO2006/08246. In one embodiment, the variable regions are composed of segments of amino acid sequence from one or more human antibodies. In one embodiment the human segments are two or more amino acids in length. In one embodiment, the human segments are 100 or fewer amino acids in length. In further embodiments, the human segments are 50 or fewer, 40 or fewer, or 30 or fewer amino acids in length.

In one embodiment, each variable region has a reduced number of T-cell epitopes compared to the parent or nonhuman antibody. In one embodiment, each variable region has a reduced number of B-cell epitopes compared to the parent or nonhuman antibody.

In one aspect, the deimmunized antibody or antigen binding fragment comprises the CDR regions of mouse monoclonal antibody #47. Mouse monoclonal antibody #47 has been described and characterized in US2005/0249736, which is hereby incorporated by reference in its entirety. The CDR regions for the heavy chain of mouse monoclonal antibody #47 are defined as SEQ ID NO:19 (CDR1), SEQ ID NO:20 (CDR2), and SEQ ID NO:21 (CDR3). The CDR regions for the light chain of mouse monoclonal antibody #47 are defined as SEQ ID NO:22 (CDR1), SEQ ID NO:23 (CDR2), and SEQ ID NO:24 (CDR3). In one aspect, the deimmunized antibody or antigen binding fragment comprises one or more framework regions (FR1-FR4) of mouse monoclonal antibody #47.

In one aspect the deimmunized antibody or antigen binding fragment is less immunogenic (or rather, elicits a reduced HAMA response) than mouse monoclonal antibody #47 in a human subject. Assays to determine immunogenicity are well within the knowledge of the skilled person. Art-recognized methods of determining immune response can be performed to monitor a HAMA response in a particular subject or during clinical trials. Subjects administered deimmunized antibodies can be given an immunogenicity assessment at the beginning and throughout the administration of said therapy. The HAMA response is measured, for example, by detecting antibodies to the deimmunized therapeutic reagent, in serum samples from the subject using a method known to one in the art, including surface plasmon resonance technology (BIACORE) and/or solid-phase ELISA analysis. Alternatively, in vitro assays designed to measure a T-cell activation event are also indicative of immunogenicity. One assay, by way of example, is the T-cell proliferation assay. In this assay PBMCs from donors representing >80% of HLA-DR alleles in the world are screened for proliferation in response to an antibody or antibody fragment.

In one aspect the deimmunized antibody or antigen binding fragment binds the extracellular domain of EphB4 with a binding affinity which is at least 80% or at least 90% of the binding affinity of mouse monoclonal antibody #47. In another embodiment, the deimmunized antibody or antigen binding fragment binds the extracellular domain of EphB4 with a binding affinity which is at least 100%, or rather with a greater binding affinity than mouse monoclonal antibody #47.

The determination of binding affinity is well within the knowledge of a skilled person. Art recognized methods include enzyme-linked immunosorbent assays (ELISAs), radioimmunoprecipitation (RIP) assays, and the BIAcore biosensor assay. Example 2 describes in more detail the determination of binding affinity using the sandwich ELISA.

In another aspect, the deimmunized antibody or antigen binding fragment comprises a heavy chain that comprises an amino acid sequence defined as SEQ ID NO:1, SEQ ID NO:2, SEQ ID NO:3, SEQ ID NO:4, or SEQ ID NO:5 and a light chain that comprises an amino acid sequence defined as SEQ ID NO:6, SEQ ID NO:7, SEQ ID NO:8, or SEQ ID NO:9. In one embodiment the heavy chain is SEQ ID NO:3 and the light chain is SEQ ID NO:7. In one embodiment the heavy chain is SEQ ID NO:3 and the light chain is SEQ ID NO:8. In one embodiment the heavy chain is SEQ ID NO:4 and the light chain is SEQ ID NO:7. In one embodiment the heavy chain is SEQ ID NO:4 and the light chain is SEQ ID NO:8. In some of the embodiments the deimmunized antibody or antigen binding fragment binds to the extracellular domain of EphB4. In some of the embodiments the deimmunized antibody or antigen binding fragment is less immunogenic to a human subject than the mouse monoclonal antibody #47.

In one aspect, the deimmunized antibody or antigen binding fragment comprises the CDR regions of mouse monoclonal antibody #131. Mouse monoclonal antibody #131 has been described and characterized in US2005/0249736, which is hereby incorporated by reference in its entirety. The CDR regions for the heavy chain of mouse monoclonal antibody #131 are defined as SEQ ID NO:25 (CDR1), SEQ ID NO:26 (CDR2), and SEQ ID NO:27 (CDR3). The CDR regions for the light chain of mouse monoclonal antibody #131 are defined as SEQ ID NO:28 (CDR1), SEQ ID NO:29 (CDR2), and SEQ ID NO:30 (CDR3). In one aspect, the deimmunized antibody or antigen binding fragment comprises one or more framework regions (FR1-FR4) of mouse monoclonal antibody #131.

In one aspect the deimmunized antibody or antigen binding fragment binds the extracellular domain of EphB4 with a binding affinity which is at least 80% or at least 90% of the binding affinity of mouse monoclonal antibody #131. In another embodiment, the deimmunized antibody or antigen binding fragment binds the extracellular domain of EphB4 with a binding affinity which is at least 100%, or rather with a greater binding affinity than mouse monoclonal antibody #131.

In one aspect the deimmunized antibody or antigen binding fragment is less immunogenic (or rather, elicits a reduced HAMA response) than mouse monoclonal antibody #131 in a human subject.

In another aspect, the deimmunized antibody or antigen binding fragment comprises a heavy chain that comprises an amino acid sequence defined as SEQ ID NO:10, SEQ ID NO:11, SEQ ID NO:12, SEQ ID NO:13, or SEQ ID NO:14 and a light chain that comprises an amino acid sequence defined as SEQ ID NO:15, SEQ ID NO:16, SEQ ID NO:17, or SEQ ID NO:18. In one embodiment the heavy chain is SEQ ID NO:13 and the light chain is SEQ ID NO:17. In one embodiment the heavy chain is SEQ ID NO:13 and the light chain is SEQ ID NO:18. In one embodiment the heavy chain is SEQ ID NO:14 and the light chain is SEQ ID NO:17. In one embodiment the heavy chain is SEQ ID NO:14 and the light chain is SEQ ID NO:18. In some of the embodiments the deimmunized antibody or antigen binding fragment binds to the extracellular domain of EphB4. In some of the embodiments the deimmunized antibody or antigen binding fragment is less immunogenic to a human subject than the mouse monoclonal antibody #131.

In some embodiments, the deimmunized antibodies inhibit the formation of tubes by cultured endothelial cells. Inhibition can be determined by any method known to a person skilled in the art, including the following. Matrigel (60 µl of 10 mg/ml; Collaborative Lab, Cat. No. 35423) is placed in each well of an ice-cold 96-well plate. The plate is allowed to sit at room temperature for 15 minutes then incubated at 37°

C. for 30 minutes to permit Matrigel to polymerize. In the mean time, human umbilical vein endothelial cells are prepared in EGM-2 (Clonetic, Cat. No. CC3162) at a concentration of $2 \times 10^5$ cells/ml. The deimmunized antibody or antigen binding fragment is prepared at 2x the desired concentration (5 concentration levels) in the same medium. Cells (500 µl) and 2x antibody (500 µl) were mixed and 200 µl of this suspension is placed in duplicate on the polymerized Matrigel. After 24 h incubation, triplicate pictures are taken for each concentration using a Bioquant Image Analysis system. Protein addition effect ($IC_{50}$) is assessed compared to untreated controls by measuring the length of cords formed and number of junctions.

In some embodiments, the deimmunized antibody or antigen binding fragment inhibits the vascularization of a tissue in vivo. Inhibition can be determined by any method known to a person skilled in the art, including the following. In vivo angiogenesis can be assayed in mice as growth of blood vessels from subcutaneous tissue into a Matrigel plug containing the deimmunized antibody or antigen binding fragment. Matrigel rapidly forms a solid gel at body temperature, trapping the factors to allow slow release and prolonged exposure to surrounding tissues. Matrigel (8.13 mg/ml, 0.5 ml) in liquid form at 4° C. is mixed with Endothelial Cell Growth Supplement (ECGS), deimmunized antibody plus ECGS or Matrigel plus vehicle alone (PBS containing 0.25% BSA). Matrigel (0.5 ml) is injected into the abdominal subcutaneous tissue of female nu/nu mice (6 wks old) along the peritoneal mid line. At day 6, mice are sacrificed and plugs are recovered and processed for histology. Typically the overlying skin is removed, and gels are cut out by retaining the peritoneal lining for support, fixed in 10% buffered formalin in PBS and embedded in paraffin. Sections of 3 µm are cut and stained with H&E or Masson's trichrome stain and examined under light microscope In some embodiments, the deimmunized antibody or antigen binding fragment decreases the growth of a human tumor xenograft in a mouse. Inhibition of tumor growth can be determined by any method known to a person skilled in the art, including the methods described in the examples.

In some embodiments, the deimmunized antibody or antigen binding fragment inhibits the vascularization of tissue implanted into the cornea of an animal. Inhibition can be determined by any method known to a person skilled in the art, including the mouse corneal micropocket assays performed according to that detailed by Kenyon et al., 1996. (see US publication 2005/0249736 which is hereby incorporated by reference)

In some embodiments, the deimmunized antibody or antigen binding fragment promotes apoptosis. Apoptosis can be examined in vitro using various methods including TUNEL staining and the Cell Death Detection ELISAplus Kit (Roche, Piscataway, N.J.).

In certain aspects, the present application provides the hybridoma cell lines, as well as to the monoclonal antibodies produced by these hybridoma cell lines. The cell lines disclosed have uses other than for the production of the monoclonal antibodies. For example, the cell lines can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-EphB4 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-EphB4 light or heavy chain can be isolated (e.g., by PCR) or cDNA libraries can be prepared from mRNA isolated from the cell lines, and cDNA clones encoding an anti-EphB4 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host T-cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host T-cell by an appropriate method (e.g., transformation, transfection, electroporation, infection), such that the nucleic acid is operably linked to one or more expression control elements (e.g., in the vector or integrated into the host T-cell genome). For production, host T-cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host T-cells or medium). It will be appreciated that the method of production encompasses expression in a host T-cell of a transgenic animal (see e.g., WO 92/03918, GenPharm International, published Mar. 19, 1992).

The present antibodies and antigen binding fragments can be utilized to directly kill or ablate cancerous cells in vivo. Direct killing involves administering the antibodies (which are optionally fused to a cytotoxic drug) to a subject requiring such treatment. In some embodiments, the cancer comprises cancer cells expressing EphB4 at a higher level than noncancerous cells of a comparable tissue. Since the antibodies recognize EphB4 on cancer cells, any such cells to which the antibodies bind are destroyed. Where the antibodies are used alone to kill or ablate cancer cells, such killing or ablation can be effected by initiating endogenous host immune functions, such as CDC and/or ADCC. Assays for determining whether an antibody kills cells in this manner are within the purview of those skilled in the art.

Accordingly in one embodiment, the antibodies of the present disclosure may be used to deliver a variety of cytotoxic compounds. Any cytotoxic compound can be fused to the present antibodies. The fusion can be achieved chemically or genetically (e.g., via expression as a single, fused molecule). The cytotoxic compound can be a biological, such as a polypeptide, or a small molecule. As those skilled in the art will appreciate, for small molecules, chemical fusion is used, while for biological compounds, either chemical or genetic fusion can be employed.

Non-limiting examples of cytotoxic compounds include therapeutic drugs, a compound emitting radiation, molecules of plant, fungal, or bacterial origin, biological proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Procedures for conjugating the antibodies with the cytotoxic agents have been previously described and are within the purview of one skilled in the art.

In certain embodiments, the antibodies or antigen binding fragments are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}K$, $^{52}Fe$, $^{57}Co$, $^{67}Cu$, $^{67}Ga$, $^{68}Ga$, $^{123}I$, $^{125}I$, $^{131}I$, $^{132}I$, or $^{99}Tc$. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography.

Immunoscintigraphy using antibodies or other binding polypeptides directed at EphB4 may be used to detect and/or diagnose cancers and vasculature. For example, monoclonal antibodies against the EphB4 marker labeled with $^{99}$Technetium, $^{111}$Indium, $^{125}$Iodine—may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, or 1-10 millicuries, or 2-5 millicuries are administered. Thus, the compositions disclosed are useful as imaging agents comprising a targeting moiety conjugated to a radioactive moiety comprise 0.1-100 millicuries, in some embodiments 1-10 millicuries, in some embodiments 2-5 millicuries, in some embodiments 1-5 millicuries.

The application further provides polynucleotides comprising a nucleotide sequence encoding a deimmunized anti-EphB4 antibody or fragments thereof. Because of the degeneracy of the genetic code, a variety of nucleic acid sequences encode each antibody amino acid sequence. The application further provides polynucleotides that hybridize under stringent or lower stringency hybridization conditions, e.g., as defined herein, to polynucleotides that encode a deimmunized antibody that binds to hEphB4.

Stringent hybridization conditions include, but are not limited to, hybridization to filter-bound DNA in 6x sodium chloride/sodium citrate (SSC) at about 45° C. followed by one or more washes in 0.2xSSC/0.1% SDS at about 50-65° C., highly stringent conditions such as hybridization to filter-bound DNA in 6xSSC at about 45° C. followed by one or more washes in 0.1xSSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR. In one embodiment, the codons that are used comprise those that are typical for human or mouse (see, e.g., Nakamura, Y., Nucleic Acids Res. 28: 292 (2000)).

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

The present application also provides polynucleotide sequences encoding heavy and light chain framework regions and CDRs of antibodies described herein as well as expression vectors for their efficient expression in mammalian cells.

IV. Anti-Eph4B Antibodies with Altered Effector Functions

Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where Eph4B is expressed in normal tissue, for example; deimmunized antibodies and antigen binding fragments without effector function in these instances may elicit the desired therapeutic response while not damaging normal tissue. In another embodiment, antibodies or antigen binding fragments are provided with increased effector function, and may therefore be useful for direct cell killing.

Accordingly, certain aspects and methods of the present disclosure relate to anti-Eph4B antibodies with altered effector functions that comprise one or more amino acid substitutions, insertions, and/or deletions. In certain embodiments, such a variant anti-Eph4B antibody exhibits reduced or no effector function.

Anti-Eph4B antibodies with reduced effector function may be produced by introducing other types of changes in the amino acid sequence of certain regions of the antibody. Such amino acid sequence changes include but are not limited to the Ala-Ala mutation described by Bluestone et al. (see WO 94/28027 and WO 98/47531; also see Xu et al. 2000 Cell Immunol 200; 16-26). Thus in certain embodiments, anti-Eph4B antibodies with mutations within the constant region including the Ala-Ala mutation may be used to reduce or abolish effector function. According to these embodiments, the constant region of an anti-Eph4B antibody comprises a mutation to an alanine at position 234 or a mutation to an alanine at position 235. Additionally, the constant region may contain a double mutation: a mutation to an alanine at position 234 and a second mutation to an alanine at position 235. In one embodiment, the anti-Eph4B antibody comprises an IgG4 framework, wherein the Ala-Ala mutation would describe a mutation(s) from phenylalanine to alanine at position 234 and/or a mutation from leucine to alanine at position 235. In another embodiment, the anti-anti-Eph4B antibody comprises an IgG1 framework, wherein the Ala-Ala mutation would describe a mutation(s) from leucine to alanine at position 234 and/or a mutation from leucine to alanine at position 235. An anti-anti-Eph4B antibody may alternatively or additionally carry other mutations, including the point mutation K322A in the CH2 domain (Hezareh et al. 2001 J Virol. 75: 12161-8). An antibody with said mutation(s) in the constant region may furthermore be a blocking or non-blocking antibody.

Changes within the hinge region also affect effector functions. For example, deletion of the hinge region may reduce affinity for Fc receptors and may reduce complement activation (Klein et al. 1981 Proc Natl Acad Sci USA. 78: 524-528). The present disclosure therefore also relates to antibodies with alterations in the hinge region.

In particular embodiments, anti-Eph4B antibodies may be modified to either enhance or inhibit complement dependent cytotoxicity (CDC). Modulated CDC activity may be achieved by introducing one or more amino acid substitutions, insertions, or deletions in an Fc region of the antibody (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., J. Exp Med. 176:1191-1195 (1992) and Shopes, B. J. Immunol. 148:2918-2922 (1992), WO99/51642, Duncan & Winter Nature 322: 738-40 (1988); U.S. Pat. No. 5,648,260; U.S. Pat. No. 5,624,821; and WO94/29351. Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

Another potential means of modulating effector function of antibodies includes changes in glycosylation. This topic has been recently reviewed by Raju who summarized the proposed importance of the oligosaccharides found on human IgGs with their degree of effector function (Raju, T S. BioProcess *International* April 2003. 44-53). According to Wright and Morrison, the microheterogeneity of human IgG oligosaccharides can affect biological functions such as CDC and ADCC, binding to various Fc receptors, and binding to C1q protein (Wright A. & Morrison S L. TIBTECH 1997, 15: 26-32). It is well documented that glycosylation patterns of antibodies can differ depending on the producing cell and the cell culture conditions (Raju, T S. BioProcess *International* April 2003. 44-53). Such differences can lead to changes in both effector function and pharmacokinetics (Israel et al. *Immunology*. 1996; 89(4):573-578; Newkirk et al. *P. Clin. Exp.* 1996; 106(2):259-64). Differences in effector function may be related to the IgGs ability to bind to the Fcγ receptors (FcγRs) on the effector cells. Shields, et al., have shown that IgG, with variants in amino acid sequence that have improved binding to FcγR, can exhibit up to 100% enhanced ADCC using human effector cells (Shields et al. *J Biol Chem.* 2001 276(9):6591-604). While these variants include changes in amino acids not found at the binding interface, both the nature of the sugar component as well as its structural pattern may also contribute to the differences observed. In addition, the presence or absence of fucose in the oligosaccharide component of an IgG can improve binding and ADCC (Shields et al. *J Biol Chem.* 2002; 277(30):26733-40). An IgG that lacked a fucosylated carbohydrate linked to $Asn^{297}$ exhibited normal receptor binding to the Fcγ receptor. In contrast, binding to the FcγRIIA receptor was improved 50% and accompanied by enhanced ADCC, especially at lower antibody concentrations.

Work by Shinkawa, et al., demonstrated that an antibody to the human IL-5 receptor produced in a rat hybridoma showed more than 50% higher ADCC when compared to the antibody produced in Chinese hamster ovary cells (CHO) (Shinkawa et al. *J Biol Chem.* 2003 278(5):3466-73). Monosaccharide composition and oligosaccharide profiling showed that the rat hybridoma-produced IgG had a lower content of fucose than the CHO-produced protein. The authors concluded that the lack of fucosylation of an IgG1 has a critical role in enhancement of ADCC activity.

A different approach was taken by Umana, et al., who changed the glycosylation pattern of chCE7, a chimeric IgG1 anti-neuroblastoma antibody (Umana et al. *Nat Biotechnol.* 1999 February; 17(2): 176-80). Using tetracycline, they regulated the activity of a glycosyltransferase enzyme (GnnII) which bisects oligosaccharides that have been implicated in ADCC activity. The ADCC activity of the parent antibody was barely above background level. Measurement of ADCC activity of the chCE7 produced at different tetracycline levels showed an optimal range of GnTlH expression for maximal chCE7 in vitro ADCC activity. This activity correlated with the level of constant region-associated, bisected complex oligosaccharide. Newly optimized variants exhibited substantial ADCC activity. Similarly, Wright and Morrison produced antibodies in a CHO cell line deficient in glycosylation (1994 J Exp Med 180: 1087-1096) and showed that antibodies produced in this cell line were incapable of complement-mediated cytolysis. Thus as known alterations that affect effector function include modifications in the glycosylation pattern or a change in the number of glycosylated residues, the present disclosure relates to a Eph4B antibody wherein glycosylation is altered to either enhance or decrease effector function(s) including ADCC and CDC. Altered glycosylation includes a decrease or increase in the number of glycosylated residues as well as a change in the pattern or location of glycosylated residues.

Still other approaches exist for the altering effector function of antibodies. For example, antibody-producing cells can be Hypermutagenic, thereby generating antibodies with randomly altered nucleotide and polypeptide residues throughout an entire antibody molecule (see WO 2005/011735). Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s).

It is further understood that effector function may vary according to the binding affinity of the antibody. For example, antibodies with high affinity may be more efficient in activating the complement system compared to antibodies with relatively lower affinity (Marzocchi-Machado et al. 1999 Immunol Invest 28: 89-101). Accordingly, an antibody may be altered such that the binding affinity for its antigen is reduced (e.g., by changing the variable regions of the antibody by methods such as substitution, addition, or deletion of one or more amino acid residues). An anti-Eph4B antibody with reduced binding affinity may exhibit reduced effector functions, including, for example, reduced ADCC and/or CDC.

V. Method of Making Antibodies

The deimmunized antibody or antigen binding fragment that binds the extracellular domain of EphB4 can be made by a number of different methods known to a person skilled in the art. In one example, a nonhuman anti-EphB4 antibody is deimmunized to reduce the number of either T or B-cell epitopes or to introduce regulatory T-cell epitopes. The starting nonhuman or parent anti-EphB4 antibody can be modified; for example, it can be any form of a chimeric, humanized, or primatized antibody. Alternatively, the starting nonhuman or parent anti-EphB4 antibody is de-immunized without a humanization or primatization step.

Nonhuman EphB4 Antibodies

Anti-EphB4 antibodies are known to those skilled in the art and include, for example, the antibodies described in U.S. Pat. No. 5,635,177 and US publications 2006/0134118 and 2005/0249736. Each of these documents is incorporated herein.

Methods of generating novel anti-EphB4 antibodies are also known to those skilled in the art. For example, a method for generating a monoclonal antibody that binds specifically to an EphB4 polypeptide may comprise administering to a mouse an amount of an immunogenic composition comprising the EphB4 polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the EphB4 polypeptide. Once obtained, a hybridoma can be propagated in a cell culture, optionally in culture conditions where the hybridoma-derived cells produce the monoclonal antibody that binds specifically to EphB4 polypeptide. The monoclonal antibody may be purified from the cell culture.

In addition, the techniques used to screen antibodies in order to identify a desirable antibody may influence the properties of the antibody obtained. A variety of different techniques are available for testing antibody:antigen interactions to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays and immunohistochemistry.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. USA, 90: 2551-2555 (1993); Jakobovits et al., Nature, 362: 255-258 (1993); Lonberg et al., U.S. Pat. No. 5,545,806; Surani et al., U.S. Pat. No. 5,545,807.

Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

The application provides antigen binding fragments capable of binding to an EphB4 receptor or portion thereof, including, but not limited to, Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH1 domain and hinge region of the heavy chain.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

Methods for humanizing antibodies have been described in the art. In some embodiments, a humanized antibody has one or more amino acid residues introduced from a source that is nonhuman, in addition to the nonhuman CDRs. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable region has been substituted by the corresponding sequence from a nonhuman species. In practice, humanized antibodies are typically human antibodies in which some hypervariable region residues and possibly some framework region residues are substituted by residues from analogous sites in rodent antibodies.

U.S. Pat. No. 5,693,761 to Queen et al, discloses a refinement on Winter for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 .angstrom. of any CDR residue.

In other approaches, the importance of particular framework amino acid residues is determined experimentally once a low-avidity humanized construct is obtained, by reversion of single residues to the mouse sequence and assaying antigen binding as described by Riechmann et al, (1988). Another example approach for identifying important amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43 (2005)). The libraries are then screened to identify clones that encode humanized antibodies which retain good binding.

The choice of human variable regions, both light and heavy, to be used in making the humanized antibodies is very important to reduce antigenicity. According to the so-called "best-fit" method, the sequence of the variable region of a rodent antibody is screened against the entire library of known human variable-domain sequences. The human sequence that is closest to that of the rodent is then accepted as the human framework region (framework region) for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chain variable regions. The same framework may be used for several different humanized antibodies (Carter et al., Proc. Natl. Acad. Sci. USA, 89:4285 (1992); Presta et al., J. Immunol., 151:2623 (1993)).

The choice of nonhuman residues to substitute into the human variable region can be influenced by a variety of factors. These factors include, for example, the rarity of the amino acid in a particular position, the probability of interaction with either the CDRs or the antigen, and the probability of participating in the interface between the light and heavy chain variable domain interface. (see for example U.S. Pat. Nos. 5,693,761, 6,632,927, and 6,639,055). One method to analyze these factors is through the use of three-dimensional models of the nonhuman and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, non-human residues can be selected and substituted for human variable region residues in order to achieve the desired antibody characteristic, such as increased affinity for the target antigen(s)

Deimmunization

The anti-EphB4 antibody or antigen binding fragment is deimmunized to render it non-immunogenic, or less immunogenic, to a given species. Deimmunization can be achieved through structural alterations to the anti-EphB4 antibody. In one embodiment, the anti-EphBr is a mouse monoclonal antibody. Any deimmunization technique known to those skilled in the art can be employed. One suitable technique, for example, for deimmunizing antibodies is described in WO 00/34317, the disclosure of which is incorporated herein in its entirety. In summary, a typical protocol within the general method described therein includes the following steps.

1. Determining the amino acid sequence of the antibody or a part thereof;
2. Identifying potential T-cell epitopes within the amino acid sequence of the antibody by any method including determination of the binding of peptides to MHC molecules, determination of the binding of peptide: HLA complexes to the T-cell receptors from the species to receive the therapeutic protein, testing of the antibody or parts thereof using transgenic animals with HLA molecules of the species to receive the therapeutic protein, or testing such transgenic animals reconstituted with immune system cells from the species to receive the therapeutic protein;
3. By genetic engineering or other methods for producing modified antibodies, altering the antibody to remove one or more of the potential T-cell epitopes and producing such an altered antibody for testing.

In one embodiment, the sequences of the variable regions of the antibody or antigen binding fragment can be analyzed for the presence of MHC class II binding motifs. For example, a comparison may be made with databases of MHC-binding motifs such as, for example by searching the "motifs" database on the worldwide web. Alternatively, MHC class II binding peptides may be identified using computational threading methods such as those devised by Altuvia et al. (J. Mol. Biol. 249 244-250 (1995)) whereby consecutive overlapping peptides from the variable region sequences are testing for their binding energies to MHC class II proteins. Computational binding prediction algorithms include iTope™, Tepitope, SYFPEITHI, and MHCpred. In order to assist the identification of MHC class H-binding peptides, associated sequence features which relate to successfully presented peptides such as amphipathicity and Rothbard motifs, and cleavage sites for cathepsin B and other processing enzymes can be searched for.

Having identified potential second species (e.g. human) T-cell epitopes, these epitopes are then eliminated by alteration of one or more amino acids, as required to eliminate the T-cell epitope. Usually, this will involve alteration of one or more amino acids within the T-cell epitope itself. This could involve altering an amino acid adjacent the epitope in terms of the primary structure of the protein or one which is not adjacent in the primary structure but is adjacent in the secondary structure of the molecule. The usual alteration contemplated will be amino acid substitution, but it is possible that in certain circumstances amino acid addition or deletion will be appropriate. All alterations can be accomplished by recombinant DNA technology, so that the final molecule may be prepared by expression from a recombinant host, for example by well established methods, but the use of protein chemistry or any other means of molecular alteration may also be used.

In practice, it has been recognized that potential human T-cell epitopes can be identified even in human germline variable region framework sequences when comparison is made with databases of MHC-binding motifs. As humans do not generally mount an ongoing immune response against their own antibodies, then either humans are tolerant to these epitopes or these potential epitopes cannot be presented by human APCs because they are not processed appropriately. Therefore, such potential T-cell epitopes which are represented in germline variable region sequences may, in practice, be retained in the deimmunized antibody.

In order to minimize the creation of additional T-cell epitopes during the elimination of potential T-cell epitopes from the therapeutic antibody sequence, the elimination of T-cell epitopes can be achieved by substituting particular amino acids which results in a conversion of the nonhuman or parental antibody (usually mouse) amino acids within T-cell epitopes to amino acids at positions corresponding to human germline amino acids at positions. Human germline sequences are disclosed in Tomlinson, I. A. et al. (1992) J. Mol. Biol. 227:776-798; Cook, G. P. et al. (1995) Immunol. Today Vol. 16 (5): 237-242; Chothia, D. et al. (1992) J. Mol. Bio. 227:799-817. The V BASE directory provides a comprehensive directory of human immunoglobulin variable region sequences (compiled by Tomlinson, I. A. et al. MRC Centre for Protein Engineering, Cambridge, UK).

In one method, a human germline sequence homologous to the nonhuman or parental sequence is identified. Alternatively, a human germline sequence homologous to each framework region (FR1-FR4) of the nonhuman or parental sequence may be identified. In one method, the nonhuman or parental sequence and the homologous human germline sequence are analyzed in parallel for MHC class II binding peptides. Regions can be identified where the MHC class II binding profile differ between the nonhuman or parental sequence and a human germline sequence. Amino acids in these regions of the nonhuman or parental sequence can be selected for conversion to a corresponding human amino acid.

Once identified T-cell epitopes are removed, the deimmunized sequence may be analyzed again to ensure that new T-cell epitopes have not been created and, if they have, the epitope(s) can be deleted, as described above; or the previous conversion to a corresponding human germline amino acid is altered by conversion of the nonhuman or parental amino acid to a corresponding human amino acid until all T-cell epitopes are eliminated.

Not all T-cell epitopes identified computationally need to be removed. A person skilled in the art will appreciate the significance of the "strength" or rather potential immunogenicity of particular epitopes. The various computational methods generate scores for potential epitopes. A person skilled in the art will recognize that only the high scoring epitopes may need to be removed. A skilled person will also recognize that there is a balance between removing potential epitopes and maintaining the original nonhuman variable region sequence, which may affect antigen binding. Therefore, one strategy is to sequentially introduce substitutions into the nonhuman or parent antibody and then test for antigen binding and immunogenicity.

For the CDRs of a therapeutic antibody, it is common for one or more potential T-cell epitopes to overlap or fall within the CDRs whereby removal of the epitopes requires alteration of residues within the CDRs. In order to eliminate the induction of a T-cell response to such epitopes, it may be desirable to eliminate these although this may reduce the binding affinity of the resultant antibody and thus any potential alteration of CDRs may need to be tested for any alteration of resultant antigen binding.

In one embodiment, the sequence of the deimmunized antibodies has been altered to remove one or more B-cell epitopes. For removal of human B-cell epitopes the "veneering" or "resurfacing" method of Padlan (Padlan E. A., Molecular Immunology 28 489-498 (1991) and EP-A-0519596) may be utilized. There are two general steps in veneering a nonhuman antigen-binding site. Initially, the framework regions of the variable regions of an antibody molecule of interest are compared with corresponding framework region sequences of available human variable region databases. The most homologous human variable regions are then compared residue by residue to corresponding non-human amino acids. The residues in the non-human framework region that differ from the human counterpart are replaced by the residues present in the human moiety using recombinant techniques well known in the art. Residue switching is carried out with moieties that are at least partially exposed (solvent accessible), and care is exercised in the replacement of amino acid residues that may have a significant effect on the tertiary structure of variable region domains, such as proline, glycine and charged amino acids. The replacement of exterior residues generally has little, or no, effect on the interior domains, or on the interdomain contacts. (See, e.g., U.S. Pat. No. 6,797, 492).

In this manner, the resultant "veneered" non-human antigen-binding sites are thus designed to retain the non-human CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the framework regions which are believed to influence the "canonical" tertiary structures of the CDR loops. These design criteria are then used to prepare recombinant nucleotide sequences that combine the CDRs of both the heavy and light chain of a non-human antigen-binding site into human-appearing framework regions that can be used to transfect mammalian cells for the expression of recombinant human antibodies that exhibit the antigen specificity of the non-human antibody molecule.

In one embodiment, regulatory T-cell epitopes are introduced into the antibody or antigen binding fragments. WO06/082406, which is hereby incorporated by reference, describes a method of producing antibodies wherein the antibody variable regions have been modified to introduce regulatory T-cell epitopes, which in turn stimulate CD4+CD25+ T-cells and induce the secretion of inhibitory cytokines, thereby reducing immunogenicity (see, e.g., Prakken B J, et al. Proc Natl Acad Sci USA 94: 3284-3289 (1997).

Construction of Antibodies or Antigen Binding Fragments

In general, the construction of the antibodies disclosed herein is achieved using recognized manipulations utilized in genetic engineering technology. For example, techniques for isolating DNA, making and selecting vectors for expressing the DNA, purifying and analyzing nucleic acids, specific methods for making recombinant vector DNA (e.g. PCR), cleaving DNA with restriction enzymes, ligating DNA, introducing DNA, including vector DNA, into host cells by stable or transient means, culturing the host cells in selective or non-selective media, to select and maintain cells that express DNA, are generally known in the field.

Such deimmunized immunoglobulins can be produced using synthetic and/or recombinant nucleic acids to prepare genes (e.g., cDNA) encoding the desired deimmunized chain. For example, nucleic acid (e.g., DNA) sequences coding for deimmunized variable regions can be constructed using PCR mutagenesis methods to alter DNA sequences encoding a deimmunized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

Several possible vector systems are available for the expression of cloned heavy chain and light chain genes in mammalian cells. One class of vectors relies upon the integration of the desired gene sequences into the host cells genome. Cells which have stably integrated DNA can be selected by simultaneously introducing drug resistance genes such as *E. coli* gpt (Mulligan, R. C. and Berg, P., Proc. Natl. Acad. Sci., USA, 78: 2072 (1981)) or Tn5 neo (Southern, P. J. and Berg, P., J. Mol. Appl. Genet., 1: 327 (1982)). The selectable marker gene can be either linked to the DNA gene sequences to be expressed, or introduced into the same cell by co-transfection (Wigler, M. et al., Cell, 16: 77 (1979)). A second class of vectors utilizes DNA elements which confer autonomously replicating capabilities to an extrachromosomal plasmid. These vectors can be derived from animal viruses, such as bovine papillomavirus (Sarver, N. et al., Proc. Natl. Acad. Sci., USA, 79: 7147 (1982)), polyoma virus (Deans, R. J. et al., Proc. Natl. Acad. Sci., USA, 81: 1292 (1984)), or SV40 virus (Lusky, M. and Botchan, M., Nature, 293: 79 (1981)).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters enhancers, and termination signals. cDNA expression vectors incorporating such elements include those described by Okayama, H. and Berg, P., Mol. Cell Biol., 3: 280 (1983); Cepko, C. L. et al., Cell, 37: 1053 (1984); and Kaufman, R. J., Proc. Natl. Acad. Sci., USA, 82: 689 (1985).

The variable sequence can, optionally, be fused to a human constant region, e.g., human IgG1 or .kappa. constant regions. The recombinant deimmunized antibody or antigen binding fragment can be transfected into a suitable host cell for expression, for example, NS0 or CHO cells, to produce complete recombinant antibodies.

VI. Diagnostic Applications

The antibodies and antigen binding fragments are useful in a variety of applications, including research, diagnostic and therapeutic applications. For instance, they can be used to isolate and/or purify receptor or portions thereof, and to study receptor structure (e.g., conformation) and function.

In certain aspects, the various antibodies disclosed can be used to detect or measure the expression of EphB4 receptor, for example, on endothelial cells (e.g., venous endothelial cells), or on cells transfected with an EphB4 receptor gene. Thus, they also have utility in applications such as cell sorting and imaging (e.g., flow cytometry, and fluorescence activated cell sorting), for diagnostic or research purposes.

In certain embodiments, the antibodies or antigen binding fragments can be labeled or unlabeled for diagnostic purposes. Typically, diagnostic assays entail detecting the formation of a complex resulting from the binding of an antibody to EphB4. The antibodies can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the antibodies can be used in assays, such as agglutination assays. Unlabeled antibodies can also be used in combination with another (one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

In one embodiment, the antibodies and antibody fragments can be utilized in enzyme immunoassays, wherein the subject antibodies, or second antibodies, are conjugated to an enzyme. When a biological sample comprising an EphB4 protein is combined with the subject antibodies, binding occurs between the antibodies and EphB4 protein. In one embodiment, a sample containing cells expressing an EphB4 protein (e.g., endothelial cells) is combined with the subject antibodies, and binding occurs between the antibodies and cells bearing an EphB4 protein comprising an epitope recognized by the antibody. These bound cells can be separated from unbound reagents and the presence of the antibody-enzyme conjugate specifically bound to the cells can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

In certain aspects, kits for use in detecting the presence of an EphB4 protein in a biological sample can also be prepared. Such kits will include an antibody which binds to an EphB4 protein or portion of said receptor, as well as one or more ancillary reagents suitable for detecting the presence of a complex between the antibody and EphB4 or portion thereof. The antibody compositions disclosed can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the antibody or antigen binding fragment may be used in a method of detecting and/or quantitating expression of an EphB4 or portion of the receptor by a cell, wherein a composition comprising a cell or fraction thereof (e.g., membrane fraction) is contacted with an antibody which binds to an EphB4 or portion of the receptor under conditions appropriate for binding of the antibody thereto, and antibody binding is monitored. Detection of the antibody, indicative of the formation of a complex between antibody and EphB4 or a portion thereof, indicates the presence of the receptor. Binding of antibody to the cell can be determined by standard methods, such as those described in the working examples. The method can be used to detect expression of EphB4 on cells from an individual. Optionally, a quantitative expression of EphB4 on the surface of endothelial cells can be evaluated, for instance, by flow cytometry, and the staining intensity can be correlated with disease susceptibility, progression or risk.

The antibody or antigen binding fragment may also be used in a method of detecting the susceptibility of a mammal to certain diseases. To illustrate, the method can be used to detect the susceptibility of a mammal to diseases which progress based on the amount of EphB4 present on cells and/or the number of EphB4-positive cells in a mammal. In one embodiment, the application provides a method of detecting susceptibility of a mammal to a tumor. In this embodiment, a sample to be tested is contacted with an antibody which binds to an EphB4 or portion thereof under conditions appropriate for binding of said antibody thereto, wherein the sample comprises cells which express EphB4 in normal individuals. The binding of antibody and/or amount of binding is detected, which indicates the susceptibility of the individual to a tumor, wherein higher levels of receptor correlate with increased susceptibility of the individual to a tumor. Applicants and other groups have found that expression of EphB4 has a correlation with tumor growth and progression. The antibodies disclosed can also be used to further elucidate the correlation of EphB4 expression with progression of angiogenesis-associated diseases in an individual.

IIV. Therapeutic Applications

In certain embodiments, the present application provides methods of inhibiting angiogenesis and methods of treating angiogenesis-associated diseases. In some embodiments the application provides methods for promoting apoptosis. In other embodiments, the present application provides methods of inhibiting or reducing tumor growth and methods of treating an individual suffering from cancer. These methods involve administering to the individual a therapeutically effective amount of a deimmunized antibody or antigen binding fragment as described above. These methods are particularly aimed at therapeutic and prophylactic treatments of animals, and more particularly, humans. In one embodiment the antibody or antigen binding fragment used in the methods is less immunogenic when administered to a human subject than mouse monoclonal #47. In another embodiment the antibody or antigen binding fragment used in the methods is less immunogenic when administered to a human subject than mouse monoclonal #131.

The present application also provides for pharmaceutical compositions useful in treating angiogenesis-associated diseases. In some embodiments the pharmaceutical composition comprises an antibody or antigen binding fragment described herein and an acceptable pharmaceutical carrier.

The present application provides for a method of promoting apoptosis comprising contacting cells with an effective amount of a deimmunized antibody or antigen binding fragment. In some embodiments, the cells are endothelial cells.

The present application provides for a method of inhibiting angiogenesis comprising contacting endothelial cells with an effective amount of a deimmunized antibody or antigen binding fragment. In certain embodiments, said angiogenesis is induced by cancer cells. The antibody or antigen binding fragment may contact endothelial cells in vitro, ex vivo or in vivo (for example, in a subject). In still another embodiment, the antibodies inhibit the angiogenesis of cancer cells, such as for example, by at least 10%, at least 25%, at least 50%, at least 75%, or at least 90%. The inhibition of angiogenesis can be examined via in vitro cell-based assays known in the art, such as the endothelial cell tube formation assay, or in vivo animal model assays known in the art.

As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, cororany collaterals, ischemic limb angiogenesis, corneal diseases, rubeosis, arthritis, diabetic neovascularization, fractures, vasculogenesis, hematopoiesis.

It is understood that methods and compositions disclosed are also useful for treating any angiogenesis-independent cancers (tumors). As used herein, the term "angiogenesis-independent cancer" refers to a cancer (tumor) where there is no or little neovascularization in the tumor tissue.

In particular, antibody therapeutic agents disclosed are useful for treating or preventing a cancer (tumor), including, but not limited to, colon carcinoma, breast cancer, mesothelioma, prostate cancer, bladder cancer, squamous cell carcinoma of the head and neck (HNSCC), Kaposi sarcoma, ovarian cancer, and leukemia.

The present application provides for a method of inhibiting the growth of cancer cells in a subject comprising administering an effective amount of a deimmunized antibody or antigen binding fragment into the subject. The modulation may reduce or prevent the growth of the cancer cells of said subject, such as for example, by at least 10%, at least 25%, at least 50%, at least 75%, or at least 90%. As a result, where the cancer is a solid tumor, the modulation may reduce the size of the solid tumor by at least 10%, at least 25%, at least 50%, at least 75%, or at least 90%.

The inhibition of the cancer cell proliferation can be measured by cell-based assays, such as bromodeoxyuridine (BRDU) incorporation (Hoshino et al., Int. J. Cancer 38, 369 (1986); Campana et al., J. Immunol. Meth. 107:79 (1988)); [$^3$H]-thymidine incorporation (Chen, J., Oncogene 13:1395-403 (1996); Jeoung, J., J. Biol. Chem. 270:18367-73 (1995); the dye Alamar Blue (available from Biosource International) (Voytik-Harbin et al., In Vitro Cell Dev Biol Anim 34:239-46 (1998)). The anchorage independent growth of cancer cells is assessed by colony formation assay in soft agar, such as by counting the number of cancer cell colonies formed on top of the soft agar (see Examples and Sambrook et al., Molecular Cloning, Cold Spring Harbor, 1989).

The inhibition of cancer cell growth in a subject may be assessed by monitoring the cancer growth in a subject, for example in an animal model or in human subjects. One exemplary monitoring method is tumorigenicity assays. In one example, a xenograft comprises human cells from a pre-existing tumor or from a tumor cell line. Tumor xenograft assays are known in the art and described herein (see, e.g., Ogawa et al., Oncogene 19:6043-6052 (2000)). In another embodiment, tumorigenicity is monitored using the hollow fiber assay, which is described in U.S. Pat. No. 5,698,413, which is incorporated herein by reference in its entirety.

The percentage of the inhibition is calculated by comparing the cancer cell proliferation, anchorage independent growth, or cancer cell growth under modulator treatment with that under negative control condition (typically without modulator treatment). For example, where the number of cancer cells or cancer cell colonies (colony formation assay), or PRDU or [$^3$H]-thymidine incorporation is A (under the treatment of modulators) and C (under negative control condition), the percentage of inhibition would be (C−A)/C.times.100%.

In certain embodiments of such methods, one or more antibody therapeutic agents can be administered, together (simultaneously) or at different times (sequentially). In addition, antibody therapeutic agents can be administered with another type of compounds for treating cancer or for inhibiting angiogenesis.

In certain embodiments, the subject methods disclosed can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present application recognizes that the effectiveness of conventional cancer therapies (e.g., chemotherapy, radiation therapy, phototherapy, immunotherapy, and surgery) can be enhanced through the use of the antibody or antigen binding fragment.

A wide array of conventional compounds have been shown to have anti-neoplastic activities. These compounds have been used as pharmaceutical agents in chemotherapy to shrink solid tumors, prevent metastases and further growth, or decrease the number of malignant T-cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When the antibody or antigen binding fragment disclosed herein is administered in combination with another conventional anti-neoplastic agent, either concomitantly or sequentially, such antibody or antigen binding fragment may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant T-cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chloro deoxyadenosine (cladribine)); antiproliferative/antimitotic agents including natural products such as vinca alkaloids (vinblastine, vincristine, and vinorelbine), microtubule disrupters such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, TAXOL™, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenesdacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel., abciximab; antimigratory agents; antisecretory agents (breveidin); immunosuppressives (cyclosporine, tacrolimus (FX-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTor inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisolone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6573256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin $\alpha_v\beta_3$ peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462, 075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the EphB4 deimmunized antibody or antigen binding fragment may be continued while the other therapy is being administered and/or thereafter. Administration of the EphB4 deimmunized antibody or antigen binding fragment may be made in a single dose, or in multiple doses. In some instances, administration of the EphB4 deimmunized antibody or antigen binding fragment is commenced at least several days prior to the conventional therapy, while in other instances, administration is begun either immediately before or at the time of the administration of the conventional therapy.

VIII. Modes of Administration and Formulations

In certain embodiments, the EphB4 deimmunized antibody or antigen binding fragment is formulated with a pharmaceutically acceptable carrier. Such antibody or antigen binding fragment can be administered alone or as a component of a pharmaceutical formulation (composition). The antibody or antigen binding fragment may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the EphB4 deimmunized antibody or antigen binding fragment include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of anti-tumor or anti-angiogenesis therapeutic agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an EphB4 deimmunized antibody or antigen binding fragment as an active ingredient.

In solid dosage forms for oral administration (capsules, tablets, pills, dragees, powders, granules, and the like), one or more EphB4 deimmunized antibody or antigen binding fragment may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In particular, the disclosed methods can be administered topically, either to skin or to mucosal membranes such as those on the cervix and vagina. This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The EphB4 deimmunized antibody or antigen binding fragment may be mixed under sterile conditions with a pharmaceutically acceptable carrier, and with any preservatives, buffers, or propellants which may be required. The ointments, pastes, creams and gels may contain, in addition to a subject polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject polypeptide therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more EphB4 deimmunized antibodies and antigen binding fragments in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the disclosed pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more the EphB4 deimmunized antibodies and antigen binding fragments in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

Formulations for intravaginal or rectally administration may be presented as a suppository, which may be prepared by mixing one or more of the disclosed compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Pharmaceutical compositions suitable for use include compositions wherein one or more of the EphB4 deimmunized antibodies and antigen binding fragments are contained in an amount effective to achieve their intended purpose. More specifically, a therapeutically effective amount means an amount of antibody effective to prevent, alleviate or ameliorate symptoms of disease or prolong the survival of the subject being treated. Determination of a therapeutically effective amount is well within the capability of those skilled in the art, especially in light of the detailed disclosure provided herein. Therapeutically effective dosages may be determined by using in vitro and in vivo methods.

EXEMPLIFICATION

Example 1

Generation of Deimmunized Antibodies

Mouse monoclonal antibodies #47 and #131 were prepared as described in US application 2005/0249736. Briefly, anti-EphB4 monoclonal antibodies were raised in mice against the extracellular domain (ECD) of EphB4. The ECD of EphB4 was cloned into pGEX-4T-1 to generate GST-fused ECD (GST-ECD). EphB4ECD expressed as a GST fusion protein in BL21 *E. coli* was purified by affinity chromatography and the GST domain was cleaved by thrombin. Monoclonal antibody was generated by standard protocols and purified from hybridoma supernatants by Protein A chromatography. The sensitivity and specificity of the antibody was reconfirmed by Western blot with whole cell lysate of 293 cells stably transfected with EphB4. The sequences for #47 and #131 are provided in the sequence listing.

A structural model of the murine sequences was generated using Swiss Pdb in order to identify amino acids involved in antigen binding affinity. Only the Kabat and Chothia CDRs were identified.

The murine sequences were then analyzed in silico in order to identify MHC class II binding epitopes. In parallel, the closest human germline antibody gene was identified for each individual murine framework. Potential epitopes were eliminated by making a substitution in the murine sequence. The substituted residue was obtained from the homologous human germline gene. A series of variants, usually 4 or 5, was generated to test the effect of various substitutions on antigen binding affinity.

The variant variable regions were synthesized from overlapping oligonucleotides using standard methods. The variable regions were then cloned and expressed as human IgG1/kappa antibodies. All combinations of heavy chain and light chain variants were generated for #47 and #131 independently. The combinations were transiently transfected into CHO-K1 cells and the supernatants were harvested to test for activity.

Table 1 depicts the SEQ ID NOs for the parental and deimmunized variable regions. The protein and nucleotide sequences for the heavy (H) and light (K) chain variable regions (V) of the deimmunized variants are listed. The protein sequence of the variable regions of the mouse monoclonal #47 and #131 (m47, m131) antibodies as well as the individual CDRs for both the heavy (H) and light (K) chain are also listed. FIG. 2A-D also depicts an alignment of the variable regions of the mouse monoclonal parental antibody against the deimmunized variants.

TABLE 1

| SEQ ID NO: | H and K protein sequence | SEQ ID NO: | H and K nucleotide sequence | SEQ ID NO: | Protein sequence of mouse #131 and #47 |
|---|---|---|---|---|---|
| 1 | 47 HV1 | 31 | 47 HV1 | 49 | m47 heavy |
| 2 | 47 HV2 | 32 | 47 HV2 | 50 | m47 light |
| 3 | 47 HV3 | 33 | 47 HV3 | 51 | m131 heavy |
| 4 | 47 HV4 | 34 | 47 HV4 | 52 | m131 light |
| 5 | 47 HV5 | 35 | 47 HV5 | 19 | CDR1 H47 |
| 6 | 47 KV1 | 36 | 47 KV1 | 20 | CDR2 H47 |
| 7 | 47 KV2 | 37 | 47 KV2 | 21 | CDR3 H47 |
| 8 | 47 KV3 | 38 | 47 KV3 | 22 | CDR1 K47 |
| 9 | 47 KV4 | 39 | 47 KV4 | 23 | CDR2 K47 |
| 10 | 131 HV1 | 40 | 131 HV1 | 24 | CDR3 K47 |
| 11 | 131 HV2 | 41 | 131 HV2 | 25 | CDR1 H131 |
| 12 | 131 HV3 | 42 | 131 HV3 | 26 | CDR2 H131 |
| 13 | 131 HV4 | 43 | 131 HV4 | 27 | CDR3 H131 |
| 14 | 131 HV5 | 44 | 131 HV5 | 28 | CDR1 K131 |
| 15 | 131 KV1 | 45 | 131 KV1 | 29 | CDR2 K131 |
| 16 | 131 KV2 | 46 | 131 KV2 | 30 | CDR3 K131 |
| 17 | 131 KV3 | 47 | 131 KV3 | | |
| 18 | 131 KV4 | 48 | 131 KV4 | | |

Example 2

Characterization of EphB4 Binding

Figures 4A, 4B:
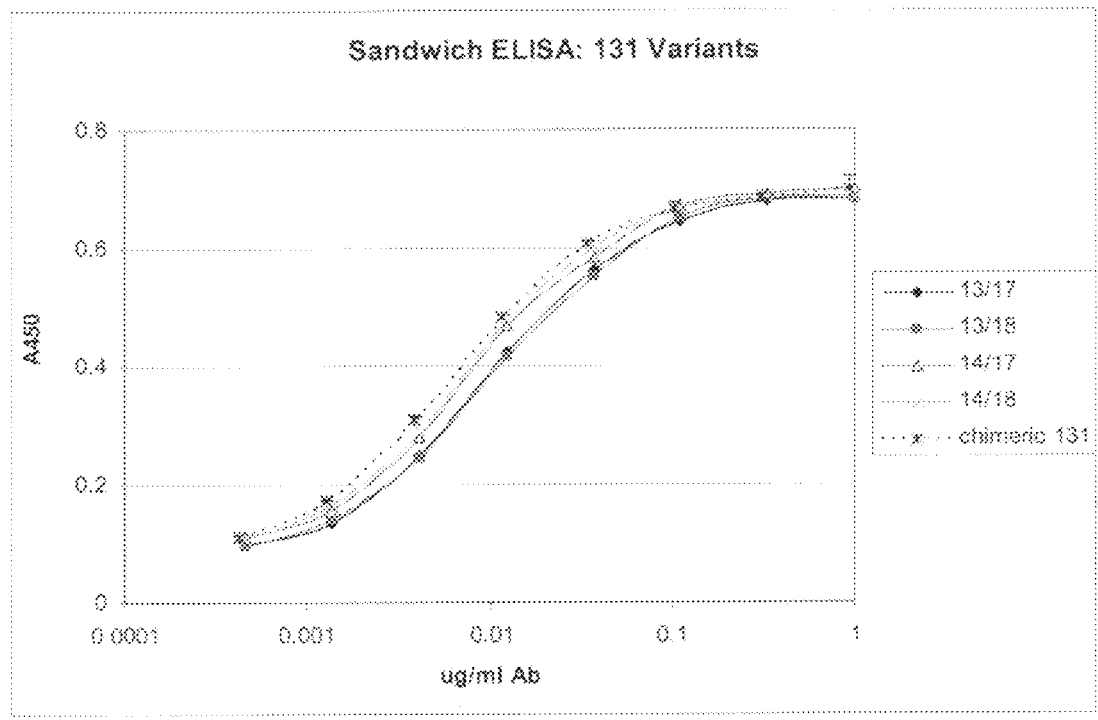
FIG. 4A depicts the results of extracellular EphB4 sandwich ELISA comparing the binding of a chimeric #131 antibody with 4 deimmunized #131 variant antibodies.
FIG. 4B shows the concentration of each antibody where 50% binding in the ELISA is reached.

The binding affinity for several of the deimmunized antibodies was determined using a standard sandwich ELISA binding assay. Briefly, plates were coated with NeutrAvidin at 2 ug/ml, followed by the addition of 1 ug/ml of biotin-labeled soluble EphB4-HSA fusion protein. Serially diluted (1:3) deimmunized #131 or #47 variants were then added, starting at a concentration of 1 ug/ml. Detection was performed using goat anti-human-Fc-HRP antibody. The data were averaged from duplicates. FIGS. 3 and 4 show graphs of the apparent binding affinities for a subset of the disclosed deimmunized antibodies. Of the 4 deimmunized #47 variants, all show similar binding affinity to a chimeric #47, while one deimmunized antibody (SEQ ID NO:3/SEQ ID NO:8) shows an improvement in binding affinity. The deimmunized #131 variants also show a similar binding affinity when compared to a chimeric #131.

Example 3

EphB4 Degradation

Figure 5:
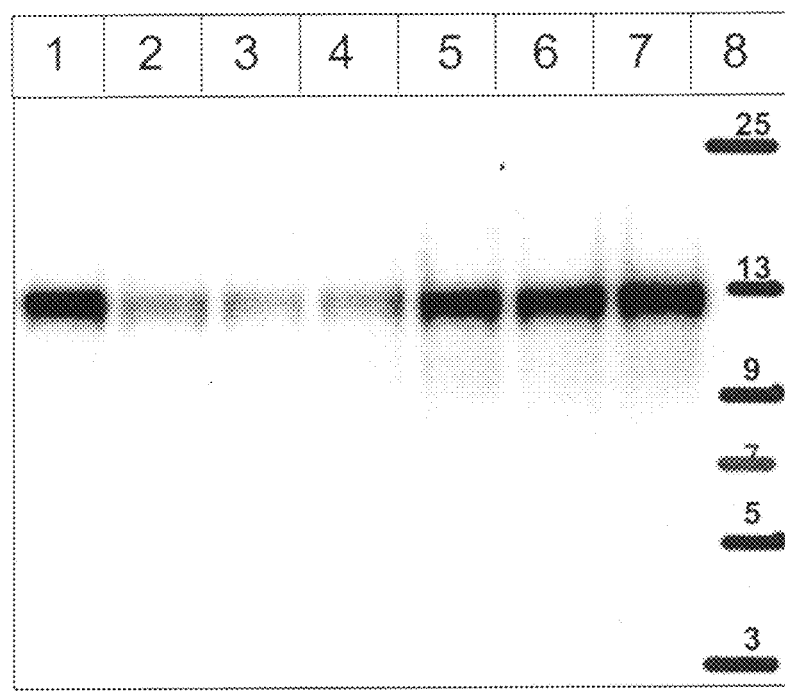
FIG. 5 shows a western blot of an SDS gel loaded with lysate from HT29 cells that were treated with 10 mg/ml of antibody (Lane 1: no antibody treatment, Lane 2: mouse monoclonal #131, Lane 3: chimeric #131, Lane 4: an exemplary deimmunized #131 antibody, Lane 5: mouse monoclonal #47, Lane 6: chimeric #47, Lane 7: and exemplary deimmunized #47 antibody, Lane 8 indicated the molecular markers with the weight in KDa). The blot was probed with an anti-EphB4 primary antibody.

HT29 cells were treated with 10 mg/ml of the indicated monoclonal antibody (Mu—murine; Ch—chimeric and Del—deimmunized) for 6 h, followed by washing with cold PBS and direct lysis into SDS-buffer. The cell lysis was run on SDS gels and Western blots were performed using an anti-EphB4 primary antibody (FIG. 5).

Example 4

In Vivo Xenograft Assay

In order to characterize the in vivo effect of the deimmunized antibodies, in vivo tumor xenograft assays were performed. Briefly, cells were propagated, collected by trypsin digestion and re-suspended in serum free medium. Approximately $2 \times 10^6$ cells were injected in the flank of ten- to twelve-week old, female Balb/C athylic mice, either SCC15 cells for a squamous cell carcinoma model or H29 cells for a colon cancer model. Tumor growth was measured three times a week and volume estimated as $0.52 \times a \times b^2$, where a and b are the largest and smallest lengths of the palpable tumor. On day 4 after cell implantation, tumor volumes were calculated to ensure uniformity in size and animals were randomly divided into three groups (n=6 mice per group). Each group was administered three times a week intraperitoneal (i.p.) injection, 10 mg/kg of the test antibodies or vehicle alone (sterile normal saline, pH 7.4). Animals were sacrificed and tumors and normal organs harvested after four weeks. A portion of the tumors was fixed in formalin for paraffin-embedding and histologic analysis. The remaining tumor tissue and organs in each group were pooled and protein extracted. All procedures were approved by our Institutional Animal Care and Use Committee and performed in accordance with the Animal Welfare Act regulations.

Figure 6A:
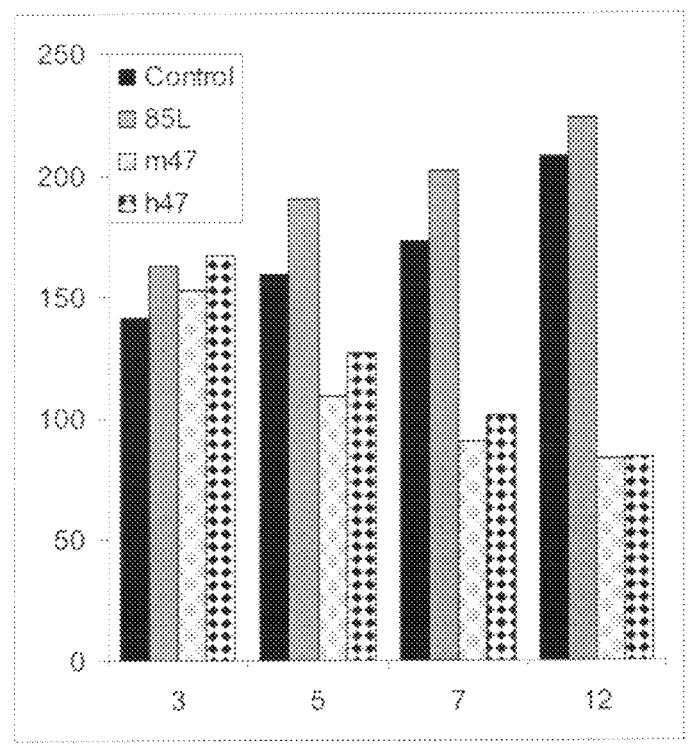
FIGS. 6A and 6B depict the results of an in vivo squamous cell carcinoma xenograft assay. Tumor volume is expressed on the Y-axis as $mm^3$ and the X-axis corresponds to the number of days following the beginning of treatment. Treatment with the mouse monoclonal antibodies #47 and #131 are compared with an exemplary deimmunized antibodies and control treatment.
Figure 6B:
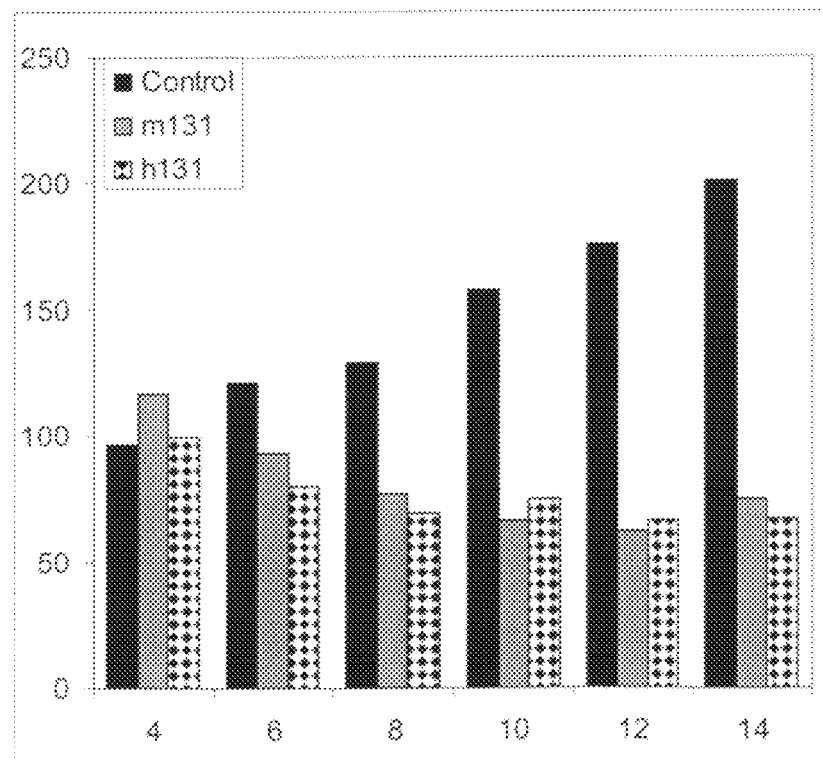

The following data (Tables 2 and 3) was collected from an in vivo squamous cell carcinoma xenograft assay. Tumor volume is expressed in $mm^3$ and the day number corresponds to the number of days following the beginning of treatment. The parent mouse monoclonal antibody, #47 or #131, is compared to an exemplary deimmunized antibody. The control group was administered vehicle alone. Results are also depicted graphically in FIGS. 6a and 6b.

TABLE 2

| Day | 3 | 5 | 7 | 12 |
|---|---|---|---|---|
| Control | 141.2 | 159.5 | 172.8 | 207.3 |
| 85L | 163.3 | 190.1 | 201.7 | 223.2 |
| m47 | 153 | 109.4 | 90.3 | 83.1 |
| h47 | 167.3 | 127.4 | 101.53 | 83.8 |

TABLE 3

| Day | 4 | 6 | 8 | 10 | 12 | 14 |
|---|---|---|---|---|---|---|
| Control | 96.30563 | 120.8 | 129 | 157.5 | 176.1 | 201.3 |
| m131 | 116.3825 | 92.8 | 77.1 | 66.6 | 62.1 | 75.1 |
| h131 | 99.52313 | 80.3 | 69.4 | 75 | 66.6 | 67.1 |

Both the exemplary deimmunized #47 antibody and the exemplary deimmunized #131 antibody showed similar levels of tumor growth inhibition as the mouse monoclonal #47 and #131 antibody, respectively. This is in stark comparison to the control as well as to a different mouse monoclonal anti-EphB4 antibody #85L, described in US application 2005/0249736.

The following data (Table 4) was collected from a colon cancer xenograft model assay on day 14 of treatment. As described above, the effect of treatment with either the mouse monoclonal antibody or a deimmunized variant is compared. Additionally, administration of IgG1 is also used as a control.

TABLE 4

| control | 448.7 |
|---|---|
| IgG1 | 436 |
| m131 | 207 |
| h131 | 170 |
| IgG1 | 436 |
| m47 | 212 |
| h47 | 230 |

From the above results, it is apparent that the disclosed deimmunized antibodies are effective in reducing tumor growth in at least two cancer xenograft models.

BRIEF DESCRIPTION OF SEQUENCES

SEQ ID NOs:1-5 correspond to the amino acid sequences of heavy chain variable region deimmunized variants derived from mouse monoclonal antibody #47.

SEQ ID NOs:6-9 correspond to the amino acid sequences of light chain variable region deimmunized variants derived from mouse monoclonal antibody #47.

SEQ ID NOs:10-14 correspond to the amino acid sequences of heavy chain variable region deimmunized variants derived from mouse monoclonal antibody #131.

SEQ ID NOs:15-18 correspond to the amino acid sequences of light chain variable region deimmunized variants derived from mouse monoclonal antibody #131.

SEQ ID NOs:19-21 correspond to the amino acid sequences of heavy chain variable region deimmunized CDRs from mouse monoclonal antibody #47.

SEQ ID NOs:22-24 correspond to the amino acid sequences of light chain variable region CDRs from mouse monoclonal antibody #47.

SEQ ID NOs:25-27 correspond to the amino acid sequences of heavy chain variable region CDRs from mouse monoclonal antibody #131.

SEQ ID NOs:28-30 correspond to the amino acid sequences of light chain variable region CDRs from mouse monoclonal antibody #131.

SEQ ID NOs:31-35 correspond to the nucleic acid sequences of heavy chain variable region deimmunized variants derived from mouse monoclonal antibody #47.

SEQ ID NOs:36-39 correspond to the nucleic acid sequences of light chain variable region deimmunized variants derived from mouse monoclonal antibody #47.

SEQ ID NOs:40-44 correspond to the nucleic acid sequences of heavy chain variable region deimmunized variants derived from mouse monoclonal antibody #131.

SEQ ID NOs:45-48 correspond to the nucleic acid sequences of light chain variable region deimmunized variants derived from mouse monoclonal antibody #131.

SEQ ID NO:49-52 correspond to the mouse monoclonal heavy and light chain variable region of antibody #47 and the mouse monoclonal heavy and light chain variable region of antibody #131, respectively.

SEQ ID NO:53 corresponds to the human EphB4 precursor protein.

SEQUENCE LISTING

SEQ ID NO:1: Heavy chain variable region deimmunized 47 variant 1
EVQLVQSGAELKKPGASVKISCKASGYTFTDYYMNWVKQAHGKGLEWIGD
NNPNNGGTTYNQKFKGRATLTVDKSTSTAYMELRSLRSEDSAVYYCARGK
YYGTSYGWYFDVWGQGTTVTVSS SEQ ID NO:2: Heavy chain variable region deimmunized 47 variant 2
EVQLVQSGAELKKPGASVKISCKASGYTFTDYYMNWVKQAHGKGLEWIGD
NNPNNGGTTYNQKFKGRATLTVDKSTSTAYMELSSLRSEDSAVYYCARGK
YYGTSYGWYFDVWGQGTTVTVSS SEQ ID NO:3: Heavy chain variable region deimmunized 47 variant 3
EVQLVQSGAEVKKPGASVKISCKASGYTFTDYYMNWVKQAPGKGLEWIGD
NNPNNGGTTYNQKFKGRATLTVDKSTSTAYMELSSLRSEDTAVYYCARGK
YYGTSYGWYFDVWGQGTTVTVSS SEQ ID NO:4: Heavy chain variable region deimmunized 47 variant 4
EVQLVQSGAEVKKPGASVKVSCKASGYTFTDYYMNWVKQAPGKGLEWIGD
NNPNNGGTTYNQKFKGRVTLTVDKSTSTAYMELSSLRSEDTAVYYCARGK
YYGTSYGWYFDVWGQGTTVTVSS SEQ ID NO:5: Heavy chain variable region deimmunized 47 variant 5
EVQLVQSGAEVKKPGASVKVSCKASGYTFTDYYMNWVRQAPGKGLEWIGD
NNPNNGGTTYNQKFKGRVTITVDKSTSTAYMELSSLRSEDTAVYYCARGK
YYGTSYGWYFDVWGQGTTVTVSS SEQ ID NO:6: Light chain variable region deimmunized 47 variant 1
DIQMTQSPSSLSASVGDRVTITCRISDNIDSYLAWFQQKQGKAPKLLVYD
ATVLADGVPSRFSGSGSGTQYTLTINSLQSEDAARYYCQVYYSIPWTFGQ
GTKLEIK SEQ ID NO:7: Light chain variable region deimmunized 47 variant 2
DIQMTQSPSSLSASVGDRVTITCRISDNIDSYLAWFQQKPGKAPKLLVYD
ATVLADGVPSRFSGSGSGTDYTLTINSLQAEDAARYYCQVYYSIPWTFGQ
GTKLEIK SEQ ID NO:8: Light chain variable region deimmunized 47 variant 3
DIQMTQSPSSLSASVGDRVTITCRISDNIDSYLAWFQQKPGKAPKLLVYD
ATVLADGVPSRFSGSGSGTDYTLTINSLQAEDAATYYCQVYYSIPWTFGQ
GTKLEIK SEQ ID NO:9: Light chain variable region deimmunized 47 variant 4
DIQMTQSPSSLSASVGDRVTITCRISDNIDSYLAWYQQKPGKAPKLLVYD
ATVLADGVPSRFSGSGSGTDYTLTINSLQAEDAATYYCQVYYSIPWTFGQ
GTKLEIK SEQ ID NO:10: Heavy chain variable region deimmunized 131 variant 1
QVQLVQSGAELKKPGASVKISCKASGYTFTDYYINWVKQAPGQGLEWIGK
IGPRIGTNYYNENFKGRATLTADISTNTAYMELSSLRSEDSAVYFCARSE
DYSGYVSYALDYWGQGTSVTVSS SEQ ID NO:11: Heavy chain variable region deimmunized 131 variant 2
QVQLVQSGAEVKKPGASVKISCKASGYTFTDYYINWVKQAPGQGLEWIGK
IGPRIGTNYYNENFKGRATLTADISTNTAYMELSSLRSEDTAVYFCARSE
DYSGYVSYALDYWGQGTLVTVSS SEQ ID NO:12: Heavy chain variable region deimmunized 131 variant 3
QVQLVQSGAEVKKPGASVKISCKASGYTFTDYYINWVKQAPGQGLEWIGK
IGPRIGTNYYNENFKGRVTLTADISTNTAYMELSSLRSEDTAVYYCARSE
DYSGYVSYALDYWGQGTLVTVSS SEQ ID NO:13: Heavy chain variable region
deimmunized 131 variant 4
QVQLVQSGAEVKKPGASVKVSCKASGYTFTDYYINWVRQAPGQGLEWIGK
IGPRIGTNYYNENFKGRVTLTADISTNTAYMELSSLRSEDTAVYYCARSE
DYSGYVSYALDYWGQGTLVTVSS SEQ ID NO:14: Heavy chain variable region
deimmunized 131 variant 5
QVQLVQSGAEVKKPGASVKVSCKASGYTFTDYYINWVRQAPGQGLEWIGK
IGPRIGTNYYNENFKGRVTLTADISTSTAYMELSSLRSEDTAVYYCARSE
DYSGYVSYALDYWGQGTLVTVSS SEQ ID NO:15: Light chain variable region
deimmunized 131 variant 1
NIVMTQSPASLSLSPGERVTLSCKASENVDTYVSWYQQKPDQSPKLLIYG
ASNRYTGVPDRFTGSGSATDFTLTISSLQAEDVADYHCGQTYRYPFTFGQ
GTKVEIK SEQ ID NO:16: Light chain variable region
deimmunized 131 variant 2
NIVMTQSPATLSLSPGERVTLSCKASENVDTYVSWYQQKPDQSPKLLIYG
ASNRYTGVPDRFTGSGSATDFTLTISSLQAEDVADYHCGQTYRYPFTFGQ
GTKVEIK SEQ ID NO:17: Light chain variable region
deimmunized 131 variant 3
NIVMTQSPATLSLSPGERVTLSCKASENVDTYVSWYQQKPDQSPKLLIYG
ASNRYTGVPDRFTGSGSATDFTLTISSLQAEDVAVYYCGQTYRYPFTFGQ
GTKVEIK SEQ ID NO:18: Light chain variable region
deimmunized 131 variant 4
NIVMTQSPATLSLSPGERVTLSCKASENVDTYVSWYQQKPDQSPKLLIYG
ASNRYTGVPDRFSGSGSATDFTLTISSLQAEDVAVYYCGQTYRYPFTFGQ
GTKVEIK SEQ ID NO:19: Mouse monoclonal antibody #47
heavy chain CDR1
DYYMN SEQ ID NO:20: Mouse monoclonal antibody #47
heavy chain CDR2
DNNPNNGGTTYNQKF SEQ ID NO:21: Mouse monoclonal antibody #47
heavy chain CDR3
GKYYGTSYGWYFDV SEQ ID NO:22: Mouse monoclonal antibody #47
light chain CDR1
RISDNIDSYLA SEQ ID NO:23: Mouse monoclonal antibody #47
light chain CDR2
DATVLAD SEQ ID NO:24: Mouse monoclonal antibody #47
light chain CDR3
QVYYSIPWT SEQ ID NO:25: Mouse monoclonal antibody #131
heavy chain CDR1
DYYIN SEQ ID NO:26: Mouse monoclonal antibody #131
heavy chain CDR2
KIGPRIGTNYYNENFK SEQ ID NO:27: Mouse monoclonal antibody #131
heavy chain CDR3
SEDYSGYVSYALDY SEQ ID NO:28: Mouse monoclonal antibody #131
light chain CDR1
KASENVDTYVS SEQ ID NO:29: Mouse monoclonal antibody #131
light chain CDR2
GASNRYT SEQ ID NO:30: Mouse monoclonal antibody #131
light chain CDR3
GQTYRYPFT SEQ ID NO:31: Heavy chain variable region
deimmunized 47 variant 1
GAGGTCCAGCTGGTGCAGTCTGGAGCTGAGCTGAAGAAGCCTGGGGCTTC
AGTGAAGATATCCTGTAAGGCTTCTGGATACACGTTCACTGACTACTACA
TGAACTGGGTGAAACAGGCACATGGAAAGGGACTTGAGTGGATTGGAGAT
AATAATCCTAATAATGGTGGTACTAACTACAACCAGAAGTTCAAGGGCAG
GGCCACATTGACTGTAGACAAGTCCACCAGCACAGCCTACATGGAGCTCC
GCAGCCTGCGATCTGAGGACTCTGCAGTCTATTACTGTGCAAGAGGAAAA
TACTACGGTACTAGCTACGGCTGGTACTTCGATGTCTGGGGCCAAGGGAC
CACGGTCACCGTCTCCTCA SEQ ID NO:32: Heavy chain variable region
deimmunized 47 variant 2
GAGGTCCAGCTGGTGCAGTCTGGAGCTGAGCTGAAGAAGCCTGGGGCTTC
AGTGAAGATATCCTGTAAGGCTTCTGGATACACGTTCACTGACTACTACA
TGAACTGGGTGAAACAGGCACATGGAAAGGGACTTGAGTGGATTGGAGAT
AATAATCCTAATAATGGTGGTACTAACTACAACCAGAAGTTCAAGGGCAG
GGCCACATTGACTGTAGACAAGTCCACCAGCACAGCCTACATGGAGCTCA
GCAGCCTGCGATCTGAGGACTCTGCAGTCTATTACTGTGCAAGAGGAAAA
TACTACGGTACTAGCTACGGCTGGTACTTCGATGTCTGGGGCCAAGGGAC
CACGGTCACCGTCTCCTCA SEQ ID NO:33: Heavy chain variable region
deimmunized 47 variant 3
GAGGTCCAGCTGGTGCAGTCTGGAGCTGAGGTGAAGAAGCCTGGGGCTTC
AGTGAAGATATCCTGTAAGGCTTCTGGATACACGTTCACTGACTACTACA
TGAACTGGGTGAAACAGGCACCTGGAAAGGGACTTGAGTGGATTGGAGAT
AATAATCCTAATAATGGTGGTACTAACTACAACCAGAAGTTCAAGGGCAG
GGCCACATTGACTGTAGACAAGTCCACCAGCACAGCCTACATGGAGCTCA
GCAGCCTGCGATCTGAGGACACTGCAGTCTATTACTGTGCAAGAGGAAAA
TACTACGGTACTAGCTACGGCTGGTACTTCGATGTCTGGGGCCAAGGGAC
CACGGTCACCGTCTCCTCA SEQ ID NO:34: Heavy chain variable region
deimmunized 47 variant 4
GAGGTCCAGCTGGTGCAGTCTGGAGCTGAGGTGAAGAAGCCTGGGGCTTC
AGTGAAGGTATCCTGTAAGGCTTCTGGATACACGTTCACTGACTACTACA
TGAACTGGGTGAAACAGGCACCTGGAAAGGGACTTGAGTGGATTGGAGAT
AATAATCCTAATAATGGTGGTACTAACTACAACCAGAAGTTCAAGGGCAG
GGTCACATTGACTGTAGACAAGTCCACCAGCACAGCCTACATGGAGCTCA
GCAGCCTGCGATCTGAGGACACTGCAGTCTATTACTGTGCAAGAGGAAAA
TACTACGGTACTAGCTACGGCTGGTACTTCGATGTCTGGGGCCAAGGGAC
CACGGTCACCGTCTCCTCA SEQ ID NO:35: Heavy chain variable region
deimmunized 47 variant 5
GAGGTCCAGCTGGTGCAGTCTGGAGCTGAGGTGAAGAAGCCTGGGGCTTC
AGTGAAGGTATCCTGTAAGGCTFTCTGGATACACGTTCACTGACTACTAC
ATGAACTGGGTGAGACAGGCACCTGGAAAGGGACTTGAGTGGATTGGAGA
TAATAATCCTAATAATGGTGGTACTAACTACAACCAGAAGTTCAAGGGCA
GGGTCACAATTACTGTAGACAAGTCCACCAGCACAGCCTACATGGAGCTC
AGCAGCCTGCGATCTGAGGACACTGCAGTCTATTACTGTGCAAGAGGAAA
ATACTACGGTACTAGCTACGGCTGGTACTTCGATGTCTGGGGCCAAGGGA
CCACGGTCACCGTCTCCTCA SEQ ID NO:36: Light chain variable region
deimmunized 47 variant 1
GACATCCAGATGACTCAGTCTCCATCTTCCCTGTCTGCATCTGTGGGAGA
CCGTGTCACCATCACATGTCGAATAAGTGACAATATTGACAGTTATTTAG
CATGGTTTCAGCAGAAACAGGGAAAAGCTCCTAAGCTCCTGGTCTATGAT
GCAACAGTCTTAGCAGATGGTGTGCCATCAAGGTTCAGTGGCAGTGGATC
AGGCACACAGTATACTCTCACGATCAACAGCCTGCAGTCTGAAGATGCTG
CGAGATATTACTGTCAAGTTTATTATAGTATTCCGTGGACGTTCGGTCAA
GGCACCAAGCTGGAAATCAAA SEQ ID NO:37: Light chain variable region
deimmunized 47 variant 2
GACATCCAGATGACTCAGTCTCCATCTTCCCTGTCTGCATCTGTGGGAGA
CCGTGTCACCATCACATGTCGAATAAGTGACAATATTGACAGTTATTTAG
CATGGTTTCAGCAGAAACGGGAAAAGCTCCTAAGCTCCTGGTCTATGAT
GCAACAGTCTTAGCAGATGGTGTGCCATCAAGGTTCAGTGGCAGTGGATC
AGGCACAGACTATACTCTCACGATCAACAGCCTGCAGGCTGAAGATGCTG
CGAGATATTACTGTCAAGTTTATTATAGTATTCCGTGGACGTTCGGTCAA
GGCACCAAGCTGGAAATCAAA -continued SEQ ID NO:38: Light chain variable region
deimmunized 47 variant 3
GACATCCAGATGACTCAGTCTCCATCTTCCCTGTCTGCATCTGTGGGAGA
CCGTGTCACCATCACATGTCGAATAAGTGACAATATTGACAGTTATTTAG
CATGGTTTCAGCAGAAACCGGGAAAAGCTCCTAAGCTCCTGGTCTATGAT
GCAACAGTCTTAGCAGATGGTGTGCCATCAAGGTTCAGTGGCAGTGGATC
AGGCACAGACTATACTCTCACGATCAACAGCCTGCAGGCTGAAGATGCTG
CGACATATTACTGTCAAGTTTATTATAGTATTCCGTGGACGTTCGGTCAA
GGCACCAAGCTGGAAATCAAA SEQ ID NO:39: Light chain variable region
deimmunized 47 variant 4
GACATCCAGATGACTCAGTCTCCATCTTCCCTGTCTGCATCTGTGGGAGA
CCGTGTCACCATCACATGTCGAATAAGTGACAATATTGACAGTTATTTAG
CATGGTATCAGCAGAAACCGGGAAAAGCTCCTAAGCTCCTGGTCTATGAT
GCAACAGTCTTAGCAGATGGTGTGCCATCAAGGTTCAGTGGCAGTGGATC
AGGCACAGACTATACTCTCACGATCAACAGCCTGCAGGCTGAAGATGCTG
CGACATATTACTGTCAAGTTTATTATAGTATTCCGTGGACGTTCGGTCAA
GGCACCAAGCTGGAAATCAAA SEQ ID NO:40: Heavy chain variable region
deimmunized 131 variant 1
CAGGTCCAGCTGGTGCAGTCTGGAGCTGAGCTGAAGAAGCCTGGGGCTTC
AGTGAAGATTTCCTGCAAGGCTTCTGGCTACACCTTCACTGACTACTACA
TTAACTGGGTGAAGCAGGCGCCTGGACAGGGCCTTGAGTGGATTGGCAAG
ATTGGTCCTCGAATTGGTACTAATTACTACAATGAAAACTTCAAGGGCAG
GGCCACACTGACTGCAGACATTTCCACCAACACAGCCTACATGGAGCTCT
CCTCCCTGAGATCTGAGGACTCTGCTGTCTATTTCTGTGCAAGATCTGAG
GACTACTCTGGTTATGTTTCCTATGCTTTAGACTACTGGGGTCAAGGAAC
CTCCGTCACCGTCTCCTCA SEQ ID NO:41: Heavy chain variable region
deimmunized 131 variant 2
CAGGTCCAGCTGGTGCAGTCTGGAGCTGAGGTGAAGAAGCCTGGGGCTTC
AGTGAAGATTTCCTGCAAGGCTTCTGGCTACACCTTCACTGACTACTACA
TTAACTGGGTGAAGCAGGCGCCTGGACAGGGCCTTGAGTGGATTGGCAAG
ATTGGTCCTCGAATTGGTACTAATTACTACAATGAAAACTTCAAGGGCAG
GGCCACACTGACTGCAGACATTTCCACCAACACAGCCTACATGGAGCTCT
CCTCCCTGAGATCTGAGGACACTGCTGTCTATTTCTGTGCAAGATCTGAG
GACTACTCTGGTTATGTTTCCTATGCTTTAGACTACTGGGGTCAAGGAAC
CCTCGTCACCGTCTCCTCA SEQ ID NO:42: Heavy chain variable region
deimmunized 131 variant 3
CAGGTCCAGCTGGTGCAGTCTGGAGCTGAGGTGAAGAAGCCTGGGGCTTC
AGTGAAGATTTCCTGCAAGGCTTCTGGCTACACCTTCACTGACTACTACA
TTAACTGGGTGAAGCAGGCGCCTGGACAGGGCCTTGAGTGGATTGGCAAG
ATFFGGTCCTCGAATTGGTACTAATTACTACAATGAAAACTTCAAGGGCA
GGGTCACACTGACTGCAGACATTTCCACCAACACAGCCTACATGGAGCTC
TCCTCCCTGAGATCTGAGGACACTGCTGTCTATTACTGTGCAAGATCTGA
GGACTACTCTGGTTATGTTTCCTATGCTTTAGACTACTGGGGTCAAGGAA
CCCTCGTCACCGTCTCCTCA SEQ ID NO:43: Heavy chain variable region
deimmunized 131 variant 4
CAGGTCCAGCTGGTGCAGTCTGGAGCTGAGGTGAAGAAGCCTGGGGCTTC
AGTGAAGGTTTCCTGCAAGGCTTCTGGCTACACCTTCACTGACTACTATA
TTAACTGGGTGAGGCAGGCGCCTGGACAGGGCCTTGAGTGGATTGGCAAG
ATTGGTCCTCGAATTGGTACTAATTACTACAATGAAAACTTCAAGGGCAG
GGTCACACTGACTGCAGACATTTCCACCAACACAGCCTACATGGAGCTCT
CCTCCCTGAGATCTGAGGACACTGCTGTCTATTACTGTGCAAGATCTGAG
GACTACTCTGGTTATGTTTCCTATGCTTTAGACTACTGGGGTCAAGGAAC
CCTCGTCACCGTCTCCTCA SEQ ID NO:44: Heavy chain variable region
deimmunized 131 variant 5
CAGGTCCAGCTGGTGCAGTCTGGAGCTGAGGTGAAGAAGCCTGGGGCTTC
AGTGAAGGTTTCCTGCAAGGCTTCTGGCTACACCTTCACTGACTACTACA
TTAACTGGGTGAGGCAGGCGCCTGGACAGGGCCTTGAGTGGATTGGCAAG
ATTGGTCCTCGAATTGGTACTAATTACTACAATGAAAACTTCAAGGGCAG
GGTCACACTGACTGCAGACATTTCCACCAACACAGCCTACATGGAGCTCT
CCTCCCTGAGATCTGAGGACACTGCTGTCTATTACTGTGCAAGATCTGAG
GACTACTCTGGTTATGTTTCCTATGCTTTAGACTACTGGGGTCAAGGAAC
CCTCGTCACCGTCTCCTCA SEQ ID NO:45: Light chain variable region
deimmunized 131 variant 1
AACATTGTAATGACCCAATCTCCCGCATCCCTGTCCCTGTCACCAGGAGA
GAGGGTCACCTTGAGCTGCAAGGCCAGTGAGAATGTGGATACTTATGTAT
CCTGGTATCAACAGAAACCAGACCAGTCTCCTAAATTGCTAATTTACGGG
GCATCCAACCGGTACACTGGAGTCCCTGATCGCTTCACAGGCAGTGGATC
TGCAACAGATTTCACTCTGACCATCAGCAGTCTTCAGGCTGAAGACGTTG
CAGATTATACTGTGGACAGACTTACAGGTATCCGTTCACGTTCGGACAG
GGGACCAAGGTGGAAATAAAA SEQ ID NO:46: Light chain variable region
deimmunized 131 variant 2
AACATTGTAATGACCCAATCTCCCGCAACCCTGTCCCTGTCACCAGGAGA
GAGGGTCACCTTGAGCTGCAAGGCCAGTGAGAATGTGGATACTTATGTAT
CCTGGTATCAACAGAAACCAGACCAGTCTCCTAAATTGCTAATTTACGGG
GCATCCAACCGGTACACTGGAGTCCCTGATCGCTTCACAGGCAGTGGATC
TGCAACAGATTTCACTCTGACCATCAGCAGTCTTCAGGCTGAAGACGTTG
CAGATTATACTGTGGACAGACTTACAGGTATCCGTTCACGTTCGGACAG
GGGACCAAGGTGGAAATAAAA SEQ ID NO:47: Light chain variable region
deimmunized 131 variant 3
AACATTGTAATGACCCAATCTCCCGCAACCCTGTCCCTGTCACCAGGAGA
GAGGGTCACCTTGAGCTGCAAGGCCAGTGAGAATGTGGATAUFFATGTAT
CCTGGTATCAACAGAAACCAGACCAGTCTCCTAAATTGCTAATTTACGGG
GCATCCAACCGGTACACTGGAGTCCCTGATCGCTTCACAGGCAGTGGATC
TGCAACAGATTTCACTCTGACCATCAGCAGTCTTCAGGCTGAAGACGTTG
CAGTTTATTACTGTGGACAGACTTACAGGTATCCGTTCACGTTCGGACAG
GGGACCAAGGTGGAAATAAAA SEQ ID NO:48: Light chain variable region
deimmunized 131 variant 4
AACATTGTAATGACCCAATCTCCCGCAACCCTGTCCCTGTCACCAGGAGA
GAGGGTCACCTTGAGCTGCAAGGCCAGTGAGAATGTGGATACTTATGTAT
CCTGGTATCAACAGAAACCAGACCAGTCTCCTAAATTGCTAATTTACGGG
GCATCCAACCGGTACACTGGAGTCCCTGATCGCTTCTCAGGCAGTGGATC
TGCAACAGATTTCACTCTGACCATCAGCAGTCTTCAGGCTGAAGACGTTG
CAGTTTATTACTGTGGACAGACTTACAGGTATCCGTTCACGTTCGGACAG
GGGACCAAGGTGGAAATAAA A SEQ ID NO:49: Mouse monoclonal antibody #47
heavy chain
EVQLQQSGPELVKPGASVKISCKASGYTFTDYYMNWVKQSHGKGLEWIGD
NNPNNGGTTYNQKFKGKATLTVDKSSSTAYMELRSLTSEDSAVYYCARGK
YYGTSYGWYFDVWGTGTTVTSS SEQ ID NO:50: Mouse monoclonal antibody #47
light chain
DIQMTQSPASLSASVGETVTITCRISDNIDSYLAWFQQKQGKSPQLLVYD
ATVLADGVPSRFSGSGSGTQYSLKINSLQSEDAARYYCQVYYSIPWTFGG
GTKLEIK SEQ ID NO:51: Mouse monoclonal antibody #131
heavy chain
QVQLKQSGAELVKPGASVKISCKASGYTFTDYYINWVKQRPGQGLEWIGK
IGPRIGTNYYNENFKGKATLTADISSNTAYMQLHTLTSEDSAVYFCARSE
DYSGYVSYALDYWGQGTSVTVSS SEQ ID NO:52: Mouse monoclonal antibody #131
light chain
NIVMTQSPKSMSMSVGERVTLSCKASENVDTYVSWYQQKPDQSPELLIYG
ASNRYTGVPDRFTGSGSATDFTLTISSVQAEDLADYHCGQTYRYPFTFGG
GTKLEIK SEQ ID NO:53: Human EphB4 Precursor Protein
MELRVLLCWASLAAALEETTLLNTKLETADLKWVTFPQVDGQWEELSGLDE
EQHSVRTYEVCDVQRAPGQAHWLRTGWVPRRGAVHVYATLRFTMLECLSL
PRAGRSCKETFTVFYYESDADTATALTPAWMENPYIKVDTVAAEHLTRKR
PGAEATGKVNVKTLRLGPLSKAGFYLAFQDQGACMALLSLHLFYKKCAQL
TVNLTRFPETVVPRELVVPVAGSCVVDAVPAPGPSPSLYCREDGQWAEQPV
TGCSCAPGFEAAEGNTKCRACAQGTFKPLSGEGSCQPCPANSHSNTIGSA
VCQCRVGYFRARTDPRGAPCTTPPSAPRSVVSRLNGSSLHLEWSAPLESG
GREDLTYALRCRECRPGGSCAPCGGDLTFDPGPRDLVEPWVVVRGLRPDF
TYTFEVTALNGVSSLATGPVPFEPVNVTTDDREVPPAVSDIRVTRSSPSSL
SLAWAVPRAPSGAVLDYEVKYHEKAEGPSSVRFLKTSENRAELRGLKRG
ASYLVQVRARSEAGYGPFGQEHHSQTQLDESEGWREQLALIAGTAVVGVV
LVLVVIVVAVLCLRKQSNGREAEYSDKHGQYLIGHGTKVYIDPFTYEDPN
EAVREFAKEIDVSYVKIEEVIGAGEFGEVCRGRLKAPGKKESCVAIKTLK
GGYTERQRREFLSEASIMGQFEHPNIIRLEGVVTNSMPVMILTEFMENGA
LDSFLRLNDGQFTVIQLVGMLRGIASGMRYLAEMSYVHRDLAARNILVNS
NLVCKVSDFGLSRFLEENSSDPTYTSSLGGKIPIRWTAPEAIAFRKFTSA
SDAWSYGIVMWEVMSFGERPYWDMSNQDVINAIEQDYRLPPPPDCPTSLH -continued QLMLDCWQKDRNARPRFPQVVSALDKMIRNPASLKIVARENGGASHPLLD
QRQPHYSAFGSVGEWLRAIKMGRYEESFAAAGFGSFELVSQISAEDLLRI
GVTLAGHQKKILASVQHMKSQAKPGTPGGTGGPAPQY

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A deimmunized antibody or antigen binding fragment thereof that binds amino acids 1-537 of SEQ ID NO:53, comprising a heavy chain variable region and a light chain variable region, wherein the heavy chain variable region comprises the amino acid sequence of SEQ ID NO:14; and the light chain variable region comprises the amino acid sequence of SEQ ID NO:18.

2. The deimmunized antibody or antigen binding fragment thereof according to claim 1 with similar or greater binding affinity to amino acids 1-537 of SEQ ID NO:53 than a mouse monoclonal antibody produced from the hybridoma ATCC#PTA-6214.

3. The deimmunized antibody or antigen binding fragment thereof according to claim 1, wherein the deimmunized antibody or antigen binding fragment thereof is conjugated to a cytotoxic agent.

4. A pharmaceutical composition comprising the deimmunized antibody or antigen binding fragment thereof according to claim 1.

5. A deimmunized antibody or antigen binding fragment thereof that binds amino acids 1-537 of SEQ ID NO:53, comprising a heavy chain variable region and a light chain variable region, wherein the heavy chain variable region comprises the amino acid sequence of SEQ ID NO:3 and the light chain variable region comprises the amino acid sequence of SEQ ID NO:8.

6. The deimmunized antibody or antigen binding fragment thereof according to claim 5 with similar or greater binding affinity to amino acids 1-537 of SEQ ID NO:53 than a mouse monoclonal antibody produced from the hybridoma ATCC#PTA-11338.

7. The deimmunized antibody or antigen binding fragment thereof according to claim 5, wherein the deimmunized antibody or antigen binding fragment thereof is conjugated to a cytotoxic agent.

8. A pharmaceutical composition comprising the deimmunized antibody or antigen binding fragment thereof according to claim 5.

* * * * *